United States Patent
Qi

(10) Patent No.: US 11,253,358 B2
(45) Date of Patent: Feb. 22, 2022

(54) STENT APPARATUS HAVING SELF-PLEATED SKIRT, PROCESSING METHOD THEREFOR, SKIRT PLEATING METHOD, AND CARDIAC VALVE

(71) Applicant: VENUS MEDTECH (HANGZHOU), INC., Zhejiang (CN)

(72) Inventor: Jesse Jun Qi, Irvine, CA (US)

(73) Assignee: Venus Medtech (Hangzhou), Inc., Hangzhou (CN)

( * ) Notice: Subject to any disclaimer, the term of this patent is extended or adjusted under 35 U.S.C. 154(b) by 158 days.

(21) Appl. No.: 16/807,424

(22) Filed: Mar. 3, 2020

(65) Prior Publication Data
US 2020/0289261 A1   Sep. 17, 2020

Related U.S. Application Data

(63) Continuation of application No. PCT/CN2018/103945, filed on Sep. 4, 2018.

(51) Int. Cl.
*A61F 2/24* (2006.01)
(52) U.S. Cl.
CPC .......... *A61F 2/2418* (2013.01); *A61F 2/2409* (2013.01); *A61F 2/2415* (2013.01);
(Continued)
(58) Field of Classification Search
CPC .................. A61F 2/2418; A61F 2/2409; A61F 2250/0069
See application file for complete search history.

(56) References Cited

U.S. PATENT DOCUMENTS

| | | | |
|---|---|---|---|
| 2013/0018458 A1 | 1/2013 | Yohanan et al. | |
| 2014/0243966 A1* | 8/2014 | Garde | A61F 2/2418 623/2.18 |

(Continued)

FOREIGN PATENT DOCUMENTS

| | | |
|---|---|---|
| CN | 103006352 A | 4/2013 |
| CN | 105188609 A | 12/2015 |

(Continued)

OTHER PUBLICATIONS

International Search Report dated Nov. 22, 2018 for corresponding PCT Application No. PCT/CN2018/103945.
Office Action dated Jul. 16, 2021 for corresponding European Application No. 18851593.6.

*Primary Examiner* — Suba Ganesan
(74) *Attorney, Agent, or Firm* — Raymond Sun

(57) ABSTRACT

Disclosed in the present invention are a stent apparatus having a self-pleated skirt, a processing method therefor, a skirt pleating method, and a cardiac valve. The stent apparatus comprises a stent, and is further provided with a flexible skirt. The skirt comprises: an unfolded state, where the skirt extends axially and surrounds the periphery of the stent before release; and a stacked state, where the skirt is driven by deformation during release of the stent, and gathers and is stacked along an axial direction of the released stent to form an annular perivalvular leakage blocking part. The stent apparatus is further provided with a pull-wire which is merely threaded on the skirt, and the pull-wire may react to the radial deformation during the release of the stent to drive the skirt to enter the stacked state. According to the present invention, based on perivalvular leakage prevention technology, an interventional stent is fitted with the lining of the blood vessels, so that the stent will not easily be migrated and is more stable, the scope of the applicable population is expanded, additional surgical risks are lowered, and perivalvular leakage, thrombi and other complications are pre- (Continued)

vented. Better hemodynamic performance is provided, the coverage function of endothelial cells of the host is enhanced, the probability of occurrence of endocarditis is lowered, and the normal blood supply function of the heart and blood vessels is recovered.

20 Claims, 39 Drawing Sheets

(52) U.S. Cl.
CPC .......... *A61F 2/2433* (2013.01); *A61F 2/2439* (2013.01); *A61F 2210/0057* (2013.01); *A61F 2220/0008* (2013.01); *A61F 2220/0016* (2013.01); *A61F 2220/0075* (2013.01); *A61F 2250/0051* (2013.01); *A61F 2250/0069* (2013.01)

(56) References Cited

U.S. PATENT DOCUMENTS

| | | | |
|---|---|---|---|
| 2015/0005863 A1* | 1/2015 | Para | A61F 2/2418 623/1.2 |
| 2015/0209136 A1* | 7/2015 | Braido | A61F 2/2403 623/2.18 |
| 2016/0220359 A1* | 8/2016 | Backus | A61F 2/2412 |
| 2016/0262878 A1 | 9/2016 | Backus et al. | |
| 2016/0367364 A1 | 12/2016 | Torrianni et al. | |
| 2017/0273784 A1* | 9/2017 | Racchini | A61F 2/2427 |
| 2018/0055631 A1* | 3/2018 | Morin | A61F 2/2412 |

FOREIGN PATENT DOCUMENTS

| | | |
|---|---|---|
| WO | WO2009/044082 A2 | 4/2009 |
| WO | WO2015/152980 A1 | 10/2015 |

* cited by examiner

STENT APPARATUS HAVING SELF-PLEATED SKIRT, PROCESSING METHOD THEREFOR, SKIRT PLEATING METHOD, AND CARDIAC VALVE

TECHNICAL FIELD

The present application relates to the technical field of medical apparatuses, and in particular, to an artificial stent apparatus for a heart or a blood vessel and a processing method therefor.

BACKGROUND

Since the 1970s, artificial heart valve replacement, as an effective treatment for end-stage heart valve disease, has saved millions of patients' lives. Artificial heart valve replacement is a revolutionary breakthrough in heart valve treatment technology, and has broad prospects.

Perivalvular leakage (PPL) is a serious and unique postoperative complication of valve replacement and is one of the common reasons which cause reoperations. The reason why PPL occurs is mainly related to the pathological changes of the annulus tissue such as degenerative changes, rheumatic or senile calcification, acute infective endocarditis invading the annulus or perivalvular abscess, mismatch in size between the artificial valve and the annulus, and prosthetic valve endocarditis.

Peripheral leakage occurs not only when implanting an artificial stent in the heart, but also in blood vessels or other body channels. For ease of description, perivalvular leakage is mainly taken as an example here.

The perivalvular leakage usually has the following adverse effects: (1) severe hemolysis, anemia, and progressively increased hemoglobinuria; (2) abnormal changes in hemodynamics, failure of heart function or even heart failure caused by large orifices for perivalvular leakage, with poor symptoms and signs improvement after conservative treatments; (3) infective endocarditis concurrent even with a small orifice for perivalvular leakage; and (4) bioprosthetic valve failure concurrent with a perivalvular leakage.

At present, some research work has been done on the prevention of perivalvular leakage, at home and abroad. However, the perivalvular leakage cannot be decreased to a rate below 5% during transcatheter replacement at this time. Therefore, further research work is needed on how to reduce the perivalvular leakage.

At present, the main method of transcatheter bioprosthetic valve implantation for the treatment of heart valve disease is to compress an artificial heart valve into a delivery device, which delivers the valve to a lesion site of the heart through blood vessels, and then release the artificial heart valve to replace the diseased native valve. Typical heart valves include balloon expandable valves or self-expanding artificial heart valves. The self-expanding artificial heart valve generally includes a meshed stent made of a shape memory metal material, and a valve sewn in the stent which opens unidirectionally. During implantation, the stent expands itself and fits the diseased annulus as much as possible. Although the perivalvular leakage can be reduced to a certain extent, the perivalvular leakage and peripheral back flow will still occur more or less to some patients who have blood vessels with irregular inner walls due to autocalcification. The stent of the balloon expandable valve is usually made of medical stainless steel. During implantation, the stainless steel stent is expanded by the balloon and fits the diseased annulus as much as possible.

The typical balloon expandable valve or self-expanding valve expands the inner wall of the blood vessel only by the radial support force of the metal stent. For patients who have blood vessels with regular inner walls, an appropriate stent may be chosen to substantially fit the inner walls of the blood vessels by valve selection, which can reduce perivalvular leakage to a certain degree. However, for patients who have blood vessels with irregular inner walls caused by calcification, perivalvular leakage will occur more or less. A large number of clinical studies indicate that it is difficult to reduce the perivalvular leakage to a rate below 5%, so the risk of perivalvular leakage still exists. At present, once a patient suffers from perivalvular leakage, it can only be solved by measures such as repair and valve replacement, which results in a high risk for surgery and thus to the patient's life.

Although there have some typical solutions, all of these solutions have certain shortcomings. For example, perivalvular leakage may be prevented by providing an annular pocket around the periphery of a stent, which would be filled with back-flow blood. However, it is likely to generate thrombus in the annular pocket, and there is a risk that the thrombus may fall off.

There are also some solutions which block perivalvular leakage by forming an annular protrusion protruding radially with a water-absorbing expansion material on the outer periphery of the stent, while there is also a risk that the water-absorbing expansion material may fall off, which results in potential danger.

There are also some solutions provided with a flexible film at an inflow end of the stent, wherein the flexible film is located at an axial side of the stent before being released, and rolled up or folded up near the inflow end of the released stent to form an annular protrusion protruding radially so as to block perivalvular leakage.

However, as the flexible film is provided at the axial side of the stent before being released, which makes the entire length of the resulting stent apparatus too long, thereby resulting in higher requirements for a delivery system. More importantly, in order to achieve the rolling or folding of the flexible film, an additional dragging mechanism must be provided, which is controlled by an operator and thus increases the complexity and difficulty of control. Alternatively, a metal member may be provided, which, based on the characteristic of having a preset shape thereof, drives the flexible film to roll up or fold up after being released in the human body. However, the metal member makes the structure of the stent more complicated, and brings additional risks. Furthermore, under the influence of the space outside of the stent, it is difficult to pull the flexible film to the desired position. Therefore, the effects are not satisfied.

SUMMARY

The invention provides a stent apparatus with a self-folded skirt, which forms a peripheral leakage occluder by stacking a flexible skirt around an outer periphery of a released stent, and is able to seal the outer periphery of the stent in a flexible manner, with safe operation and convenient processing.

A stent apparatus with a self-folded skirt, comprising a stent and a flexible skirt, wherein the flexible skirt has:

an unfolded configuration, in which the skirt is axially unfolded and surrounds an outer periphery of the stent before being released;

a stacked configuration, in which the skirt is folded and stacked in an axial direction of the stent after being released and forms an annular peripheral leakage occluder;

the stent apparatus is further provided with a pulling string that only threads though the skirt, wherein, the pulling string operates in cooperation with radial deformation of the stent during release so as to drive the skirt to transform into the stacked configuration.

Individual configurations of the skirt are configured to adapt to a released stent and an unreleased stent, respectively. The stent is provided in a radially compressed configuration, i.e. a configuration before being released, after being loaded into a delivery system. Correspondingly, the skirt is provided in the unfolded configuration. In order to facilitate the travel of the stent in the human body, the stent should be compressed as much as possible. Correspondingly, the skirt and the pulling string are unfolded in the axial direction. The skirt surrounds around the outer periphery of the stent before being released in the present invention, at least with most of the skirt surrounding around the outer periphery of the stent, rather than being located at an axial side of the stent. Since the skirt is thin and has a good flexibility, it is able to conform very well to the outer periphery of the stent.

After being delivered into the human body with the delivery system, the stent starts to be released and gradually expands radially. After the release is completed, the shape of the stent remains relatively stable and fixed. During the release of the stent, the radial expansion of the stent is accompanied by changes in the circumferential direction, i.e., the perimeter increases. The pulling string on the skirt operates in cooperation with the radial expansion of the stent. The axial folding corresponding to the circumferential expanding of the pulling string will drive the skirt and initiate axial folding and stacking in the axial direction, and to be thickened around the outer periphery of the stent, so as to form the annular peripheral leakage occluder.

When axially unfolded, the skirt in the unfolded configuration minimizes the radial dimension of the stent in the compressed configuration before being released. In addition, the skirt will be axially unfolded by the sheath during load. The term axially unfolded described in the present invention should not be strictly limited to the meaning that the skirt "must" be axially unfolded and straightened, but should be interpreted as the skirt "may" be axially unfolded due to the structure of the skirt and the position or connection relationship between the skirt and the stent.

There is no strict limit to the specific stacked structure of the stent during axial folding and stacking, provided that axially folding the skirt will at least cause a thickening of the skirt in the radial direction for sealing the peripheral leakage.

During the release of the stent, the skirt of the present invention is transformed from the unfolded configuration, which is relatively flat, to the stacked configuration in the axial direction of the stent under the pulling string. The skirt being stacked will inevitably be expanded radially, in other words, it will be thickened relative to the corresponding portion of the stent and thus supports or blocks around the periphery of the valve, which is able to effectively reduce the gap between the periphery of the stent and the inner wall of the blood vessel, thereby decreasing the peripheral leakage, and preventing back flow around the periphery of the valve and looseness of the fixed valve stent. Therefore, the current problems of difficulty in fixing an implanted valve and peripheral leakage may be solved, with the success rate for the operation of an implanted heart valve and the health condition of patients greatly improved.

The present invention provides that the pulling string only threads though the skirt, this is relative to the connection relationship between the pulling string and the stent. There is a known pulling string connected between the stent and the skirt, which is fixed to the stent or at least threads through the stent to form a bent course. The pulling string of the present invention only threads though the skirt and is located around the outer periphery of the stent. The pulling string is neither directly fixed to the stent, nor bent by directly utilizing any gap in the structure of the stent, nor threading into the interior of the stent.

The pulling string also forms an undulating structure while threading through the skirt along the circumferential direction. The overall pulling string will be subjected to a radial supporting and expanding force of the stent being released, and its undulating structure will be changed to a certain extent, thereby driving the skirt to be axially folded.

A portion of the pulling string or a single pulling string of a plurality of pulling strings may serve as a single unit for driving a floating section to be folded axially. The principle for one example is the deformation mechanism of a triangle, that is, in the case that the overall length of two sides of the triangle are fixed, the angle between the two sides with fixed length will increase when the length of the third side is increased, and the vertex corresponding to the two sides will get closer to the third side.

The pulling string itself may be considered as the two sides with fixed length, with a bent portion therebetween which may be considered as the intersection point of the two sides. During the release of the stent, the perimeter of the skirt will increase, which means that the length of the third side of the triangle increases, and the intersection point therefore will get closer to the third side.

If more bent portions are provided, the single unit may be developed as a quadrangle or a polygon instead of triangle, in which each side may be a straight or curved side when tensioned. The bent portions may be provided by the stent or the skirt, or by additional guide members.

Due to the pulling string of the present invention, there are no strict requirements for the engagement between the skirt and the outer periphery of the stent as the skirt can in any event be pulled and stacked by means of the pulling string. The length of the pulling string remains unchanged in both the compressed configuration before the stent is released and the expanded configuration after the stent is released. In the expanded configuration of the stent, the pulling string is expanded radially with the expansion of the stent. The axial extension length of the pulling string will be shortened along with the increase of the circumferential extension length of the pulling string, which will simultaneously drive the skirt to be folded axially and transformed into the stacked configuration. Many alternative or preferred arrangements are further provided only for additional or preferred implementation, without any limitation to the above general solution. Without conflict in technique or logic, the arrangement may be combined with the above general solution alone or multiple arrangements may be combined with each other.

Optionally, in a released condition of the stent, the skirt loosely fits, conforms to, or is tightly mounted on, the outer periphery of the stent.

The terms loosely fitting, conforming, or being tightly mounted are defined based on the degree of tightness of the engagement between the skirt and the stent, wherein the loosely fitting means that the skirt is engaged relatively loosely with the outer periphery of the stent and there is a certain amount of floating space for the skirt; the conforming means that the skirt is exactly conforming with the outer periphery of the stent with the free floating being limited, and without being tightened too much with respect to each other; and being tightly mounted means that the skirt constrains on the outer periphery of the stent under the expanding force of the stent with the elasticity of the skirt or the stent itself.

It is necessary that the stent will expand radially after being released into the human body. The pulling string of the present invention operates in cooperation with the deformation of the stent, during radial deformation of the stent, a force will be generated and transmitted to the pulling string which will in turn drive the skirt to be pulled and folded. A pulling force is transmitted via the flexible pulling string from the stent to the skirt. The diameter of the stent increases when it is released. Two points on the stent that are located close to each other in the circumferential direction before the stent is released will move away from each other after the stent is released. Based on this principle, the pulling string pulls the skirt by transmission of the pulling force.

Preferably, the pulling string comprises a driving portion and a force exerting portion, wherein, the driving portion comprises at least two threading ends interacting with the skirt, and the circumferential span between the two threading ends changes after the stent is released relative to the stent being unreleased, and wherein, a relative displacement in the axial direction of the stent between the force exerting portion and the driving portion is produced during the release of the stent to pull the skirt to be stacked. The pulling string is directly connected to, or threads through, the skirt via the at least two threading ends, and cooperates with the radial expansion of the stent during release and is expanded radially.

The threading ends are the portions where the pulling string interacts with the skirt directly. With the relative movement between the pulling string and a part of the skirt, the position of the threading ends relative to the pulling string changes dynamically.

The driving portion and the force exerting portion, as parts of the pulling string, may be segments of the pulling string with certain lengths, or may be certain points. As the stent expands and deforms, the circumferential span of the driving portion increases, and the length of the pulling string in the circumferential direction increases. Accordingly, the force exerting portion interacting with the skirt is pulled to axially move closer thereto, thereby driving the skirt to be folded.

The pulling force may be oriented parallel to or inclined to the axial direction of the stent, as long as the pulling force has at least a component in the axial direction which drives the force exerting portion to move axially.

The driving portion and the force exerting portion are relative concepts, which are named just for the convenience of illustrating the functions. In other words, it is assumed that only the circumferential span of the driving portions changes, the force exerting portion will be driven and the axial position thereof will be changed. Conversely, when the circumferential span of force exerting portions changes, the associated driving portion will be driven and the axial position thereof will be changed, in which case, the functions of the driving portion and the force exerting portion are interchanged. In practice, different parts of the pulling string, or the pulling string and the stent, operate in cooperation with each other anywhere. Different parts of the pulling string may be considered either as the driving portion or as the force exerting portion from different perspectives, that is, the parts may play dual roles. Therefore, although different parts of the pulling string are specifically named, there is no additional limitation to the extending or threading techniques of the pulling string, instead, only the cooperation relationship between different parts of the pulling string, and the cooperation relationship between the pulling string and the skirt, are emphasized.

During the release of the stent, the radial expansion of the stent is accompanied by changes in the circumferential direction, i.e., the perimeter increases. The pulling string on the stent/skirt operates in cooperation with the radial expanding of the stent. The axial gathering corresponding to the circumferential expanding of the pulling string will drive the skirt to be folded and stacked in the axial direction, and to be further thickened around the outer periphery of the stent, so as to form the annular peripheral leakage occluder.

The length of the pulling string is fixed in both the compressed configuration of the stent before being released and the expanded configuration of the stent after being released. In the expanded configuration of the stent, the pulling string is expanded radially with the expanding of the stent. The axial extension length of the pulling string will be shortened along with the increase of the circumferential extension length of the pulling string, which will simultaneously drive the skirt to be folded axially and transformed into the stacked configuration.

In the fully expanded configuration of the stent, the pulling string maintains the skirt in the folded and stacked configuration.

During preparation of the stent apparatus, the skirt is maintained in the folded and stacked configuration by the pulling string, while the stent is in the fully expanded configuration. The steps for forming the stent include: a, arranging a prepared skirt around an outer periphery of the stent in a released configuration; b, threading pulling string through the skirt according to a preset course; c, pulling the pulling string to drive the skirt into a stacked configuration; and d, fixing ends of the pulling string.

In the folded and stacked configuration of the skirt, the pulling string extends circumferentially, and preferably, the pulling string is tensioned.

The pulling string that circumferentially extends or is tensioned or tightened does not prevent the stent from expanding.

In the compressed configuration of the stent before being released, the skirt extends axially, and the pulling string extends axially and does not extend beyond the bottom side of the skirt.

The driving portion and the force exerting portion of the pulling string, as parts of the pulling string, may be segments of the pulling string with certain lengths, or may be certain points. As the stent expands and deforms, the circumferential span of the driving portion increases, and the length of the pulling string in the circumferential direction increases. Accordingly, the force exerting portion interacting with the skirt is pulled to axially move closer thereto, thereby driving the skirt to be folded.

In the compressed configuration of the stent, i.e., in the unfolded configuration of the skirt, the pulling string should be straightened as much as possible or slightly tightened between the two bent points (under the guidance of the stent or the skirt), at least neither being loosened nor extending beyond the axial side of the skirt, in order to provide a timely response to the deformation of the stent being released so as to render the skirt to be pulled axially. Otherwise, the loosened part of the pulling string will delay or even offset the deformation of the stent, which will affect the effect of pulling the skirt. In the expanded configuration of the stent, the length of the pulling string should not be too short to constrain the stent tightly and prevent the stent from expanding.

Preferably, at least one section of the skirt in the axial direction is configured as a floating section around the outer periphery of the stent, and the floating section is configured to be pulled by the pulling string and thus be axially stacked.

In order to allow the skirt to be deformable in the axial direction and thus be folded and stacked, at least a section of the skirt is required to be axially movable relative to the outer periphery of the stent. The floating section referred to in the present invention may be regarded as an axial floating section, which is axially movable and not necessarily circumferentially movable. In order to guide the axial movement of the floating section, it is possible to provide a guide mechanism. Therefore, the circumferential movement is not necessarily related to the axial movement. Actually, at least a part of the skirt is circumferentially movable. The floating section may generally be provided with or without circumferential positioning.

The pulling string utilizes the axial mobility of the floating section to pull the floating section, however, the force transmission may be achieved by means of the stent or skirt.

Preferably, there are two floating sections arranged in the axial direction, and the floating sections are transformed into the stacked configurations independently or in an interlinked manner.

Individual floating sections may be pulled and folded by using their respective driving mechanisms. Without taking the release sequence into consideration, that is, assuming that the floating sections are released at the same time, depending on the threading techniques of the pulling string, the floating sections may be transformed into the stacked configurations in an interlinked manner if the pulling strings corresponding thereto are connected or are configured as the same pulling string. Even taking the release sequence into consideration, the floating section released first may also bring a certain degree of pre-stress to the floating section that is not released yet, so as to assist the latter to be released and transformed into the stacked configuration.

In a similar way, if the pulling strings corresponding to individual floating sections are relatively independent, the floating sections may be transformed into the stacked configurations independent from each other.

In addition, since the floating sections are different parts of the same skirt, the mutual pulling of different parts of the skirt itself may also cause the floating sections to be transformed into the stacked configuration in an interlinked manner.

Optionally, two adjacent floating sections are arranged in a spaced, adjacent or overlapped manner in the axial direction.

The spaced arrangement means that the projections of the two adjacent floating sections in the axial direction of the stent are spaced apart. The adjacent arrangement means that the projections of the two adjacent floating sections in the axial direction of the stent are directly adjacent to and in contact with each other. The overlapped arrangement means that the projections of the two adjacent floating sections in the axial direction of the stent are overlapped.

In general, each floating section has a cylindrical shape in a relaxed state without radial compression and axial stacking. The relationship of the two adjacent floating sections is affected by the positions of fixing bands. In a further preferred manner, the two adjacent floating sections are spaced in the axial direction, which can form two peripheral leakage occluders with definite boundaries, thereby performing multiple sealing functions.

Optionally, the floating section has two axial edges, one of which is fixed on the stent, and the other serves as a floating edge.

Alternatively, both of the two axial edges of the floating section are fixed on the stent.

For ease of illustration, the two axial edges of the floating section are, as an example, the top and bottom edges. The top and bottom edges are either floated relative to the stent (as floating edges) or arranged adjacent to the fixing band and fixed relative to the stent. As further preferred, the top edge of the floating section is fixed on the stent, and the bottom edge serves as the floating edge. For example, only the top edge of the entire skirt is provided with a fixing band, and the remaining portion of the skirt serves as the floating section, and therefore the bottom edge of the floating section, i.e., the bottom edge of the skirt, serves as the floating edge. The term floated and floating referred to in the present invention may be interpreted as at least being axially movable relative to the stent.

Optionally, before the stent is released, the floating section is unfolded along the axial direction of the stent, or has a folded structure.

The folded structure of the floating section may be folded in an axial direction, in a circumferential direction, or in an axial direction along with in a circumferential direction. Alternatively, the folded structure of the floating section may be folded in a more complicated and irregular technique. In any event, the floating section at least conforms the outer wall of the stent in the radial direction under the constraint of the delivery system.

Optionally, one of the two axial edges of the floating section is fixed to the stent entirely or partially along the circumferential direction.

The two axial edges of the floating section may be fixed to the stent by fixing bands, which is stitched continuously or discontinuously with a plurality of stitching points spaced-apart in a circumferential direction.

The floating section, as a part of the skirt, is fixed to the outer periphery of the stent through the fixing band according to the previous disclosure. The fixing band itself is not a part of the floating section, while the floating section is connected to the stent by the fixing band connected thereto. The techniques of stitching continuously or discontinuously are related to the shape of the edge of the floating section.

The stent of the present invention may be a known stent, for example, with a generally cylindrical shape, and being processed by braiding or cutting. It has a meshed structure with a plurality of grids arranged regularly or partially combined with other structures having different shapes.

The stent may be used in the aorta, aortic valve, pulmonary artery, pulmonary valve, mitral valve, tricuspid valve, occluding device, general blood vessel or the like. The shape of the stent and the presence of the coverage membrane may be adaptable based on the prior art as required.

Preferably, one section of the stent in the axial direction is configured as a flared driving structure that is configured to drive the skirt to be folded and stacked.

The stent may take a flared configuration during the release. In order to further ensure that the skirt can be folded and stacked in the axial direction, the stent itself may also form a flared driving structure at a section thereof corresponding to the skirt. In addition, the guidance of the flared structure functions to maintain the skirts in the stacked configuration after the stent is completely released without loosening in the axial direction, so as to ensure the function of the peripheral leakage occluder.

Preferably, the flared driving structure is located at a middle portion of the stent in the axial direction, or adjacent to axial ends of the stent.

Preferably, the flared driving structure is adjacent to an axial end of the stent, and is flared at the corresponding end.

Preferably, the flared driving structure is adjacent to the blood inflow end of the stent, and the closer to the blood inflow end, the wider the opening of the flared driving structure. An appropriately orientated flared driving structure may operate in cooperation with the blood flow to push the skirts to axially stack. A blood flow from the wide opening to the narrow opening has a function in compliance with the guidance of the flared driving structure. It is further preferred that the wide opening side of the flared driving structure is released first, and the narrow opening side is released later, which works on the skirt in cooperation with the flared structure of the stent during the release, so as to guide the skirt to be axially stacked and to maintain the skirt in the stacked configuration.

Preferably, the flared driving structure extends to the distal end of the stent which is to be released first.

The flared driving structure extending to the distal end of the stent which is to be released first has the following advantages: when the stent starts to be released, the flared structure thereof presents clearly, and in addition, the axial limit to the peripheral leakage occluder may be steadily maintained.

Optionally, the generatrix of the flared driving structure is a straight line, a smooth curved line, or a combination of a straight line and a curved line.

The shape of the generatrix determines the extension of the flared mouth and is not strictly limited in the present invention. The generatrix may be a single straight line or smooth curved line, or a combination of a straight line and a curved line, provided that a generally flared structure is formed and the flared driving structure should at least function at the distal end of the skirt to be released first.

Preferably, both ends of the skirt in the unfolded configuration along the axial direction of the stent do not extend beyond the corresponding sides of the stent.

Preferably, one axial side edge of the stent has a sharp angled structure, and before the stent is released, the corresponding side of the skirt does not extend axially beyond the tips of the sharp angled structure.

When the stent is being released, the distal end which is to be released first will turn outwardly. If the skirt in the unfolded configuration covers the side with the tips, the distal end of the stent to be released first may snag the inner side of the skirt or even pierce the skirt, which would prevent the skirt from being axially folded. The typical stents are generally in meshed structures, with end nodes of grids or sharp tips at the distal end to be released first, which are likely to snag on the skirt during release.

Therefore, it is preferred that at least a part of the stent is released at the earliest point and then works on the skirt so as to automatically guide the skirt to be stacked.

Before the stent is released, the corresponding side of the skirt may be unfolded in a single layer, rolled inwards/outwards, folded or stacked. In any event, it is preferred that the axial edge of the skirt does not extend beyond the tips of the sharp angled structure at the corresponding side.

Preferably, before the stent is released, at least a portion of the distal end of the stent to be released first is exposed outside the skirt, and the exposed portion is released before the skirt.

Preferably, a section of the stent in the axial direction is a flared driving structure that drives the skirt to be folded and stacked, and at least a portion of the flared driving structure is configured as said exposed portion.

It is apparent to have a coordinative effect by releasing the stent before the skirt in combination with said flared driving structure.

In order to facilitate the stacking of the skirt, at least to prevent the skirt from being "snagged" during the release of the stent, it is further preferred that an axial end of the stent has a smooth curved edge. Due to such configuration, the corresponding side of the skirt may extend axially beyond the stent before the stent is released.

For example, the edge of the distal end of the stent to be released first is formed by a plurality of curved segments connected one another, and the skirt extends axially beyond the distal end of the stent to be released first. The curved structure would not pierce or snag the skirt, so it is allowable for the skirt to extend axially beyond the distal end of the stent to be released first in such a way that a peripheral leakage with higher profile and larger volume may be formed by the longer skirt, thereby improving the sealing effect.

Preferably, at least a portion of the skirt is fixed on the stent.

The term fixed referred to here is relative to the term floating mentioned above. It means that at least a portion of the skirt remains in a fixed position relative to the stent and is free of influence of external factors such as blood flow, which functions to control the position of the resulting peripheral leakage occluder.

Preferably, a portion of the skirt in the axial direction is configured as a fixing band, which is stitched on the stent.

The skirt may be fixed on the stent in a known manner by means of which the valve can be fixed on the stent, such as stitching. In order to ensure the fixation of the skirt on the stent, the skirt is usually stitched for a perimeter of the stent.

Optionally, the fixing band is stitched continuously or discontinuously in a circumferential direction.

The expression stitching continuously means that the stitch line threads through the stent and the skirt repeatedly with dense stitch points. The expression stitching discontinuously means that fewer stitching portions are provided, for example, with 3 to 10 stitching portions for a perimeter of the stent.

Preferably, in the case of stitching discontinuously, the stitching portions are evenly arranged in the circumferential direction, with force evenly applied and stress concentration avoided.

Preferably, the stitch course of the fixing band extends in the circumferential direction, or undulates in the axial direction while extending in the circumferential direction.

Undulating in the axial direction may depend on the structure of the stent or the structure of the skirt. For example, the fixing band is located on the edge of the skirt, with an non-smooth edge and thus having an undulated configuration. The strength of the connection between the skirt and the stent may also be considered.

Preferably, the stent has a meshed structure with grids, and the fixing band is fixed on the stent through a stitch line stitching on the edge of the grids.

In this solution, the stitch line extends along the grids according to the structure of the meshed stent to ensure the strength of the connection, which can avoid loosening after the release or during loading into the delivery system under a large friction.

Optionally, there is one or more fixing bands arranged in the axial direction.

The skirt is fixed to the stent only at the fixing band, and the remaining portion of the skirt is movable relative to the stent. In particular, at least a portion of the skirt is movable and foldable axially. In the case that there is only a single fixing band, the remaining portion of the skirt floats around the outer periphery of the stent.

Preferably, there is a single fixing band located at the middle portion or an end of the skirt in the axial direction. In the case that there is only a single fixing band, the larger portion of the skirt is a floating section and thus there will be a larger portion which is stackable in the axial direction. The fixing band is provided adaptively at the desired position of the peripheral leakage occluder, and the remaining floating section will move towards the fixing band during the axial stacking.

Preferably, at least one section of the skirt in the axial direction is configured as a floating section around the outer periphery of the stent, and the floating section is folded axially in the stacked configuration of the skirt. Both axial sides of the floating section are configured as fixing bands. Alternatively, one axial side of the floating section is configured as a fixing band, and the other axial side of the floating section is floatable.

For example, the top edge of the skirt is fixed on the outer periphery of the stent, and the lower section of the skirt floats around the outer periphery of the stent. Alternatively, the bottom edge of the skirt is fixed on the outer periphery of the stent, and the upper section of the skirt floats around the outer periphery of the stent.

Preferably, a proximal end of the skirt which is to be released later is fixed on the stent, and a distal end of the skirt which is to be released first floats around the outer periphery of the stent.

Alternatively, a distal end of the skirt which is to be released first is fixed on the stent, and a proximal end of the skirt which is to be released later floats around the outer periphery of the stent.

The distal end of the skirt which is to be released first is provided in a floating manner and will be accompanied by axial stacking during the release, which facilitates the coordinative guidance of the stent and the blood flow.

In order to facilitate the loading of the stent in a compressed configuration into the delivery system, such as into a sheath, it is preferable to load the side with the fixing band first, and then load the floating side, which makes the loading process smoother, otherwise the skirt may be folded during loading, and the radial dimension thereof may increase, thereby reducing compliance thereof.

Since the loading and the release are generally opposite processes, loading the side with the fixing band first also means that the proximal side of the skirt to be released later is fixed on the stent.

Preferably, during release of the stent, at least a part of the skirt constrains the stent, and the skirt is driven to be pulled axially with the stent further released.

The release of the stent is developed gradually. During this process, it is necessary for the outer periphery of the stent to contact the skirt and produce an expanding force, so that the skirt can be pulled axially.

Preferably, before the stent is released, the skirt in the unfolded configuration has a folded structure in a circumferential direction.

Since the stent before being released has a low profile, the skirt may be attached to the outer periphery of the stent in a relatively flat manner due to the folded structure in the circumferential direction. After the stent is released, the circumferentially folded structure is unfolded due to the radial expanding of the stent.

Optionally, before the stent is released, the skirt in the unfolded configuration is generally unfolded in a single layer along the axial direction of the stent, or has a pleated structure.

Extending in a single layer contributes to reducing the radial dimension so as to facilitate the loading and delivery. The pleated structure occurs mainly due to the fixing bands provided at both axial ends of the floating section, so it cannot be unfolded in a single layer. However, the pleated structure facilitates the control of the position of the peripheral leakage occluder, and may also form a double-layered structure. The peripheral leakage occluder may be further expanded radially by filling with filler or blood into the double-layered structure, thereby improving the sealing effect. In order to solve the problem of the increased radial dimension, the shape of the stent may be further improved, such as by providing a meshed structure with grids provided more sparsely to synergistically reduce the radial dimension.

Preferably, the stent is provided with a valve and/or a coverage membrane.

As further preferred, the skirt and the valve and/or the coverage membrane are made of same material.

The stent may be provided with a valve and/or a coverage membrane according to its particular application (i.e., the lesion sites). The skirt has to be capable of being folded and stacked, so the skirt is made of flexible material and is at least axially deformable. Various typical valves, such as porcine pericardium or the like, may meet this requirement. In addition, making the skirt with the same material as the valve can omit certain necessary processes such as verifying the biological nature of the material, as the material of the valve is already well known, thereby facilitating the promotion and implementation of the stent apparatus.

Preferably, during the operation of the stent, a side wall of the stent faces a branch blood vessel, and the skirt in the stacked configuration is provided to avoid the branch vessel in an axial position.

For example, there are multiple branch vessels at the aortic arch, so the peripheral leakage occluder having a stacked skirt should be provided to avoid the branch vessels.

Preferably, during the operation of the stent, the skirt in the stacked configuration avoids a channel formed in the stent in an axial position for allowing blood to smoothly flow therethrough.

Similarly, even if there is no clear branch vessel, some portion of the stent must be hollow to allow blood to smoothly flow therethrough; in this condition, the peripheral leakage occluder with the stacked skirt should be provided to avoid the hollow channel. Taking the aortic valve stent as an example, the peripheral leakage occluder should be located upstream of the blood flow relative to the valve. Therefore, the skirt is generally arranged closer to the blood inflow end of the stent than the valve. The axial position of the skirt in the unfolded configuration affects the position of the peripheral leakage occluder which is formed by axially folding the skirt.

Preferably, a first skirt and a second skirt are arranged one above the other in the axial direction, and the first skirt in the stacked configuration forms a first peripheral leakage occluder and the second skirt in the stacked configuration forms a second peripheral leakage occluder.

The arrangement of two peripheral leakage occluders not only solves the problem of the limited axial fold of a single skirt, but also provides a better sealing effect on the peripheral leakage in practice.

However, if there is provided too many skirts, the problem of insufficient radial expansion for an individual peripheral leakage occluder will arise.

Optionally, each of the two skirts is transformed independently from the unfolded configuration into the stacked configuration in the same or different driving techniques.

There are various driving techniques and different influence factors for the folding of the skirt. Different skirts are not strictly required to be released and stacked in the same technique, but may be driven to fold in different cooperation modes according to the respective positions of the skirts.

Preferably, the two peripheral leakage occluders are spaced from each other.

The skirts being folded are generally moved towards their respective fixing bands. Therefore, if two fixing bands are too close to each other, the first and second peripheral leakage occluders formed by the two skirts may get too close to each other. In contrast, if the fixing bands of the two skirts are spaced from each other, for example, each of the two skirts is provided with a fixing band at the respective top edge, then the resulting first and second peripheral leakage occluders will move towards the top edges of the respective skirts, with intervals formed therebetween.

The arrangement of the two spaced peripheral leakage occluders can achieve double sealing. If there is only a single occluder, the sealing effect would be affected once a defect occurs.

Preferably, in the unfolded configuration of the skirt, the stent has flared driving structures at positions corresponding to both of the skirts.

In order to facilitate the smooth transformation of the skirts into the stacking configurations, the flared driving structures may be provided at the positions of the stent corresponding to both of the skirts. The flared driving structures corresponding to the two skirts may taper in the same or different ways. The flared driving structures corresponding to the two skirts may extend continuously to each other or be connected to each other. Alternatively, the flared driving structures may be spaced from each other, that is, the section of the stent between the two flared driving structures is a straight section.

Preferably, the first peripheral leakage occluder is arranged closer to the top of the stent than the second peripheral leakage occluder, and in the unfolded configurations of the two skirts, the axial length of the first skirt which is configured to form the first peripheral leakage occluder has an axial length of 1.5 to 3 times to the axial length of the second skirt which is configured to form the second peripheral leakage occluder.

Since the skirt closer to the top of the stent is longer, after being stacked, the first peripheral leakage occluder has a larger cross section than the second peripheral leakage occluder. That is, after being stacked, the first peripheral leakage occluder at the top has a higher profile and the peripheral leakage occluder at the bottom has a lower profile.

Preferably, in the unfolded configurations of the two skirts, the bottom of the first skirt which is configured to form the first peripheral leakage occluder extends to the top of the second skirt which is configured to form the second peripheral leakage occluder, without overlapping one another.

The two skirts in the unfolded configurations are arranged end to end, which not only maximizes the advantages of the sufficient axial lengths thereof, but also avoids an increased radial thickness caused by overlap of the two skirts, thereby ensuring smooth loading of the stent.

Preferably, one side of the skirt is connected to the side wall of the stent, and the other side is connected to the end of the stent. The stent is further provided with a coverage membrane attached to the stent, which extends to the end of the stent where the stent is connected to the skirt.

In other words, both the skirt and the coverage membrane are connected to the same axial side of the stent. The skirt and the coverage membrane may be separately formed or integrally formed as a single piece. The coverage membrane may be either an internal coverage membrane or an external coverage membrane. In the case of the integrally formed structure, the skirt and the coverage membrane are made of the same material. In addition, it is required for the inner coverage membrane inside the stent to extend to the end of the stent, and then turn outwards to form the skirt. In this situation, the integrally formed structure can simplify the cutting process during stitching and maintain the integrity of the stent apparatus.

Preferably, the coverage membrane is attached to the inner wall of the stent, extends to the end (one axial end) of the stent, and then turns outwardly to form the skirt.

Preferably, the stent is further provided with a valve.

Preferably, the skirt is thickened radially in the unfolded or stacked configuration.

An annular protrusion protruding radially may be formed around the outer periphery of the stent by radial thickening, which functions to fill the gap between the stent and the inner wall of the blood vessel, fix the stent, reduce perivalvular leakage and prevent peripheral back flow.

The course of the thickness may follow one or more units; within each unit, the thickness gradually increases from bottom to top, and then decreases gradually. The units may be arranged continuously or discontinuously and the one or more units may have the same or different configurations.

Preferably, the radial thickening may be achieved by a self-folding structure of the skirt.

The folding structure includes at least one of the following techniques: folding circumferentially; folding axially; and folding radially.

The self-folding of the skirt may be achieved by a combination of the above techniques, for example, a spiral structure, which may be regarded as being formed by folding axially and radially. It is obvious that the above techniques are not exhaustive. In practice, there may also be more complicated or irregular folding structures, however, in any event, at least a radial expansion is formed.

In order to maintain the shape of the folding structure, as preferred, a pulling string is provided through the folded structure, which will be further described below.

As further preferred, the folding structure is formed by: the skirt simultaneously extending upwardly from the end of the stent (one axial end where the skirt is connected to the inner coverage membrane) and folding radially, to the top edge of the peripheral leakage occluder, and then turning outwardly and extending downwardly to the bottom edge of the peripheral leakage occluder.

As further preferred, the folding structure is formed by: the skirt simultaneously extending upwardly from the end of the stent and folding radially, to the top edge of the peripheral leakage occluder, and then turning inwardly and attaching with the outer wall of the stent.

Due to the limited thickness of the material, it may be radially thickened by folding itself outwardly or by filling with filler.

Preferably, the skirt itself has a double-layered structure, or a double-layered structure may be formed between the skirt and the inner coverage membrane. The double-layered structure is filled with filler to increase the radial thickness.

Preferably, the filler is made of water-absorbing expansion material. The present invention may adopt a known water-absorbing expansion material. In the prior art, a peripheral leakage occluder made of water-absorbing expansion material has been developed, however, there is still a risk of partial damage and falling-off for such a peripheral leakage occluder.

Preferably, the pulling string which serves to work on the floating section includes one or more pulling units. Each pulling unit includes at least two threading ends interacting with the skirt, and at least one force exerting portion is formed by at least a part of the pulling unit between the two threading ends and connected to the skirt. The pulling string works on the floating section, while it is not directly connected to the stent. Therefore, the force exerting portion is pulled by the relative circumferential displacement of the two threading ends of the pulling unit.

During release, the stent will be generally expanded, thereby pulling the skirt. Before being released, the skirt is folded circumferentially, and it will be unfolded after being released. The two threading ends of the pulling unit acting with the skirt simultaneously move away from each other and pull the force exerting portion to get the skirt to be folded axially.

Taking the deformation mechanism of a triangle as an example, the skirt portion between the two threading ends may be regarded as a third side, the distance of which is changeable, and the force exerting portion may be regarded as a vertex which is axially movable or at least has a movement component in the axial direction. The vertex moves towards the third side during the release of the stent.

The first side of the triangle may be regarded as locating between one of the threading ends and the force exerting portion, and the second side of the triangle may be regarded as locating between the other threading end and the force exerting portion.

Ignoring the elastic deformation of the pulling string itself, the overall length of the first and second sides is substantially fixed. If the force exerting portion is fixed to the skirt, both the length of the first side and the length of the second side are fixed. If the force exerting portion movably threads through the skirt, the respective lengths of the first and second sides may change, while the overall length is fixed.

Although the shape of the triangle may change in various manners or have many deviations, the mechanisms are generally the same, i.e., converting a distance variation between the two points that move relative to each other in the circumferential direction of the skirt during the release of the stent into an axial movement of the third point. This is also the main distinction between the driving mechanism of the present invention and that of the prior art. In the present invention, the floating section is driven to be stacked utilizing the deformation of the pulling string and the stent itself.

Optionally, the force exerting portion is fixed on the skirt or movably threads through the skirt.

The force exerting portion functions to pull the skirt to move axially. One pulling unit may be connected to the skirt via one or more connection points, the one or more connection points may be fixed on or movably thread through the skirt. The skirt is provided with threading holes for the pulling string to pass through.

In the case of movable threading, the force exerting portion is not a fixed portion of the pulling string. The force exerting portion which contacts the skirt during the movement is changeable, that is, the pulling string contacts with the skirt at different positions. Therefore, the force exerting portion is a dynamically changeable portion on the pulling string and referred to as the portion currently contacting the skirt.

Preferably, the at least one force exerting portion comprises a plurality of force exerting portions which are distributed continuously or discontinuously with intervals therebetween; wherein, when the force exerting portions of the pulling string are distributed discontinuously, force is transmitted across the intervals through the skirt.

One or more force exerting portions may be provided in one pulling unit. The force exerting portions distributed continuously or discontinuously indicates that the pulling strings between the force exerting portions are continuous or discontinuous. In the case where the pulling strings between the force exerting portions are discontinuous, the force may be transmitted though the material of the skirt.

The discontinuous pulling strings can be considered as the pulling unit including multiple pulling strings that are not connected directly. In this case, the pulling of the skirt requires the cooperation of multiple pulling strings, and it is impossible to pull the skirt via a single pulling string.

Preferably, the skirt is provided with one or more threading holes, and the at least one force exerting portion movably threads through the one or more the threading holes; and at least one of the one or more threading holes is arranged offset from a line connecting the two threading ends.

During the release of the stent, the two threading ends move away from each other. If all the threading holes are arranged on the line connecting the two threading ends, the relative movement of the two threading ends would not drive the skirt to move, or the axial pull of the skirt is not significant. The extension of the pulling string may be flexibly controlled through the threading holes, which facilitate the cooperation among the multiple pulling units.

Compared with the technique of the force exerting portion being fixed on the skirt and thus pulling the skirt, the technique of the force exerting portion movably threading through the skirt can adjust the position deviation of the skirt resulting from pulling in the circumferential direction, preventing the sealing effect of the peripheral leakage occluder from being weakened due to undesired deformation such as twist.

Preferably, the force exerting portion is located between the two threading ends along an extension direction of the pulling string.

During the release of the stent, the two threading ends move away from each other in the circumferential direction and thus pull the force exerting portion together to make it move axially or at least have a movement component in the axial direction, so as to pull the skirt along two inclined directions.

Preferably, the two threading ends are opposite to each other and located at the same level along the axial direction.

In this case, a maximum relative movement in the circumferential direction can be obtained, otherwise there will be a component in the inclined direction, which will weaken or lower the pulling performance.

Preferably, the pulling string of each pulling unit is configured in a wave-like manner having one or more waves and each wave has a triangle, trapezoid, rectangle or arc shape.

Even within the simplest pulling unit, the force exerting portion and the two threading ends of the pulling unit form an undulated configuration. The pulling unit may include one wave as being a simplest configuration, or more repeated waves as being a complicated configuration. For example, in the case that there is a plurality of threading holes, the configuration of the pulling unit will be complicated. The common and simple wave shapes are triangle, rectangle, or trapezoid, etc., which facilitate the threading with less interference among different portions of the pulling string.

Since the stent being released expands radially and also shortens axially, both circumferential span and axial length of the pulling unit change during release of the stent. In general, the circumferential span and the axial length change cooperatively.

Preferably, the driving portion extends around the stent for at least a perimeter of the stent, and two ends of the driving portion join together at the force exerting portion.

Preferably, the two ends of the driving portion respectively extend along two sides of a V-shaped course and join together at the force exerting portion. The driving portion extends around the outer periphery of the stent. During the deformation of the stent, the driving portion is expanded and then the vertex of the V-shaped course is pulled to move axially.

One of the driving portion and the force exerting portion is located on the side of the skirt to be released first, and the other is located on the side of the skirt to be released later.

Preferably, the driving portion is located on the side of the skirt to be released first, and the force exerting portion is located on the side of the skirt to be released later.

The side of the stent to be released first expands first, then the driving portion deforms and drives the connected portion of the skirt to get closer to the force exerting portion and become stacked, wherein the force exerting portion serves as a fixed point for pulling. Conversely, if the force exerting portion is released first, there will be insufficient force to pull the portion of the skirt connected to the force exerting portion for becoming stacked, as the driving portion is still in a compressed configuration in the sheath.

Preferably, the pulling string undulates in the axial direction of the stent while extending in the circumferential direction of the stent and thus forms a wave-like configuration, and the wave shape of the pulling string is changed when the pulling string is driven by the deformation of the stent during release so as to pull the skirt into the stacked configuration.

Although the pulling string is not directly connected to the stent, it still extends around the outer periphery of the stent. When the stent is radially expanded, an enclosed area of the pulling string will be enlarged, resulting in a changed wave shape. The waves may have various shapes, and the shapes of the waves may be the same or different.

Preferably, the waves of the pulling string are distributed periodically, and the shape of the one or more waves within each cycle may be one or any combination of a triangle, a rectangle and a trapezoid.

Preferably, the skirt is provided with a first set of threading holes and a second set of threading holes, with each set of threading holes comprising a plurality of threading holes arranged in a circumferential direction, the two sets of threading holes are arranged one above the other in the axial direction, and the pulling string alternatively threads through the first set of threading holes and the second set of threading holes and forms the wave-like configuration.

Preferably, the pulling string alternatively threads into and out of the surface of the skirt.

Preferably, the two sets of threading holes have the same number of threading holes and the threading holes of the first set are arranged offset from the threading holes of the second set.

Preferably, the skirt is provided with a plurality of cutting areas at at least one axial side thereof which are arranged in the circumferential direction.

Before operation, it is required for the prosthetic heart valve replacement device to be compressed radially and loaded in a delivery system, such as loaded in a sheath, and then delivered into the human body via blood vessels for release. In order to improve the compliance and the capacity in the human body and reduce the friction on the vessel wall, it is preferred for the entire device to have a smaller diameter after loading and before release. During the loading of the stent being radially compressed, the ends of the skirt which surrounds the outer periphery of the stent will be gathered and expanded, and it is difficult to regularly flatten the ends of the skirt to conform around the outer periphery of the stent. On one hand, it is difficult for the skirt to enter into the sheath. On the other hand, the skirt may be damaged or even fall off the stent at the end of the loading, as the resistance of the end of the skirt being gathered into the sheath is too large. In order to solve the aforementioned problems caused by the radial gathering and the reduction in the size during loading, the skirt of the present invention is partially cut at positions adjacent to the axial ends thereof to reduce the thickness thereof when being gathered, thereby facilitating the loading and delivery.

Preferably, the cutting areas are hollow structures.

The hollow structures, as one type of the cutting areas, may maintain the integrity of the skirt, and contributes to standardized cutting shapes by processes such as punching or laser cutting or the like, facilitating mass production by controlling errors.

Preferably, within each cutting area, the hollow structure comprises a plurality of through holes arranged along the axial direction of the stent.

The hollow structure comprising through holes arranged sequentially leaves connection portions between the through holes, which is beneficial to the overall shaping of the peripheral leakage occluder and maintains the necessary pulling effect between different areas.

The shape of the through holes may be varied, such as circular, elliptical, polygonal, or crescent-shaped or the like. The shapes of the through holes in the same row may be the same or different.

Preferably, different cutting areas have the same hollow structure.

The design of the same hollow structure allows for mass production. In addition, the force on the skirt in the circumferential direction can distribute more evenly, and the resulting annularly stacked configuration has a more uniform profile.

As another preferred embodiment, a stacked configuration with an approximate uniform profile may also be obtained if the size of each hollow area is small enough.

The plurality of cutting areas arranged in the circumferential direction mainly means that the cutting areas are distributed along the whole circumference. Although the cutting areas may be spaced with a certain distance, they are not concentrated in a particular local area in the circumferential direction.

A plurality of cutting areas may or may not have clear boundaries. For example, in the case of a plurality of through holes that are densely arranged, the through holes may be distributed randomly or in a dispersed manner, so it is not necessary for the cutting areas to have clear boundaries. Even in the case of clearly regular structural units, the boundary between the units may be the generatrix of the skirt, or may be distributed in a certain angle relative to the generatrix, such as being spirally distributed.

Preferably, among the through holes of the same cutting area, the closer to the corresponding side edge of the skirt, the larger the size of the through hole.

The cutting area is located at the top or bottom of the skirt. Taking the cutting area at the bottom as an example, the closer to the bottom edge of the skirt, the larger the size of the through hole. In other words, the closer to the edge of the skirt, the smaller the area of the remaining portion of the skirt, which facilitates the attachment of the skirt to the outer periphery of the stent and the loading of the stent apparatus.

Preferably, the inner edge of the through hole is smoothly curved.

The strength of the skirt is limited. If there are clear corners on the inner edge after forming the through hole, there will be a localized stress concentration during the deformation of the skirt, resulting in the risk of tearing. The smoothly curved inner edge may greatly reduce such risk and improve the safety in use.

Preferably, at least one axial side of the skirt is configured as a tooth-shaped structure having a plurality of teeth arranged in the circumferential direction, with one of the cutting areas between adjacent teeth.

As another preferred cutting technique, in the present invention, the skirt is cut at least at one axial side thereof, and the remaining portions at the edge are tooth-shaped with teeth distributed circumferentially. In this case, the skirt being radially compressed will have a smaller outer diameter at the cut end thereof, which facilitates the loading of the stent apparatus.

Moreover, by using the tooth-shaped cutting structure, the edge of the skirt is opened, which can avoid intertwining or interference of the skirt with the stent or the pulling string, facilitating the release of the skirt.

Optionally, the teeth of the tooth-shaped structure have the same or different shapes.

Optionally, the shape of each tooth is one or any combination of a triangle, a rectangle, a trapezoid, and a semicircle.

Within the tooth-shaped structure, the shapes of the teeth are not strictly limited. The tooth-shaped structure may also be combined with the hollow structure such that the remaining area at the end of the skirt may be reduced. The configuration of the tooth includes both the geometrical shape and the size. For example, all the teeth may be triangular teeth, while they are distinguished as large teeth and small teeth and arranged in an alternating manner. Alternatively, rectangular teeth and triangular teeth may be provided and arranged in an alternating manner.

Preferably, the teeth have the same configuration and are evenly arranged in the circumferential direction.

The teeth with the same configuration mean that they are evenly arranged in the circumferential direction. Although both of the axial ends of the skirt may have tooth-shaped structures, the tooth-shaped structures at both of the axial ends may be the same or different. The even distribution of the teeth at the same end of the skirt renders the skirt subject to force distributed evenly in the circumferential direction, and be well adaptable in the circumferential direction, without special positioning means.

As further preferred, both sides of the triangle tooth are inclined relative to the axial direction of the stent. Alternatively, one side is parallel to the axial direction of the stent, and the other side is inclined relative to the axial direction of the stent.

Preferably, before the stent is released, the side of the skirt to be released first extends beyond the stent in the axial direction, and it is the tooth-shaped structure that extends beyond the stent.

In order to obtain a peripheral leakage occluder with sufficient volume, the skirt should have sufficient axial length. However, if the skirt is so long, especially before the stent is released, that the side of the skirt to be released first extends beyond the stent in the axial direction, the stent will be released after the skirt and may roll outwardly and snag, or even pierce the inner wall of the skirt, preventing the skirt from being folded axially. This situation can be avoided if the side of the skirt adopts the tooth-shaped structure.

The portion of the skirt that extends beyond the stent is released before the stent. The stent during release is able to smoothly turn out from the cutting areas. Even if some teeth of the skirt may cover the stent, they will adaptively avoid the stent as the teeth have a high degree of freedom. As further preferred, the root of the teeth of the tooth-shaped structure does not extend beyond the bottom end of the stent.

If the root of the teeth slightly extends beyond the edge of the corresponding side of the stent, the above risks still exist. Taking the bottom side of the stent to be released first as an example, the top edge of the skirt is fixed on the stent. In the unfolded configuration, the bottom side of the skirt extends axially beyond the bottom edge of the stent, and the portion of the skirt that extends beyond the bottom of the stent is the tooth-shaped structure.

Preferably, the side of the skirt with the cutting areas floats around the outer periphery of the stent, and a limiting string may be provided between the floating side of the skirt and the stent for limiting the maximum axial movement of the floating side of the skirt.

Preferably, the floating side of the skirt is configured as a tooth-shaped structure having a plurality of teeth arranged in the circumferential direction, with one of the cutting areas between adjacent teeth. The limiting string is connected at the top tip of each tooth.

The movement of the teeth may be restrained and limited by means of the pulling line, especially in the case of a long tooth-shaped structure. For example, the bottom of the skirt may have the tooth-shaped structure and floats around the outer periphery of the stent, and the limiting string is provided between the top tips of the teeth and the stent for limiting the maximum axial movement of the floating side of the skirt.

Similar to the tooth-shaped structure, the hollow structure may also be provided with a limiting string. In addition, even if the skirt does not have cutting areas, the limiting string may also be applied to control the axial movement of the skirt as required. The limiting string may also be connected at the axial middle portion of the skirt, and affect the shaping and configuration of the peripheral leakage occluder to a certain extent.

Preferably, the side of the skirt with the cutting areas is fixed on the outer periphery of the stent.

The side of the skirt with the cutting areas may also be fixed on the stent, which usually serves as the side of the skirt to be released later. The loading process is just reversed, with the cutting areas fixed entering into the sheath first. The cutting areas may be in the form of a hollow structure or cutting structure at the edge.

Preferably, one axial side of the skirt is configured as a tooth-shaped structure having a plurality of teeth arranged in the circumferential direction, with one of the cutting areas between adjacent teeth.

Within the tooth-shaped structure, a vertex of each tooth is fixed on the stent, or the vertex and edges of each tooth are fixed on the stent.

The tooth-shaped structure is formed by cutting materials at the edge, which may be fixed only at the vertices of the teeth. In this situation, the fixing band is stitched discontinuously with a plurality of stitching portions having intervals.

If the edges of the teeth are also stitched on the stent, the fixing band is fixed in a continuously stitched manner. Compared to the technique of stitching discontinuously with intervals, the technique of stitching continuously may bring a stronger connection strength, but result in additional radial expansion to a certain extent.

Preferably, the stent has a meshed structure having a plurality of grids, and the shape of teeth corresponds to that of the grids at a corresponding portion of the stent.

A tooth having the same shape as the grid further facilitates the stitching, especially to the continuous and dense stitching, which, on one hand, avoids unnecessary parts of the skirt, and on the other hand, ensures the sufficient attachment for the edges of the teeth on the meshed stent.

Preferably, the skirt is provided with an annular blocking pocket at an inflow side of back-flow blood for receiving the back-flow blood from peripheral leakage, and the blocking pocket has at least one inlet for allowing back-flow blood to flow in, by means of which the blocking pocket is self-expandable to prevent further regurgitation.

The blocking pocket is also made of flexible material, which may be optionally made of the same material as the skirt or even be a part of the skirt. The blocking pocket is fixed to the outer periphery of the stent by stitching, and has a double-layered structure, via which it may be filled with blood and thus be expanded radially.

The inlet for allowing back-flow blood to flow in faces towards the annulus, i.e., the top side of the stent, and functions to receive the back-flow blood from peripheral leakage. After the blood flows into the blocking pocket, the blocking pocket self-expands radially to abut against the annulus to further prevent regurgitation.

Preferably, after the stent is released, the peripheral leakage occluder is located at the side of the blocking pocket facing the inflow side of the normal blood flow of the stent (the peripheral leakage occluder and the blocking pocket are arranged on the stent in sequence along the direction of the normal blood flow), and the peripheral leakage occluder and the blocking pocket abut against each other.

The blocking pocket may cooperate with the peripheral leakage occluder formed by the skirt, wherein the blocking pocket is arranged closer to the annulus, and the peripheral leakage occluder which is located upstream of the normal blood flow supports the blocking pocket, and works cooperatively therewith.

Preferably, the side of the blocking pocket facing away from the inflow side of the back-flow blood is closed, and the side facing the inflow side of the back-flow blood is provided with a plurality of stitching portions fixed to the stent. The stitching portions are spaced from each other with an inlet between two adjacent stitching portions.

Preferably, a plurality of inlets for allowing back-flow blood to flow therein are provided and are evenly arranged in the circumferential direction.

A plurality of inlets for allowing back-flow blood to flow therein are provided in the circumferential direction, which are formed by stitching with intervals, that is, the areas that are not closed by stitching serve as the inlets for allowing back-flow blood to flow therein. The plurality of inlets for allowing back-flow blood to flow therein enable the blocking pocket to expand uniformly with a significant receiving performance.

Preferably, the blocking pocket is formed separately; or formed integrally with the skirt as a single piece.

Alternatively, a portion of the blocking pocket is formed by the material of the skirt; or a portion of the blocking pocket is formed by the material of the coverage membrane inside the stent.

Alternatively, a portion of the blocking pocket is formed by the material of the skirt, and the other portion of the blocking pocket is formed by the material of the coverage membrane inside the stent.

The blocking pocket may be formed in the following techniques:

1. The blocking pocket is separately provided relative to the material of the skirt, and may be provided as a double-layered structure. For example, the inner and outer layers may be formed as a single piece, which are connected by a bend at the bottom side. Alternatively, the inner and outer layers are separately formed, which are connected and sealed by stitching the bottoms together. At the top of the blocking pocket, the top edge of the inner layer of the blocking pocket is generally continuously stitched on the outer periphery of the stent by a dense stitching, and the outer layer is stitched on the stent discontinuously with intervals to form the plurality of inlets for allowing back-flow blood to flow therein.

2. The blocking pocket and the skirt are integrally formed as a single piece, in which the blocking pocket is formed by axially folding the top of the skirt, and cutting at appropriate positions of the folded portion of the skirt to form the plurality of inlets for allowing back-flow blood to flow therein.

3. A portion of the blocking pocket is formed by the material of the skirt. The blocking pocket is provided as a double-layered structure including an inner layer and an outer layer. The inner layer and the outer layer are closed at the bottom, and the plurality of inlets for allowing back-flow blood to flow therein are formed at the top. Either one of the inner and outer layers may be formed by the material of the skirt.

For example, the inner layer of the blocking pocket is integrally formed with the skirt as a single piece, and only the outer layer is additionally provided and stitched on the periphery of the skirt.

Alternatively, the outer layer of the blocking pocket is integrally formed with the skirt as a single piece. An inner layer is first provided and stitched, and then the top of the skirt is attached to the outer periphery of the inner layer and thus forms the outer layer of the blocking pocket.

4. The coverage membrane inside the inner wall of the stent simultaneously serves as the inner layer of the blocking pocket, and an outer layer is provided to cover the outer periphery of the stent.

5. The coverage membrane inside the inner wall of the stent simultaneously serves as the inner layer of the blocking pocket, and the top of the skirt simultaneously serves as the outer layer of the blocking pocket.

Preferably, the skirt is provided with an annular pushing pocket at an inflow side of normal blood flow for facilitating the skirt to transform into the stacked configuration, and the pushing pocket has at least one inlet for allowing blood to flow in, by means of which the pushing pocket is self-expandable to push the skirt.

The pushing pocket is made of flexible material, which may be made of the same material as the skirt or even be a part of the skirt. The pushing pocket is fixed to the outer periphery of the stent by stitching, and has a double-layered structure, via which it may be filled with blood and thus be expanded radially.

The inlet for allowing normal blood flow to flow in faces away from the annulus, i.e., facing towards the normal blood flow, and functions to receive the normal blood flow. After the blood flows into the pushing pocket, the pushing pocket self-expands to assist the skirt to move axially and thus be folded.

Preferably, the bottom edge of the skirt in the unfolded configuration extends beyond the pushing pocket.

The pushing pocket after being expanded contacts and pushes the skirt. If the pushing pocket and the skirt are not in contact, the pushing effect may be unsatisfied. More preferably, an extension portion of the bottom edge of the skirt in the unfolded configuration covers the pushing pocket fully or partially. In this way, the radial expansion of the pushing pocket may be well transmitted to the skirt.

Preferably, one side of the pushing pocket is closed, and the other side is provided with a plurality of stitching portions fixed to the stent. The stitching portions are spaced from each other with an inlet for allowing normal blood to flow in between two adjacent stitching portions.

Preferably, a plurality of inlets for allowing blood to flow in are provided and are evenly arranged in the circumferential direction.

The plurality of inlets for allowing blood to flow in that are arranged in the circumferential direction are formed by stitching with intervals, that is, the areas that are not closed by stitching serve as the inlets for allowing blood to flow in. The plurality of inlets for allowing blood to flow in enable the pushing pocket to expand uniformly with a significant receiving performance.

The pushing pocket is formed separately; or formed integrally with the coverage membrane inside of the stent as a single piece. Alternatively, a portion of the pushing pocket is formed by the material of the coverage membrane inside of the stent.

The pushing pocket may be formed in the following techniques:

1. The pushing pocket is separately provided relative to the material of the skirt. Since the pushing pocket is provided as a double-layered structure, the inner and outer layers may be integrally formed as a single piece, which are connected by a bend at the top side. Alternatively, the inner and outer layers are separately formed, which are connected and sealed by stitching the tops therebetween. At the bottom of the pushing pocket, the top edge of the inner layer of the pushing pocket is generally continuously stitched on the outer periphery of the stent by a dense stitching, and the outer layer is stitched on the stent discontinuously with intervals to form the plurality of inlets for allowing blood to flow in.

2. The pushing pocket and the coverage membrane inside of the stent are integrally formed as a single piece, in which the pushing pocket is formed by turning outwardly and axially folding the coverage membrane inside of the stent, and the inner and outer layers may be stitched together in the technique described above.

3. A portion of the pushing pocket is formed by the material of the coverage membrane inside of the stent. The pushing pocket is provided as a double-layered structure including an inner layer and an outer layer. The inner layer and the outer layer are closed at the top, and the inlets for allowing blood to flow in are formed at the bottom. Either one of the inner and outer layers may be formed by the material of the coverage membrane inside or outside of the stent.

For example, the inner layer of the pushing pocket is integrally formed with the skirt as a single piece, and only the outer layer is additionally provided and stitched on the periphery of the skirt.

Alternatively, the outer layer of the pushing pocket is integrally formed with the skirt as a single piece. An inner layer is first provided and stitched, and then the top of the skirt is attached to the outer periphery of the inner layer and thus forms the outer layer of the pushing pocket. The plurality of inlets for allowing blood to flow in are formed by cutting at appropriate positions.

The present invention also provides a processing method for the stent apparatus with a self-folded skirt, including the steps of:

a. arranging a prepared skirt around an outer periphery of the stent in a released configuration;

b. threading a pulling string through the skirt according to a preset course;

c. pulling the pulling string to drive the skirt to transform into the stacked configuration; and d. fixing ends of the pulling string.

The length of the pulling string is related to the size of the skirt corresponding to the expanded stent, the perimeter of the expanded stent, and the size and number of peripheral leakage occluders. Before the stent is loaded and compressed, the skirt has been stitched on the stent. Since the stent is generally in a released configuration during stitching, the configuration of the skirt after being stitched and before being loaded is basically the same as that of the skirt after the stent is released in the human body, i.e., the stacked configuration of the skirt after the stent is released. Therefore, it may be regarded that the process of stitching the skirt on the stent is a process to predefine the configuration of the skirt. In order to reduce the radial dimension during loading, the predefined skirt is axially unfolded. After the stent is released in the human body, the skirt can be restored to the stacked configuration as predefined.

In order to facilitate the threading of the pulling string, preferably, in a step a, the skirt is flattened around the outer periphery of the stent in the released configuration.

Step a further comprises fixing at least a part of the skirt on the stent.

Step a further comprises stitching the skirt as a cylindrical structure which is closed in the circumferential direction before or after the skirt is surrounded around the outer periphery of the stent.

With respect to the technique for fixing the ends, preferably, in a step d, the pulling string comprises two ends which are connected with each other. Other than being connected with each other, the ends may also be connected by themselves. The nodes of the ends are just to prevent the pulling string from falling off from the skirt, which is not necessary or strictly limited for driving the skirt to transform into the stacked configuration. Similarly, the step d of fixing ends of the pulling string can also be achieved by tying the ends on the stent.

The invention also provides a heart valve, comprising the stent apparatus with a self-folded skirt.

The invention also provides a folding method for a skirt of a stent apparatus at an implantation site of the stent, wherein the stent apparatus is the stent apparatus with a self-folded skirt, and the skirt comprising:

an unfolded configuration loaded in a sheath before the stent is released, in which the skirt is axially unfolded and surrounds an outer periphery of the stent before being released; and a stacked configuration during or after the release of the stent, in which the skirt is folded and stacked in an axial direction of the stent after being released and forms an annular peripheral leakage occluder;

the stent apparatus is further provided with a pulling string that only threads through the skirt, and the pulling string operates in cooperation with radial deformation of the stent during release so as to drive the skirt to transform into the stacked configuration.

The specific structures of the stent apparatus, the skirt and the pulling string involved in the folding method for a skirt may be referred to in the detail disclosures according to the present invention, and will not be repeated here.

The peripheral leakage prevention means provided by the present invention provides an implantable stent that is more suitable with the inner wall of the blood vessels, so that the stent would not be easily migrated and is more stable, with expanded applicable population, lower additional surgical risks, and reduced peripheral leakage, thrombi and other complications. Better hemodynamic performance is provided, the coverage of endothelial cells of the host is enhanced, the probability of occurrence of endocarditis is lowered, and the normal blood supply function of the heart and blood vessels is recovered.

DESCRIPTION OF THE EMBODIMENTS

Figure 1A:
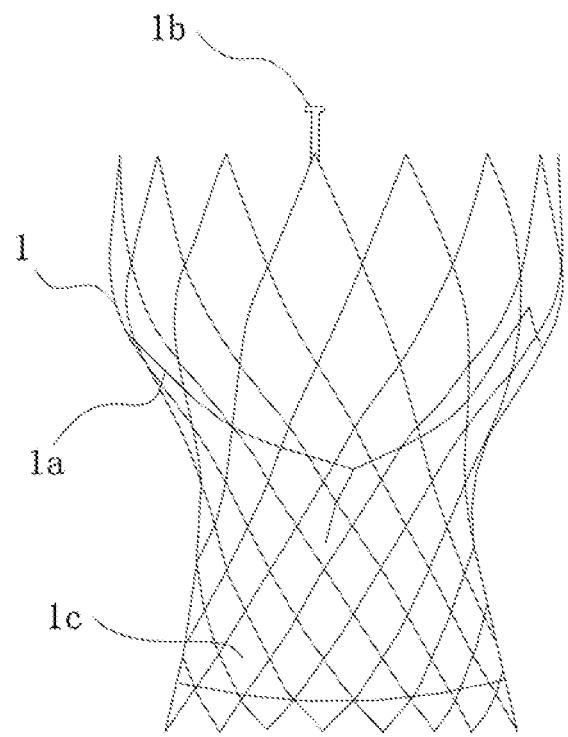
FIG. 1a is a schematic structural view of a traditional aortic stent.

In the stent apparatus for preventing peripheral leakage according to the present invention, the stent may be any known stent in the art. After entering into the body, the distal axial end of the stent is released first, and then a proximal end is to be released later. During release of the stent, any axial end thereof may serve as the distal end, with the other end thereof as the proximal end, which depends on physiological structures of different lesion sites in the human body and operating methods of implantation surgeries. In FIG. 1a, an aortic stent including a stent 1 is taken as an example. The stent 1 is made of material such as nickel-titanium alloy. A fixing ear 1b is provided at the top of the stent (referring to the orientations shown in the figures) for connecting with a delivery system. Depending on the applications and requirements of the stent, a valve 1a or an inner coverage membrane 1c may be provided in the stent. The peripheral leakage referred in the present invention is not strictly limited to the aortic valve, but also may occur in other positions in the human body with similar physiological structures.

Unless otherwise specified, in the figures of the following embodiments: solid rectangular boxes illustrate that the portions of a pulling string there are fixed to the skirt; hollow rectangular boxes illustrate that the portions of the pulling string there are movably threaded through the skirt. The pulling string does not thread through the interior of the stent, but only extends around the outer periphery of the stent. In some embodiments, descriptions of the pulling string or the skirt are omitted, in order to clearly show and highlight the key points. All solutions of embodiments in the present invention are provided with a skirt. In the cases where a pulling string is not specifically indicated as being provided or not, it should be understood that the pulling string may be omitted, or the pulling string may be provided in the same manner as referred to in the other embodiments as required.

First Embodiment

Figure 1B:
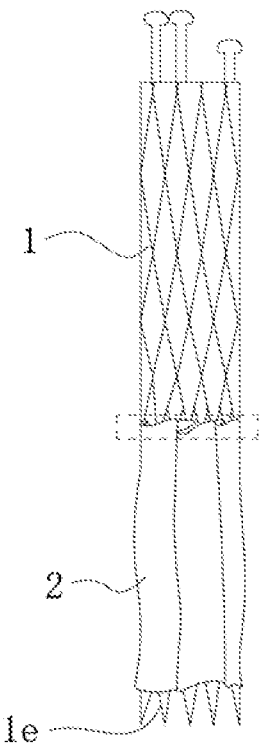
FIG. 1b is a schematic structural view of a stent apparatus according to a first embodiment of the present disclosure, showing a stent thereof before being released.
Figure 1C:
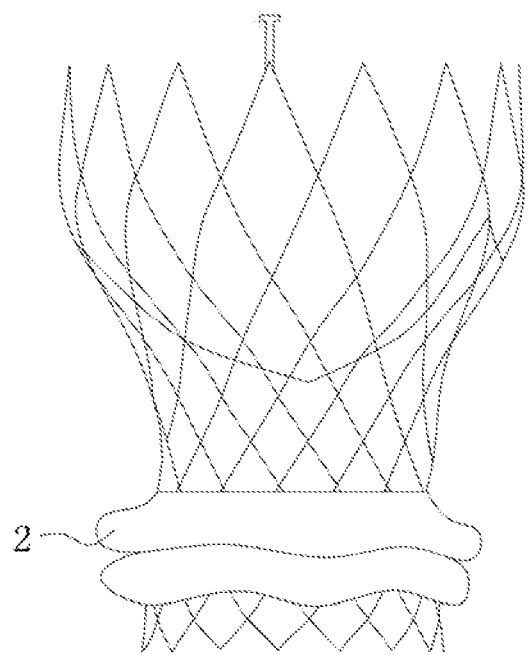
FIG. 1c is a schematic structural view of the stent apparatus according to the first embodiment, showing the stent after being released.

Referring to FIGS. 1b and 1c, the stent apparatus according to the present embodiment includes a stent 1 with a flexible skirt 2 provided on the outer periphery. A pulling string may be provided to thread through the skirt 2, which is, however, not shown in FIGS. 1b and 1c. The pulling string may thread through the skirt in any one of the techniques described in combination with other embodiments. The pulling string operates in cooperation with radial deformation of the stent during release, driving the skirt into a stacked configuration. Before being released, the stent 1 is in a radially compressed configuration. Before implantation, the stent is loaded into a delivery system and generally retains said compressed configuration under the constraint of a sheath, in which case, the skirt is circumferentially folded (shown in the dashed box in FIG. 1b).

Before the stent 1 is released, the skirt 2 is in an unfolded configuration in an axial direction, which is axially unfolded and surrounds the outer periphery of the stent 1. The axial unfolding of the skirt is caused by an inner wall of the sheath which axially drags the skirt during the loading process. In order to improve the compliance of the skirt, a skirt having an outer diameter as small as possible should be used. Further, the skirt is required to be unfolded as much as possible to avoid being folded or overlapped.

During the release of the stent, the expanded stent is gradually constrained by at least a portion of the skirt, and in the mean time, the pulling string axially pulls the skirt to form a peripheral leakage occluder upon further release of the stent.

Valves may be provided in the stent, depending on the practical application; for example, the resulting stent apparatus may serve as a heart valve for preventing perivalvular leakage.

The stent apparatus may serve as a blood vessel stent for preventing peripheral leakage between the stent apparatus and the inner wall of the blood vessel.

Figure 1D:
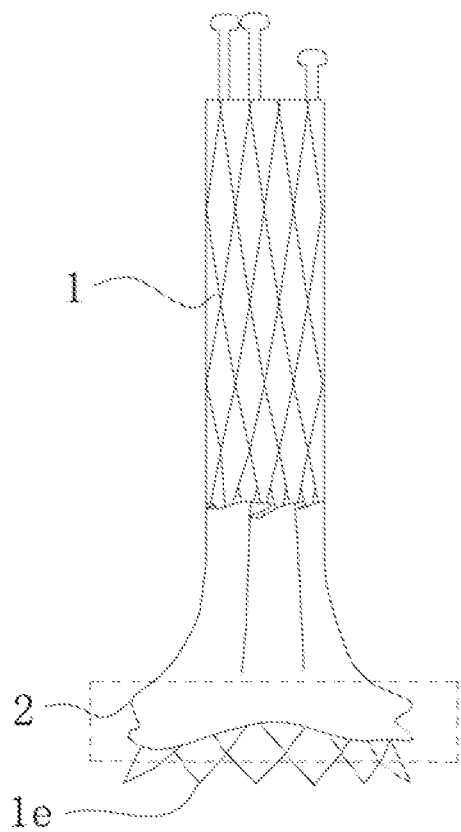
FIG. 1d is a schematic structural view of the stent apparatus according to the first embodiment, showing the stent during release.

FIG. 1d shows the stent 1 in a configuration during release, in which the bottom of the stent 1 is first released from the sheath of the delivery system and begins to expand radially to form a flared configuration, and the bottom of the skirt 2 (shown in the dashed box) is gradually stacked.

The stent 1 expands radially in the human body after being released from the delivery system. The skirt 2 is in a stacked configuration. The stacking of the skirt 2 is cooperative with the deforming of the stent during release. The skirt 2 is folded and stacked in the axial direction of the released stent to form an annular peripheral leakage occluder. The peripheral leakage occluder may reduce the gap between the outer wall of the stent and the inner wall of the body channel, and prevent regurgitation (i.e., the peripheral leakage). The peripheral leakage occluder formed by the skirt 2 is shown in FIG. 1c.

Preferably, the skirt 2 is made of flexible material, such as a porcine pericardium, or a bovine pericardium, or other flexible biocompatible materials, which is configured for constraining the outer periphery of the stent after the stent is released. The skirt is substantially in a cylindrical shape, having a diameter smaller than the outer diameter of the portion of the stent in the released state which the skirt surrounds, such that a constraint force is formed by the skirt onto the stent. During the release of the stent, the stent expands radially and outwardly gradually and takes an intermediate configuration with the flared configuration formed at the distal end that is released first, which may guide the flexible skirt to stack in the axial direction.

FIG. 1c shows a two-layer stacked configuration, which is only used for illustration. The practical application may be more complicated, depending on the size and the material of the skirt, which in any event, does not affect the implementation of the invention, i.e., the skirt stacks axially and expands radially to form a peripheral leakage occluder.

In this embodiment, the stent 1 generally has a meshed structure, and one axial side thereof (bottom end in the figures) is provided with a sharp angled structure 1e. The corresponding side of the skirt 2 (bottom end) does not extend axially beyond the tips of the sharp angled structure 1e before the stent 1 is released. In other words, the sharp angled structure 1e is partially exposed to the outside of the skirt 2. When the stent is being released, the tips of the sharp angled structure 1e located at the distal end which is first released will turn outwardly. If the skirt in the unfolded configuration covers the tips of the sharp angled structure 1e, the tips of the sharp angled structure 1e may snag the inner side of the skirt, which would prevent the skirt from being folded axially.

Figure 1E:
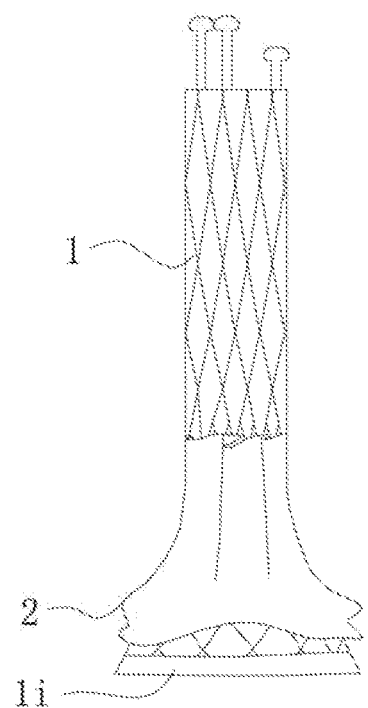
FIG. 1e is a schematic structural view of a stent apparatus with the sharp tips at the bottom end of the stent covered compared to the first embodiment.

Actually, the skirt 2 may extend beyond the tips of the sharp angled structure 1e in the axial direction. In this case, a skirt sleeve ii may be provided and stitched at the bottom end of the stent, as shown in FIG. 1e, which covers the tips of the sharp angled structure to prevent the skirt from being snagged by the tips of the sharp angled structure during the release of the stent, ensuring the stacking of the skirt. Before the stent 1 is released, the skirt 2 in the unfolded configuration has a circumferentially folded structure (shown in the dashed box in FIG. 1b). After the stent 1 is released, the circumferentially folded structure is unfolded due to the radial expanding of the stent. In this embodiment, before the stent 1 is released, the skirt 2 in the unfolded configuration is generally unfolded in a single layer along the axial direction of the stent. The skirt 2 may also have a pleated structure in other embodiments.

In this embodiment, the skirt 2 may generally float around the outer periphery of the stent 1. Alternatively, the top edge of the skirt may be fixed around the outer periphery of the stent by means of stitching.

Second Embodiment

Figure 2A:
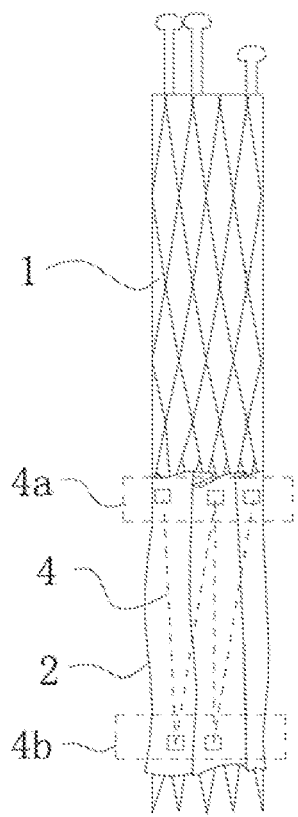
FIG. 2a is a schematic structural view of a stent apparatus according to a second embodiment of the present disclosure, showing a stent thereof before being released.
Figure 2B:
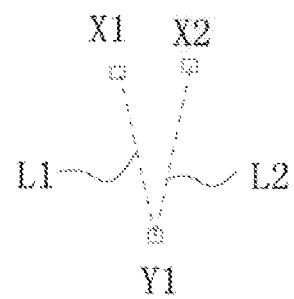
FIG. 2b is a schematic structural view of the stent apparatus according to the second embodiment, showing a pulling unit before being released.
Figure 2C:
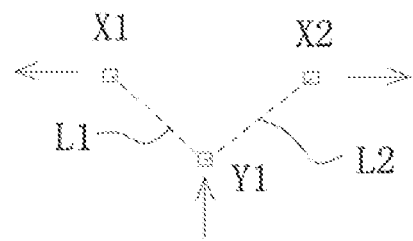
FIG. 2c is a schematic structural view of the stent apparatus according to the second embodiment, showing the pulling unit after being released
Figure 2D:
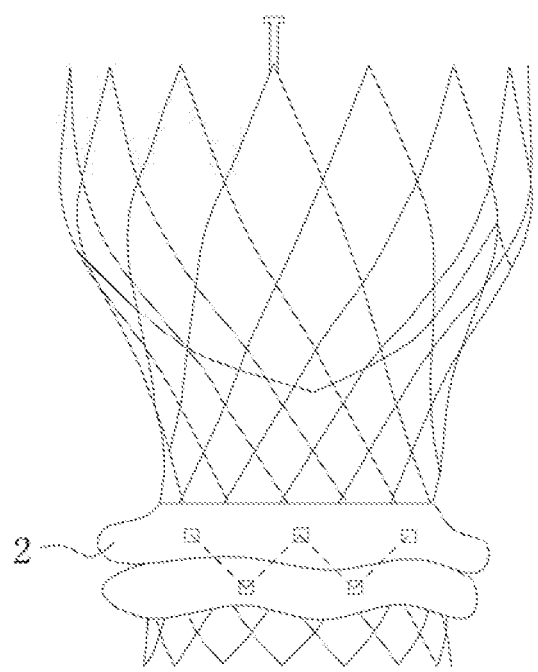
FIG. 2d is a schematic structural view of the stent apparatus according to the second embodiment, showing the stent after being released.

Referring to FIGS. 2a to 2d, in the second embodiment, the outer periphery of the stent 1 is provided with a flexible skirt 2 which may be seen in FIG. 2a. The top edge of the skirt 2 is fixed to the outer periphery of the stent 1. Before the stent 1 is released, the skirt 2 is in an unfolded configuration, which is axially unfolded and surrounds the outer periphery of the stent 1 before release. After the stent 1 is released, the skirt 2 is folded and stacked along the axial direction of the released stent 1 into a stacked configuration and forms an annular peripheral leakage occluder as shown in FIG. 2d. A pulling string 4 is provided to thread through the skirt 2 and cooperates with the radial deformation of the stent 1 during release.

The pulling string 4 includes a driving portion 4a and a force exerting portion 4b. The driving portion 4a movably threads through the skirt 2. The force exerting portion 4b is connected to the skirt 2 and movably threads through the corresponding portion of the skirt. During the release of the stent 1, the force exerting portion 4b is pulled by the driving portion 4a and has an axial displacement relative to the stent 1 to drag the skirt 2 to be stacked.

In this embodiment, other than the top of the skirt which is connected to the stent, the lower region of the skirt has a large movement degree relative to the stent. The lower region may be fixed or not fixed to the stent. For example, as shown in FIG. 2h, both the top edge 2a and the bottom edge 2b of the skirt 2 are fixed to the stent 1. Since the axial length of the skirt is longer than the length of the portion of the stent between the top edge 2a and the bottom edge 2b, the skirt may be folded in an axial direction to form a floating section around the outer periphery of the stent 1, wherein it is the floating section that forms the stacked configuration after being pulled by the pulling string 4.

The pulling string 4 which serves to act on the floating section includes a plurality of pulling units arranged in the circumferential direction. A portion of the pulling string, or a single pulling string, may serve as a single unit to drive the floating section to be folded axially, wherein one example based on the triangular deformation is shown below.

A single pulling unit is shown in FIG. 2b. Before release, the driving portion includes a first action portion X1 and a second action portion X2 respectively connected to the skirt, and the force exerting portion Y1 is movably connected to the skirt, wherein the first action portion X1 and the second action portion X2 may serve as threading ends, respectively, and the force exerting portion Y1 is located between the two threading ends.

Referring to FIG. 2c, the overall length of the portion of the pulling string corresponding to the pulling unit is fixed, that is, the overall length of the sides L1 and L2 of the triangle is fixed. When the stent is being released, the first acting portion X1 and the second acting portion X2 move away from each other in the directions indicated by the respective arrows, and thus the distance between the first acting portion X1 and the second acting portion X2 increases, and the shape of the triangle will change. Therefore, the force exerting portion Y1 as a vertex will move towards a line connecting the first action portion X1 and the second action portion X2 in the direction as indicated by the upward arrow, that is, the force exerting portion Y1 will move axially relative to the stent, and pull the skirt. It may be concluded that the circumferential span between the two threading ends is changed after the release of the stent relative to the stent being unreleased, and a relative displacement between the force exerting portion and the driving portion along the axial direction of the stent is produced during the release of the stent which causes the skirt to be pulled and stacked.

In order to obtain a larger deformation for the triangle of each pulling unit, the first acting portion X1 and the second acting portion X2 span one or more cells in the circumferential direction. For example, in this embodiment, the first acting portion X1 and the second acting portion X2 substantially span two cells. The central angle corresponding to the first acting portion X1 and the second acting portion X2 is 60 degrees after the stent is released. The pulling units circumferentially cover the entire skirt, however, only two pulling units are shown in the figures, with the others omitted for convenience of illustration.

All the pulling units are connected in a wave-like manner with a plurality of waves and each wave having a triangle shape. Along the extension direction of the pulling string, the force exerting portion Y1 is located between the first action portion X1 and the second action portion X2, and the first action portion X1 and the second action portion X2 are opposite to each other (namely, they are located at the same level along the axial direction). Alternatively, pulling units may be arranged in such a manner that they are spaced from each other. In other words, two adjacent pulling units do not share any portion of the pulling string. For ease of identification, the pulling string is indicated as dashed lines. Actually, the pulling string threads through in such a manner that some sections thereof are arranged outside of the skirt, and some sections thread into the inner side of the skirt via threading holes, and the sections located outside and the sections located inside are arranged alternatively in the circumferential direction.

Figure 2E:
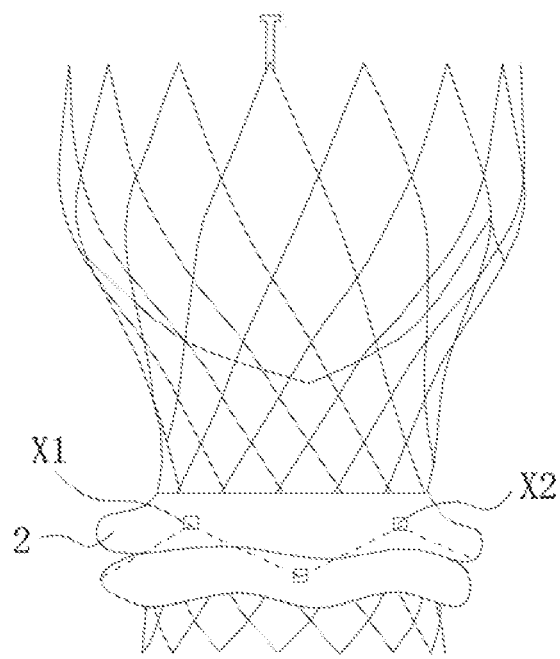
FIG. 2e is a schematic structural view of a stent apparatus, the pulling unit of which has a different circumferential span compared to the second embodiment.

Referring to FIG. 2e, in a further development, within the pulling string on the skirt 2, the central angle corresponding to the first acting portion X1 and the second acting portion X2 is 90 degrees.

Figure 2F:
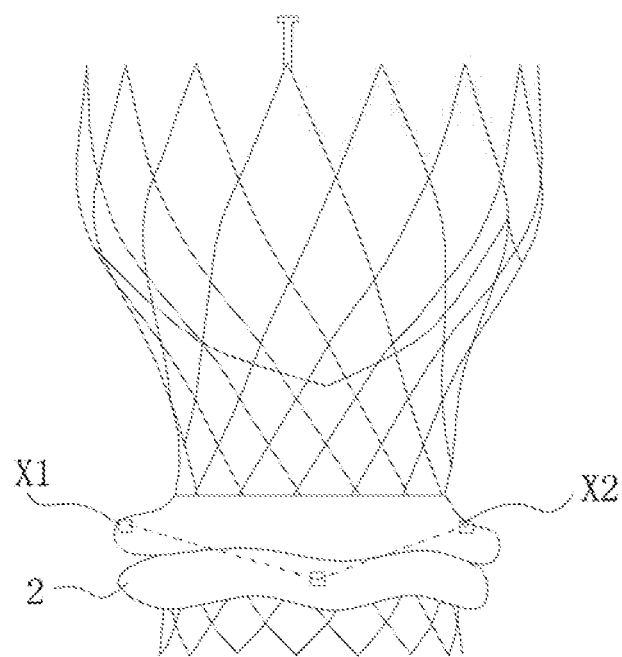
FIG. 2f is another schematic structural view of a stent apparatus, the pulling unit of which has a different circumferential span compared to the second embodiment.

Referring to FIG. 2f, in a further development, within the pulling string on the skirt 2, the central angle corresponding to the first acting portion X1 and the second acting portion X2 is 180 degrees.

Figure 2G:
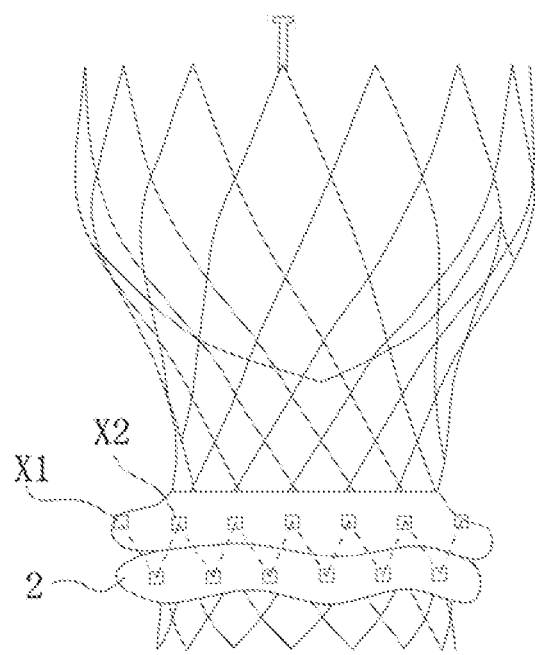
FIG. 2g is a further schematic structural view of a stent apparatus, the pulling unit of which has a different circumferential span compared to the second embodiment.
Figure 2H:
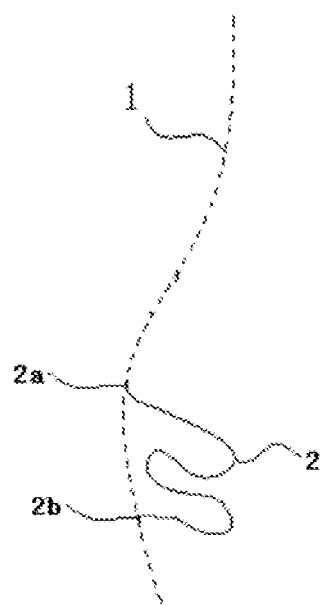
FIG. 2h is a schematic structural view of a stent apparatus, in which, compared to the second embodiment, both ends of the skirt are fixed.

Referring to FIG. 2g, in a further development, within the pulling string on the skirt 2, the central angle corresponding to the first acting portion X1 and the second acting portion X2 is 30 degrees.

Third Embodiment

Figure 3A:
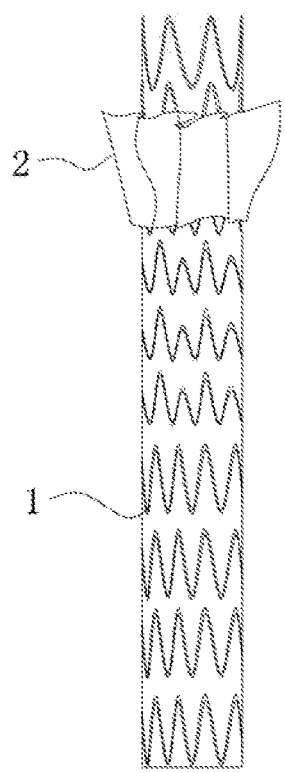
FIG. 3a is a schematic structural view of a stent apparatus according to a third embodiment of the present disclosure, showing a stent thereof before being released.
Figure 3B:
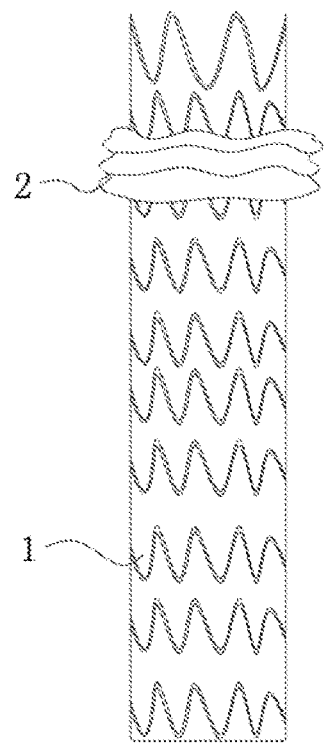
FIG. 3b is a schematic structural view of the stent apparatus according to the third embodiment, showing the stent thereof after being released.

Referring to FIGS. 3a and 3b, in this embodiment, the outer periphery of the stent 1 is provided with a flexible skirt 2. Before the stent 1 is released, the skirt 2 is in an unfolded configuration, which is axially unfolded and surrounds the outer periphery of the stent 1 before release. After the stent 1 is released, the skirt 2 is folded and stacked along the axial direction of the released stent 1 into an annular peripheral leakage occluder.

In this embodiment, the stent is a blood vessel stent, which may be used in large vessels such as the aorta. The shape and the application of the stent in this embodiment are different from those disclosed in the previous embodiments, however, the arrangements of the skirt and the functions are similar.

In this embodiment, the skirt 2 is made of flexible material, and constrains the outer periphery of the stent after the stent is released. During the release, the skirt has not yet constrained the stent, so it is possible for the skirt to adjust its position itself under the blood flow. In order to further limit the position of the skirt, a limiting string may be used in combination with the skirt.

Alternatively, even under the action of the limiting string, the skirt forming the peripheral leakage occluder may also be able to adjust its position itself under the blood flow.

Fourth Embodiment

Figure 4A:
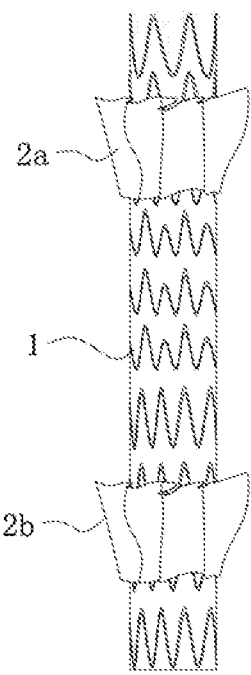
FIG. 4a is a schematic structural view of a stent apparatus according to a fourth embodiment of the present disclosure, showing a stent thereof before being released.
Figure 4B:
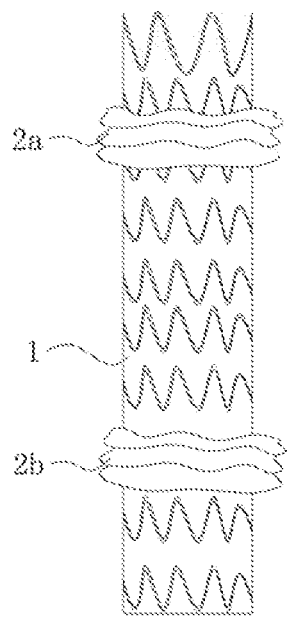
FIG. 4b is a schematic structural view of the stent apparatus according to the fourth embodiment, showing the stent thereof after being released.

Referring to FIGS. 4a and 4b, in this embodiment, the outer periphery of the stent 1 is provided with two flexible skirts. Before the stent 1 is released, the skirts are in unfolded configurations, which are axially unfolded and surrounds the outer periphery of the stent 1 before release. After the stent 1 is released, the skirts are folded and stacked along the axial direction of the released stent into stacked configurations and form annular peripheral leakage occluders.

This embodiment differs from the third embodiment in that the skirts here include a first skirt 2a and a second skirt 2b which are arranged one above the other in an axial direction, and each skirt in the stacked configuration forms a respective peripheral leakage occluder.

Fifth Embodiment

Figure 5A:
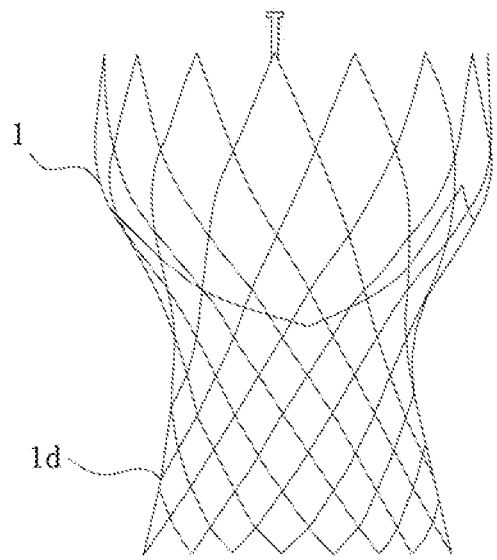
FIG. 5a is a schematic structural view of a stent apparatus according to a fifth embodiment of the present disclosure.

Referring to FIG. 5a, in which the skirt is omitted, this embodiment differs from the first embodiment in the structure of the stent 1. In this embodiment, the bottom of the stent 1 is provided with a flared driving structure 1d, which extends from the middle portion of the stent to the end of the stent (the bottom end). The closer to the bottom end of the stent, the larger the diameter for the flared driving structure 1d. In this embodiment, the generatrix of the flared driving structure 1d is substantially straight. The wider side (the bottom end) of the flared driving structure 1d is released first, and the narrow side is released later. Due to such configuration, the flared structure of the stent may operate in cooperation with the skirt during the release of the stent and guides the skirt to stack axially and stay in the stacked configuration.

Figure 5B:
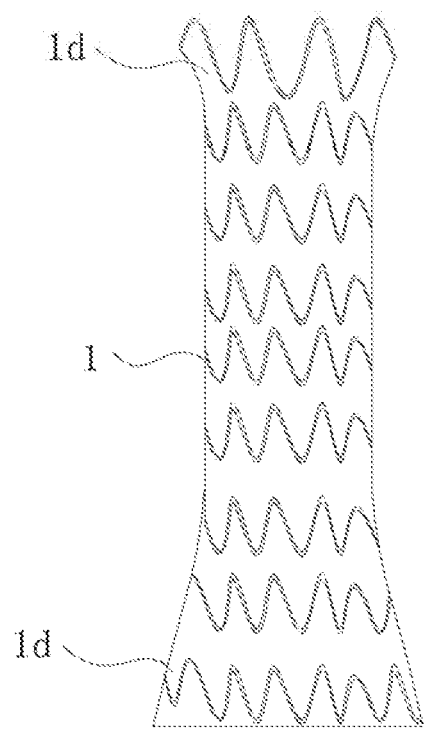
FIG. 5b is a schematic structural view of a stent, in which, compared to the stent shown in FIG. 5a, both ends thereof are flared.

As shown in FIG. 5b in which the skirt or skirts are omitted, in this embodiment, the skirts may be provided at one axial end or two axial ends of the stent such as in the third embodiment, and the stent 1 has flared driving structures 1d at both ends in the axial direction.

Sixth Embodiment

Figure 6:
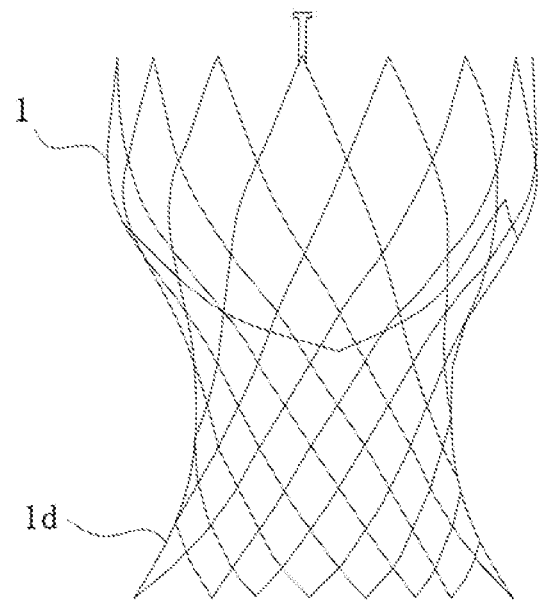
FIG. 6 is a schematic structural view of a stent apparatus according to a sixth embodiment of the present disclosure.

Referring to FIG. 6, in which the skirt or skirts are omitted, this embodiment differs from the fifth embodiment in the structure of the flared driving structures 1d. In this embodiment, the generatrix of the flared driving structure 1d at the bottom of the stent 1 is substantially curved, and thus has a bottom end turning more outwardly relative to that shown in the fifth embodiment.

Seventh Embodiment

Figure 7A:
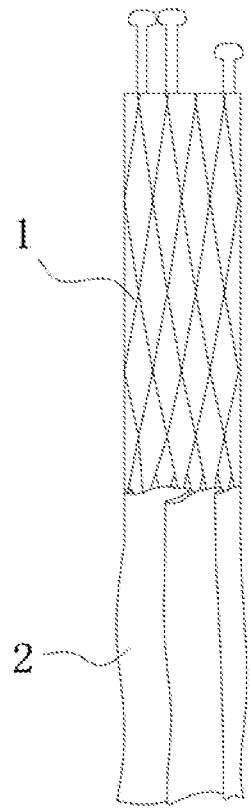
FIG. 7a is a schematic structural view of a stent apparatus according to a seventh embodiment of the present disclosure, showing the stent before being released.
Figure 7B:
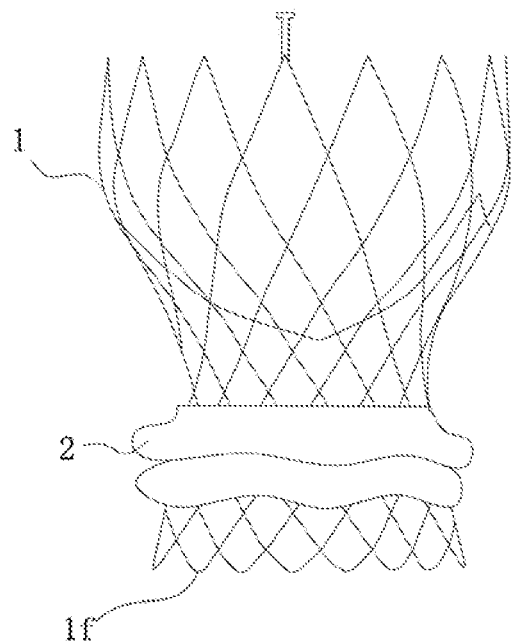
FIG. 7b is a schematic structural view of the stent apparatus according to the seventh embodiment, showing the stent after being released.
Figure 7C:
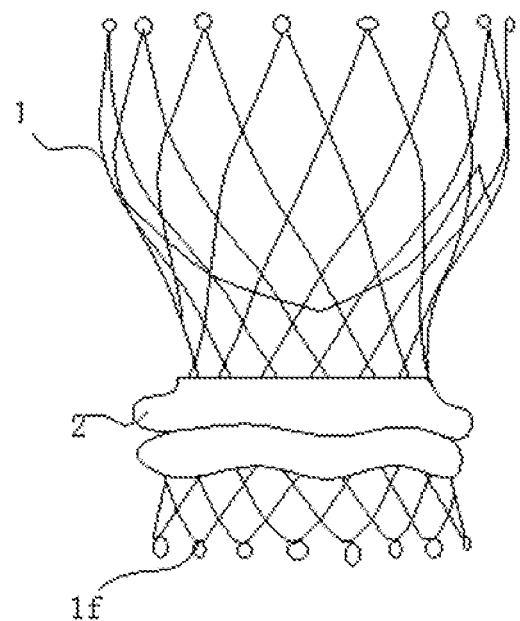
FIG. 7c is a schematic structural view of the stent apparatus according to the seventh embodiment, showing the stent after being expanded.

Referring to FIGS. 7a and 7b, this embodiment differs from the first embodiment in that an axial end of the stent 1 has a smooth curved edge, instead of an edge with sharp tips shown in the first embodiment. Before the stent 1 is released, the corresponding side of the skirt 2 extends axially beyond the stent or just extends to the end of the stent.

In this embodiment, the edge of the distal end of the stent 1 to be released first is formed by a plurality of arc sections if connected one another. Since the arc sections if would not pierce or snag the skirt 2, it is allowable for the skirt 2 to extend axially beyond or exactly to the distal end of the stent to be released first before the stent is released. As a result, a longer skirt may be obtained, which forms a peripheral leakage occluder with a higher profile and a larger volume, thereby improving the sealing effect.

Eighth Embodiment

Figure 8:
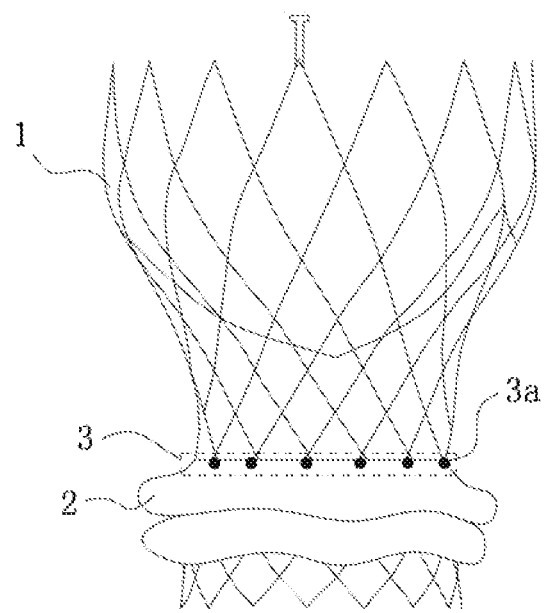
FIG. 8 is a schematic structural view of a stent apparatus according to an eighth embodiment of the present disclosure.

Referring to FIG. 8, in this embodiment, the outer periphery of the stent 1 is provided with a flexible skirt 2. Before the stent 1 is released, the skirt 2 is in an unfolded configuration, which is axially unfolded and surrounds the outer periphery of the stent 1 before release. After the stent 1 is released, the skirt 2 is folded and stacked along the axial direction of the released stent 1 into a stacked configuration and forms an annular peripheral leakage occluder.

The top edge of the skirt 2 serves as a fixing band 3 which is stitched on the stent with spaced stitching portions 3a as shown in the figure. At least a part of the skirt 2 remains in a fixed position relative to the stent and is free of the influence of external factors such as blood flow, which functions to control the position of the peripheral leakage occluder.

In this embodiment, there is a single fixing band 3 which is located at the middle portion of the stent, with the remaining skirt there below floating around the outer periphery of the stent 1 before being stacked. Alternatively, it is possible to provide several fixing bands.

The skirt is fixed to the stent only at the fixing band, with the remaining skirt movable relative to the stent. In particular, at least a part of the skirt is movable axially so that it can be folded. In the case of only a single fixing band provided, the remaining skirt floats around the outer periphery of the stent. In the case of several fixing bands provided, the skirt may also be foldable provided that the axial length of the skirt between two adjacent fixing bands is sufficient. For example, in the second embodiment shown in FIG. 2h, the top edge 2a and the bottom edge 2b of the skirt 2 are both fixed on the stent 1. Since the length of the skirt is longer than the length of the corresponding portion of the stent, that is, the axial length of the skirt is sufficient, the skirt can be folded to form a floating section.

The skirt may be foldable provided that the axial length of the skirt between two fixing bands is sufficient. For example, in the case that the axial length of the corresponding portion of the stent between the two fixing bands is L1 and the axial length of the skirt between the two fixing bands is L2, it is possible for the skirt to be axially stacked provided that L1 is less than L2. The redundant section of the skirt in an unfolded configuration may be overlapped and rested on the outer periphery of the stent, wherein the overlapped sections are folded axially, which will be further described hereinafter.

Ninth Embodiment

Figure 9:
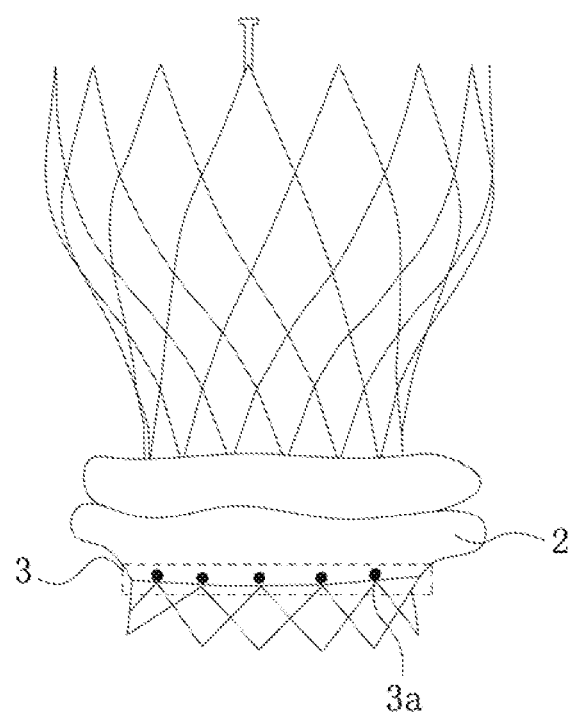
FIG. 9 is a schematic structural view of a stent apparatus according to a ninth embodiment of the present disclosure.

Referring to FIG. 9, this embodiment differs from the eighth embodiment in that the fixing band 3 here is located at the bottom of the stent, and the remaining skirt above the fixing band floats around the outer periphery of the stent 1 before being stacked.

Tenth Embodiment

Figure 10:
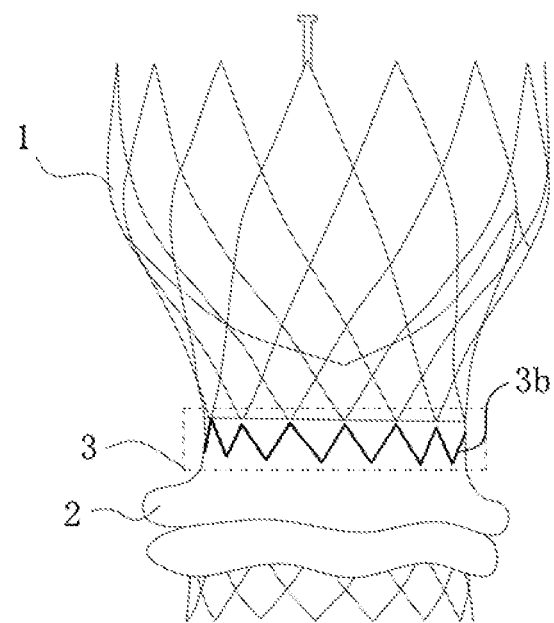
FIG. 10 is a schematic structural view of a stent apparatus according to a tenth embodiment of the present disclosure.

Referring to FIG. 10, the stent in this embodiment has a meshed structure with a plurality of grids. This embodiment differs from the eighth embodiment in that the fixing band 3 here is stitched on the meshed stent by a continuous stitch line 3b. Corresponding to the grids of the meshed stent, the stitch line 3b undulates in the axial direction while extending in the circumferential direction, thereby forming a wave-like configuration.

Eleventh Embodiment

Figure 11:
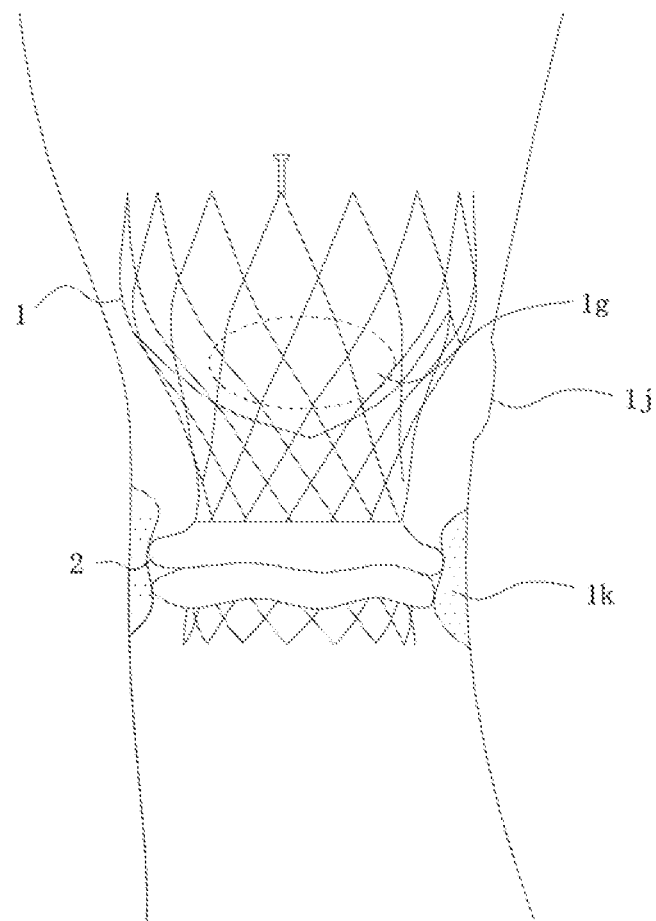
FIG. 11 is a schematic structural view of a stent apparatus according to an eleventh embodiment of the present disclosure.

Referring to FIG. 11, in this embodiment, the outer periphery of the stent 1 is provided with a flexible skirt 2. Before the stent 1 is released, the skirt 2 is in an unfolded configuration, which is axially unfolded and surrounds the outer periphery of the stent 1 before release. After the stent 1 is released, the skirt 2 is folded and stacked along the axial direction of the stent 1 after release into a stacked configuration and forms an annular peripheral leakage occluder. The position of the peripheral leakage occluder corresponds to that of the valve cusps 1k.

The stent is an aortic valve stent, and valves are provided in the stent. In operation, the stent is implanted at the lesion site at the aortic valve of a human heart. Since there is a coronary inlet 1j distributed around the aortic valve annulus, the stacked skirt should avoid the branch vessel in an axial position. Depending on the physiological structure of the lesion site, after the stent is released, a hollow area 1g should be free from coverage by the skirt 2, otherwise the skirt 2 would block the blood flow into the coronary entrance 1j. Thus, the skirt should be provided at an axial position which avoids the channel (the hollow area 1g) formed on the stent for blood flow.

The skirt may be made of the same material as the valve, such as animal pericardium or other biocompatible flexible materials.

Twelfth Embodiment

Figure 12:
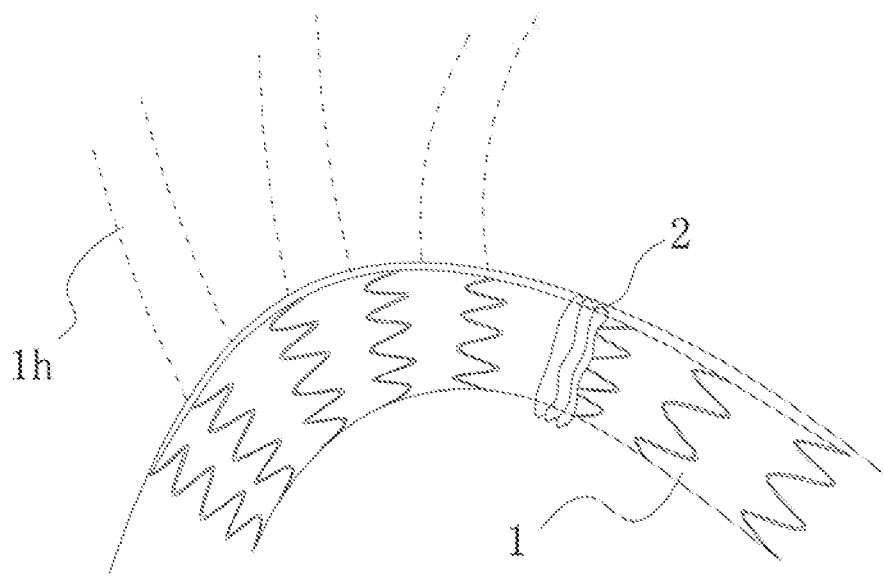
FIG. 12 is a schematic structural view of a stent apparatus according to a twelfth embodiment of the present disclosure.

Referring to FIG. 12, in this embodiment, the outer periphery of the stent 1 is provided with a flexible skirt. Before the stent 1 is released, the skirt is in an unfolded configuration, which is axially unfolded and surrounds the outer periphery of the stent 1 before release. After the stent 1 is released, the skirt 2 is folded and stacked along the axial direction of the stent 1 into a stacked configuration after release and forms an annular peripheral leakage occluder.

This stent 1 is generally configured to be applied to the aortic arch. Due to the physiological structure of the aortic arch, the side wall of the stent would face the branch blood vessels 1h after the stent is released, which, should be free from coverage by the skirt 2, otherwise, the blood flow would be blocked. Therefore, the stacked skirt should be provided to avoid the branch blood vessels 1h in the axial position.

Thirteenth Embodiment

Figure 13A:
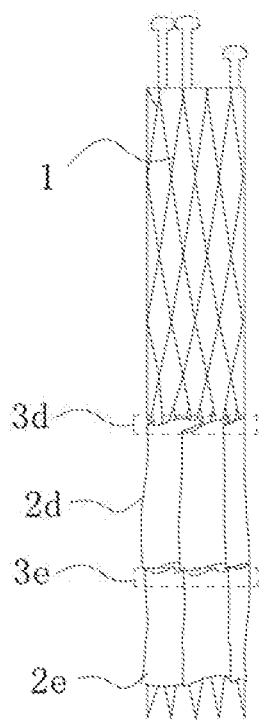
FIG. 13a is a schematic structural view of a stent apparatus according to a thirteenth embodiment of the present disclosure, showing the stent before being released.
Figure 13B:
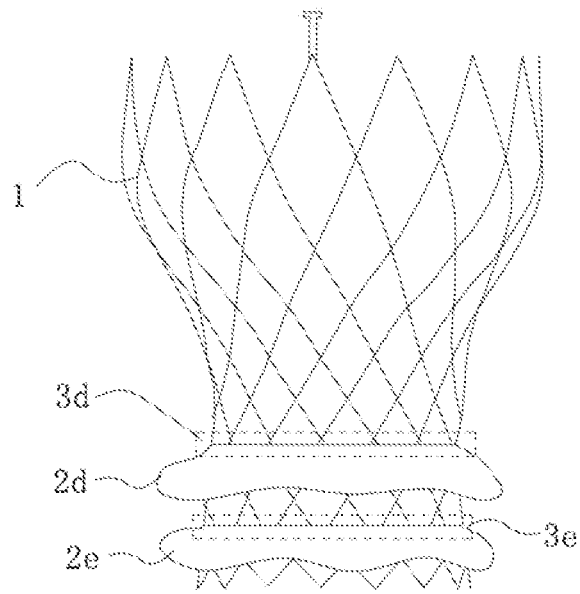
FIG. 13b is a schematic structural view of the stent apparatus according to the thirteenth embodiment, showing the stent after being released.

Referring to FIGS. 13a and 13b, in this embodiment, the outer periphery of the stent 1 is provided with flexible skirts. Before the stent 1 is released, the skirts are in unfolded configurations, which are axially unfolded and surrounds the outer periphery of the stent 1 before release. After the stent 1 is released, the skirts are folded and stacked along the axial direction of the stent after release into stacked configurations and form annular peripheral leakage occluders. In this embodiment, there are two skirts, i.e., a first skirt 2d and a second skirt 2e. Each of the first and second skirts 2d and 2e in the stacked configuration forms a respective peripheral leakage occluder.

The top edges of the first and second skirts 2d and 2e are connected to the stent at two fixing bands 3d and 3e, respectively, by means of spaced stitching portions or continuous stitch lines. The ends of the first and second skirts 2d and 2e opposite to the top edges are floating edges.

The first skirt 2d in the stacked condition is configured to form a first peripheral leakage occluder, and the second skirt 2e in the stacked condition is configured to form a second peripheral leakage occluder. The two peripheral leakage occluders are separated. The first peripheral leakage occluder is arranged closer to the top of the stent than the second peripheral leakage occluder. In the unfolded configurations, the first skirt 2d has an axial length of 1.5 to 3 times to the axial length of the second skirt 2e. After being stacked, the first peripheral leakage occluder generally has a larger cross section than the second peripheral leakage occluder. That is, after being stacked, the first peripheral leakage occluder at the top has a higher profile and the peripheral leakage occluder at the bottom has a lower profile. In the unfolded configurations, the bottom edge of the first skirt 2d extends to the top edge of the second skirt 2e, without overlapping one another. That is, the first and second skirts are arranged end to end, which not only maximizes the advantages of the sufficient axial lengths thereof, but also avoids an increased radial thickness caused by overlap of the first and second skirts so as to ensure smooth loading of the stent, i.e., compression of the stent into the delivery system.

Fourteenth Embodiment

Figure 14A:
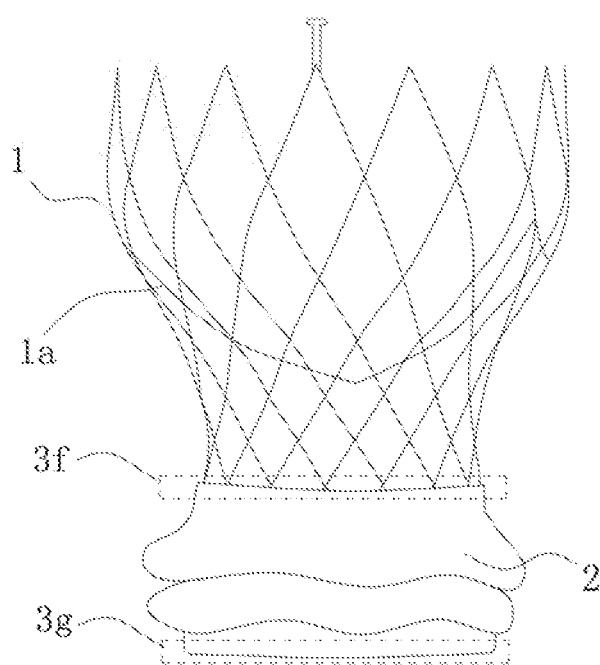
FIG. 14a is a schematic structural view of a stent apparatus according to a fourteenth embodiment of the present disclosure.
Figure 14B:
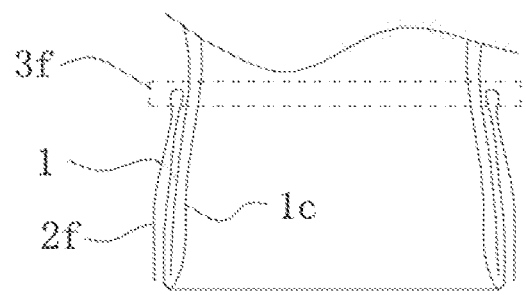
FIG. 14b is a schematic structural view showing a skirt of the stent apparatus according to the fourteenth embodiment in an unfolded configuration.
Figure 14C:
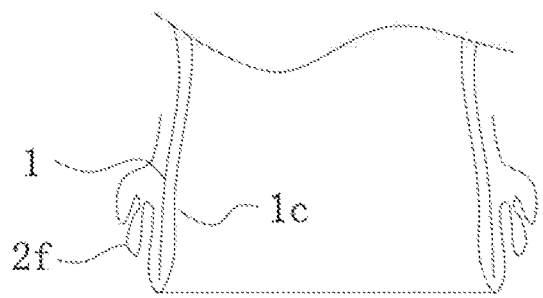
FIG. 14c is a schematic structural view showing the skirt of the stent apparatus according to the fourteenth embodiment in a stacked configuration.

Referring to FIGS. 14a to 14c, in this embodiment, the outer periphery of the stent 1 is provided with a flexible skirt. Before the stent 1 is released, the skirt is in unfolded configuration, which is axially unfolded and surrounds the outer periphery of the stent 1 before release. After the stent 1 is released, the skirt is folded and stacked along the axial direction of the stent 1 after release into a stacked configuration and forms an annular peripheral leakage occluder.

As shown in FIG. 14a, in this embodiment, valves 1a and an inner coverage membrane 1c are provided in the stent 1. The top edge of the skirt 2 is connected to the stent at a first fixing band 3f, and the bottom edge of the skirt 2 is connected to the bottom edge of the stent at a second fixing band 3g, wherein the first and second fixing bands 3f and 3g may be stitched by means of spaced stitching portions or continuous stitch lines, respectively.

The inner coverage membrane 1c inside the stent extends to the bottom end of the stent, and the bottom edge of the skirt 2 outside the stent also extends to the bottom end of the stent. The inner coverage membrane 1c and the skirt 2 may be separately formed or integrally formed as a single piece. In this embodiment, it is preferred to form them as a single piece, in which case the inner coverage membrane inside the stent first extends to the end of the stent, and then turns outwards to form the skirt, which may simplify the cutting process during stitching and maintain the integrity of the stent apparatus.

As shown in FIG. 14b, the inner coverage membrane 1c is integrally formed with the skirt 2 as a single piece. This embodiment differs from the embodiment shown in FIG. 14a in that only a single fixing band 3f is provided. The skirt 2 first extends upwardly from the position where the skirt 2 is connected with the inner cover 1c, i.e. the bottom edge of the stent 1, to the axially highest end of the skirt 2, i.e. the top of the skirt. The top edge of the skirt 2 is connected to the stent at the fixing band 3f. The skirt 2 then turns downwards from the highest end and forms an evaginated floating section 2f. The floating section 2f is axially extended before the stent 1 is released. After the stent 1 is released, the floating section 2f is stacked under elastic effect or blood flow. In addition, the floating section 2f may also be pulled and stacked in combination with the pulling string of the present invention to form an annular protrusion protruding radially to serve as a peripheral leakage occluder.

The configuration in FIG. 14c may also be shaped by stitching in advance. The unfolded configuration of the skirt in the axial direction is obtained only by compressing radially, with the folded configuration still retained. After the stent is released, the floating section 2f in the human body will expand further through the influence of blood flow or the like.

Figure 14D:
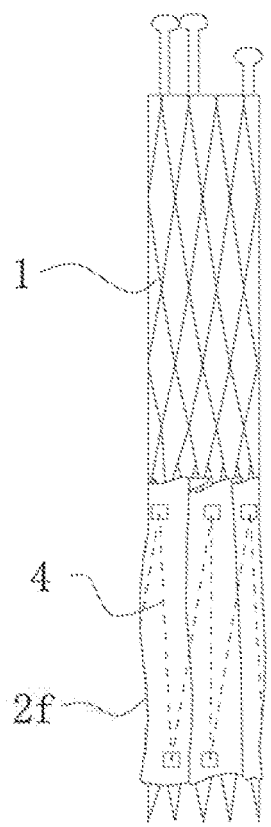
FIG. 14d is a schematic structural view of a stent apparatus which, compared to that of FIG. 14b, shows a pulling string provided.
Figure 14E:
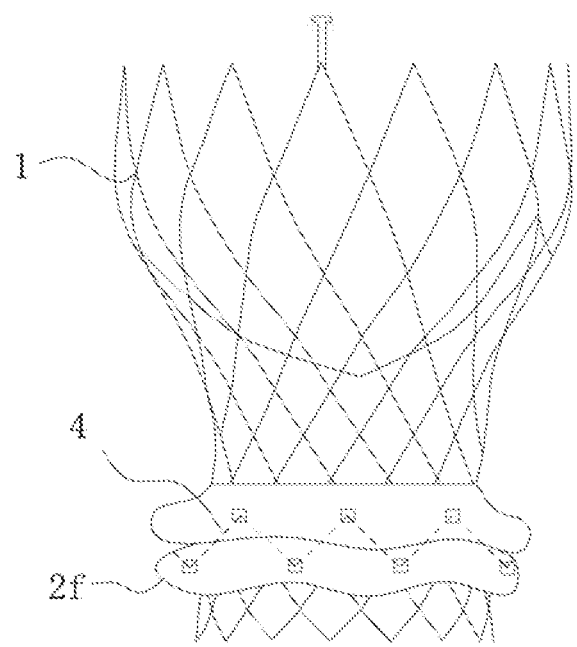
FIG. 14e is a schematic structural view of a stent apparatus which, compared to that of FIG. 14c, shows a pulling string provided.

Referring to FIGS. 14d and 14e, the transition of the skirt 2 from the unfolded configuration to the stacked configuration will be described in a further development in combination with the arrangement of the skirts shown in FIGS. 14a to 14c.

A pulling string 4 is provided on the floating section 2f of the skirt. The pulling string 4 generally threads through the floating section 2f in the circumferential direction. The pulling string 4 undulates in the axial direction while extending along the circumferential direction of the stent, forming a wave-like configuration with peaks and valleys. In the unfolded configuration, the peaks are at the same level in the axial position, and the valleys are at the same level in the axial position. Alternatively, the peaks (or the valleys) may be offset from each other.

In order to facilitate the threading of the pulling string, a set of first threading holes is provided on the skirt corresponding to the peaks, and a set of second threading holes is provided corresponding to the valleys. The pulling string alternately threads the first threading hole and the second threading hole and forms a wave-like configuration. The pulling string alternatively threads into and out of the surfaces of the skirt.

Two adjacent peaks serve as two threading ends operating in cooperation with the skirt. The circumferential span between the two threading ends is changed after the release of the stent relative to the stent being unreleased. During the release of the stent, driven by the deformed stent, the peaks move away from each other in the circumferential direction and thus drive the valleys to lift upwardly, thereby axially stacking the floating section 2f.

The peaks and valleys are relative concepts. Actually, either one can be designated as the peak, and the other one can be designated as the valley. During the release of the stent, driven by the deformed stent, the valleys also move away from each other in the circumferential direction and thus drive the peaks to move axially. Therefore, the movements of the peaks and valleys are relative to each other. In any case, the intention is to drive the peaks and valleys to move axially towards each other.

Figure 14F:
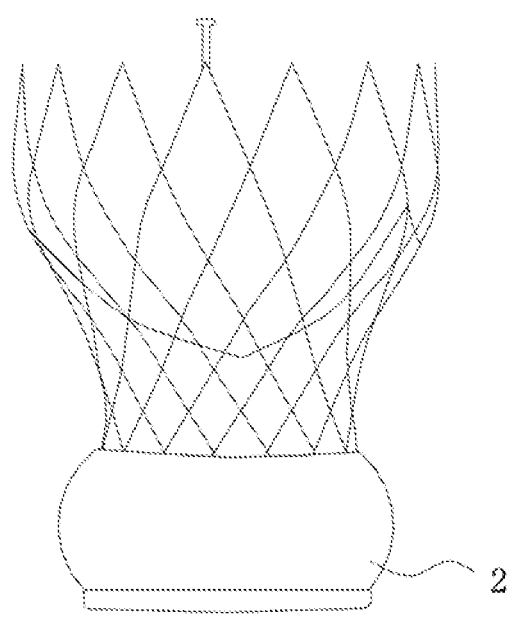
FIG. 14f is a schematic structural view of a stent apparatus with a skirt having a double-layered structure.

Referring to FIG. 14f, in a further development, the skirt 2 has a double-layered structure which is filled with a water-absorbing expansion material. After being released in the human body, the water-absorbing expansion material absorbs water and expands radially. Due to the coverage of the skirt made of a membrane material, the risk of the water-absorbing expansion material falling off can be avoided.

Figure 14G:
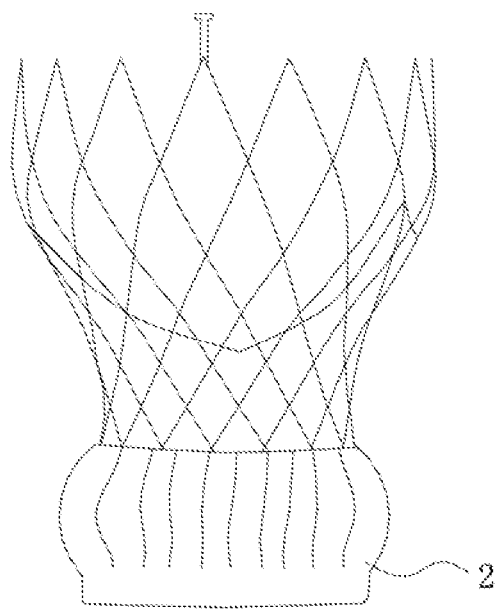
FIG. 14g is a schematic structural view of a stent apparatus with a skirt having a pleated structure.

Referring to FIG. 14g, in a further development, the skirt 2 may have folded sections in a circumferential direction which overlap one another in a radial direction to cooperatively form a radial protrusion.

Figure 14H:
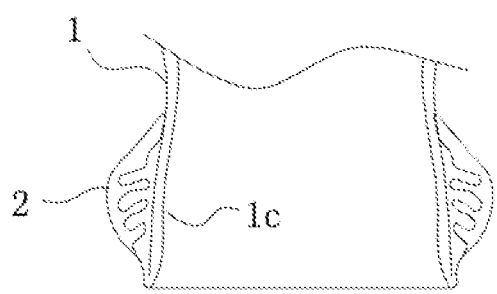
FIG. 14h is a schematic structural view of a skirt having an alternative double-layered structure.

Referring to FIG. 14h, in a further development, an interlayer is provided between the skirt 2 and the inner coverage membrane 1c, which may be formed by folding a part of the skirt 2. Preferably, the inner coverage membrane c extends upwardly from the bottom edge of the stent. The top of the interlayer is fixed on the stent. The skirt turns downwards from the top of the interlayer and may be configured as a floating section that floats outside the interlayer. The skirt may be fixed on the interlayer or at a bottom of the interlayer, or may be fixed on the inner coverage membrane 1c. The floating section may be pulled and stacked in the technique shown in FIG. 14e to form an annular protrusion protruding radially to serve as a peripheral leakage occluder.

Figure 14I:
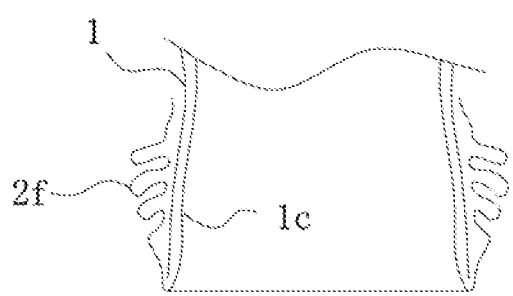
FIG. 14i is a schematic structural view of a skirt in another stacked manner.

Referring to FIG. 14i, in a further development, the skirt 2 extends upwardly from the position where the skirt 2 is connected with the inner coverage membrane 1c, that is, from the bottom edge of the stent 1. The entire upwardly extending portion of the skirt 2 is configured as a floating section 2f, with the end of the floating section 2f distant from the bottom edge being a floating edge. The floating section 2f is axially unfolded before the stent 1 is released, and may be pulled and stacked in the technique shown in FIG. 14e to form an annular protrusion protruding radially to serve as a peripheral leakage occluder. The difference there between is that it is the top edge of the floating section 2f that moves towards the bottom edge here, but the principles are the same.

Fifteenth Embodiment

Figure 15:
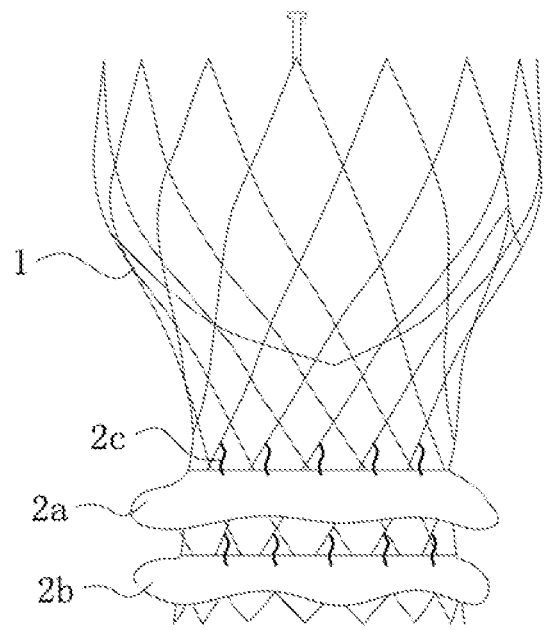
FIG. 15 is a schematic structural view of a stent apparatus according to a fifteenth embodiment of the present disclosure.

Referring to FIG. 15, in this embodiment, the outer periphery of the stent 1 is provided with flexible skirts. Before the stent 1 is released, the skirts are in unfolded configurations, which are axially unfolded and surrounds the outer periphery of the stent 1 before release. After the stent 1 is released, the skirts are folded and stacked along the axial direction of the stent 1 after release into stacked configurations and form annular peripheral leakage occluders.

In this embodiment, there are two skirts, i.e. a first skirt 2a and a second skirt 2b, which are arranged one above the other in an axial direction. During the release of the stent, the expanded stent is gradually constrained by at least portions of the skirts, and the skirts are driven to be axially pulled with the further release of the stent. Each skirt is axially pulled and stacked to form a respective peripheral leakage occluder. In order to adapt to the axial movement of the skirts and prevent the skirts from falling off the stent, flexible limiting strings 2c are respectively provided between the stent 1 and the first and second skirts 2a and 2b, and thus security is improved. The limiting string 2c may include a plurality of strips distributed in an axial direction, or a single strip stitched on the periphery of the skirt in a pattern of a rectangular wave. The first and second skirts 2a and 2b are provided with respective pulling strings.

Sixteenth Embodiment

Figure 16A:
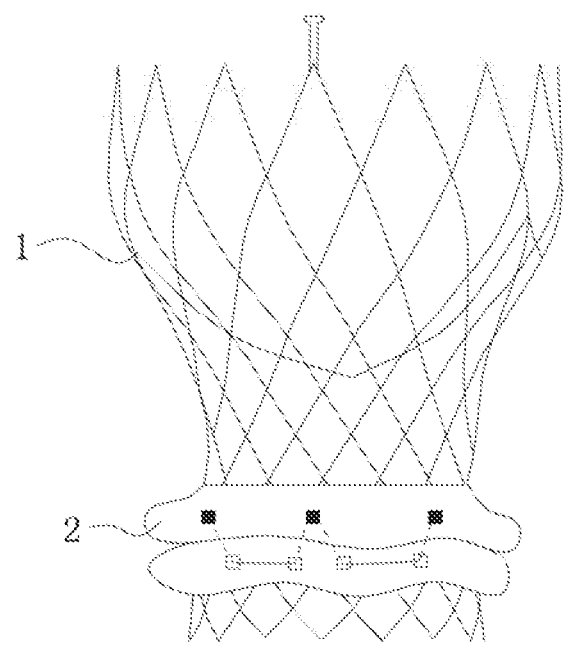
FIG. 16a is a schematic structural view of a stent apparatus according to a sixteenth embodiment of the present disclosure.
Figure 16B:
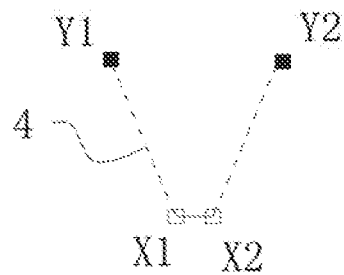
FIG. 16b is a schematic structural view of a pulling unit of the stent apparatus according to the sixteenth embodiment.

Referring to FIGS. 16a and 16b, in this embodiment, the outer periphery of the stent 1 is provided with a flexible skirt 2. Before the stent 1 is released, the skirt 2 is in an unfolded configuration, which is axially unfolded and surrounds the outer periphery of the stent 1 before release. After the stent 1 is released, the skirt 2 is folded and stacked along the axial direction of the stent 1 after release into a stacked configuration and forms an annular peripheral leakage occluder. Also provided is a pulling string 4 which is configured to drive the skirt 2 to transform into the stacked configuration. The pulling string 4 cooperates with the radial deformation of the stent during release.

In this embodiment, the entire pulling unit is in the shape of a trapezoid, with the force exerting portions Y1 and Y2 of the pulling string 4 respectively fixed on the skirt 2. The first acting portion X1 and the second acting portion X2 are arranged at the bottom end of the stent (i.e., the distal end which is to be released first). In other words, the driving portion is located at the distal end of the stent (and also of the skirt) which is to be released first, and the force exerting portions are located at the proximal end of the stent (and also of the skirt) which is to be released later.

During the release of the stent, the perimeter of the stent increases. The first acting portion X1 and the second acting portion X2 move away from each other, and the shape of the pulling unit changes. The portions of the skirt connected with the first acting portion X1 and the second acting portion X2 move towards the force exerting portions Y1 and Y2. That is, the acting portions X1, X2 and the force exerting portions Y1, Y2 move axially towards each other, so as to pull the skirt.

Seventeenth Embodiment

Figure 17:
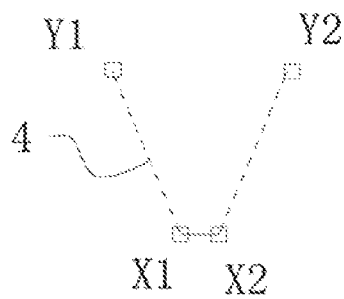
FIG. 17 is a schematic structural view of a pulling unit of a stent apparatus according to a seventeenth embodiment of the present disclosure.

Referring to FIG. 17, this embodiment differs from the sixteenth embodiment in that the force exerting portions Y1 and Y2 here movably thread through the skirt 2 respectively, and the force exerting portions Y1 and Y2 may be respectively connected to adjacent pulling units.

Eighteenth Embodiment

Figure 18A:
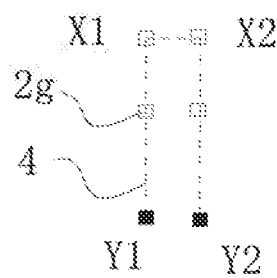
FIG. 18a is a schematic structural view of a pulling unit of a stent apparatus according to a eighteenth embodiment of the present disclosure, showing the pulling unit before being released.
Figure 18B:
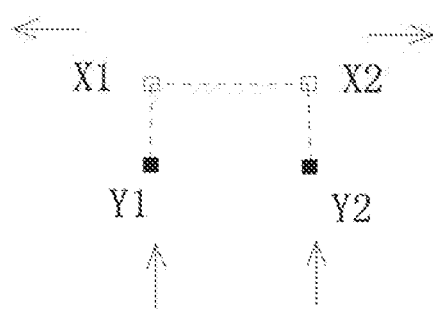
FIG. 18b is a schematic structural view of a pulling unit of a stent apparatus according to the eighteenth embodiment, showing the pulling unit after being released.

Referring to FIG. 18a and FIG. 18b, in this embodiment, the outer periphery of the stent is provided with a flexible skirt. Before the stent is released, the skirt is in an unfolded configuration, which is axially unfolded and surrounds the outer periphery of the stent before release. After the stent is released, the skirt is folded and stacked along the axial direction of the stent after release into a stacked configuration and forms an annular peripheral leakage occluder. Also provided is a pulling string 4 that is configured to drive the skirt into a stacked configuration. The pulling string 4 cooperates with the radial deformation of the stent during release.

In this embodiment, the pulling string 4 movably threads through the skirt at the first acting portion X1 and the second acting portion X2. The two ends of the pulling string 4 are respectively fixed on the skirt 2 as force exerting portions Y1 and Y2.

The entire pulling unit is in the shape of a rectangle or trapezoid. During the release of the stent, the perimeter of the stent increases. The first acting portion X1 and the second acting portion X2 move away from each other, and the shape of the pulling unit changes. The force exerting portions Y1 and Y2 move towards a line connecting the first acting portion X1 and the second acting portion X2, that is, move axially relative to the stent, so as to pull the skirt.

In the case that the pulling string 4 has a long course, in order to limit the position thereof relative to the skirt or to limit the threading direction thereof, a plurality of threading holes 2g may be provided on the skirt based on a preset threading course, such that the pulling string may thread through the plurality of threading holes 2g so as to ensure the pulling performance.

Nineteenth Embodiment

Figure 19:
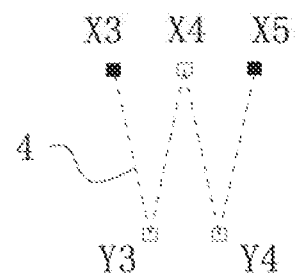
FIG. 19 is a schematic structural view of a pulling unit of a stent apparatus according to a nineteenth embodiment of the present disclosure.

Referring to FIG. 19, in this embodiment, the outer periphery of the stent is provided with a flexible skirt. Before the stent is released, the skirt is in an unfolded configuration, which is axially unfolded and surrounds the outer periphery of the stent before release. After the stent is released, the skirt is folded and stacked along the axial direction of the stent after release into a stacked configuration and forms an annular peripheral leakage occluder. Also provided is a pulling string 4 that is configured to drive the skirt into a stacked configuration. The pulling string 4 cooperates with the radial deformation of the stent during release.

In this embodiment, the motions of adjacent pulling units are cooperative to each other during deformation. Two pulling units are taken as an example in FIG. 19, and the same principle is applicable to more than two pulling units.

Within the first pulling unit: an action portion X3 is fixed on the skirt; an action portion X4 movably threads through the skirt; and a force exerting portion Y3 movably threads through the skirt.

Within the second pulling unit: an action portion X4, as a common action portion X4 shared with the first pulling unit, movably threads through the skirt; an action portion X5 is fixed on the skirt; and a force exerting portion Y4 movably threads through the skirt.

This portion of the pulling string 4 is generally W-shaped, and the overall length of the W-shaped pulling string is fixed. When the stent is being released, the three action portions move away from each other. As the common action portion X4 movably threads through the skirt, the portions of the pulling string corresponding to the two pulling units may be pulled against each other and possibly with a displacement there between. As a result, the two pulling units influence and interact with each other when deforming. Therefore, the two pulling units move in cooperation with each other. The same principle is applicable to more than two pulling units.

Twentieth Embodiment

Figure 20A:
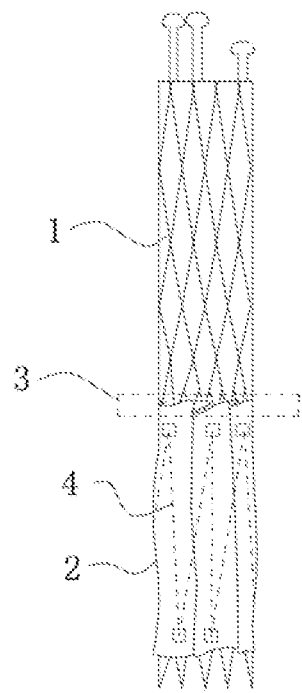
FIG. 20a is a schematic structural view of a stent apparatus according to a twentieth embodiment of the present disclosure, showing a stent before being released.
Figure 20B:
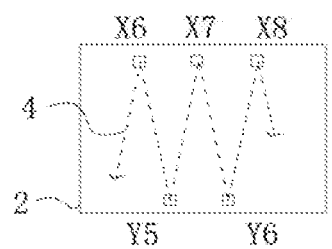
FIG. 20b illustrates how the pulling string of the stent apparatus according to the twentieth embodiment threads through the skirt.
Figure 20C:
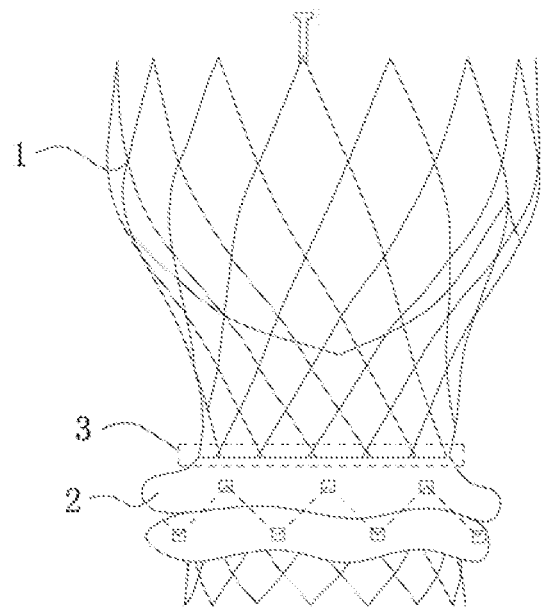
FIG. 20c is a schematic structural view of the stent apparatus according to the twentieth embodiment, showing the stent after being released.

Referring to FIGS. 20a to 20c, in this embodiment, the outer periphery of the stent 1 is provided with a flexible skirt 2. Before the stent 1 is released, the skirt 2 is in an unfolded configuration, which is axially unfolded and surrounds the outer periphery of the stent 1 before release. Preferably, the perimeter of the skirt is equal to or slightly greater than the perimeter of a corresponding portion of the stent so that the skirt conforms around the corresponding portion of the stent. Also provided on the skirt is a pulling string 4 that is configured to drive the skirt into a stacked configuration. The pulling string 4 cooperates with the radial deformation of the stent 1 during release. When the stent is being released in the human body, the bottom edge of the skirt 2 is released first, and then the top edge of the skirt 2 is released later. After the stent 1 is released, the skirt 2 is in the stacked configuration, which is folded and stacked along the axial direction of the stent 1 after release and forms an annular peripheral leakage occluder.

The top edge of the skirt 2 serves as a fixing band 3, which may be stitched on the stent in the same stitching technique as shown in FIG. 8 with spaced stitching portions. At least a part of the skirt 2 remains in a fixed position relative to the stent and is free of the influence of external factors such as blood flow, which functions to control the position of the peripheral leakage occluder. In this embodiment, there is a single fixing band 3 provided at the middle portion of the stent, and the portion of the skirt below the fixing band 3 floats around the outer periphery of the stent 1 before being stacked.

Alternatively, the fixing band may be fixed on the stent in the same stitching technique as shown in the tenth embodiment. The stitch line on the fixing band 3 may undulate in the axial direction while extending in the circumferential direction. In other words, the corresponding portion of the stent has a meshed structure with a plurality of grids, and the stitch line extends along the edges of the grids and forms a wave-like configuration.

The hollow boxes in the figures illustrate that the portion of the pulling string here threads through the skirt without threading through the stent.

In this embodiment, the pulling string generally threads through the skirt in a circumferential direction, which undulates in the axial direction of the stent while extending in the circumferential direction, thereby forming a wave-like configuration with peaks and valleys.

Within a periodic portion of the pulling string 4, peak X6, valley Y5, peak X7, valley Y6, peak X8 are distributed in the circumferential direction one after the other while undulating in the axial direction. In the unfolded configuration, the peaks are at the same level in the axial position, and the valleys are at the same level in the axial position. Alternatively, the peaks (or the valleys) may also be offset from each other.

In order to facilitate the threading of the pulling string, a set of first threading holes is provided on the skirt corresponding to the peaks, and a set of second threading holes is provided corresponding to the valleys. The pulling string alternatively threads the first threading hole and the second threading hole and forms the wave-like configuration. The pulling string alternatively threads into and out of the surfaces of the skirt.

Two adjacent peaks may serve as the driving portion of the pulling string, i.e., the two threading ends interacting with the skirt. The circumferential span between two threading ends such as the above-mentioned peaks X6 and X8 is changed after the stent is released relative to the stent being unreleased. Both the circumferential span and the axial length of the entire pulling unit are changed after the stent is released relative to the stent being unreleased.

During the release of the stent, the stent drives the pulling string on the skirt. Driven by the deformed stent, the peaks of the pulling string move away from each other in the circumferential direction and thus drive the valleys to lift upwardly. Since the pulling string movably threads through the skirt, the periodic portions thereof are configured for driving and operating in cooperation with one another, thereby generally moving the pulling string. The peaks and valleys are relative concepts. Actually, either one may be designated as the peak, and the other one can be designated as the valley. During the release of the stent, driven by the deformed stent, the valleys move away from each other in the circumferential direction and thus drive the peaks to move axially. Therefore, the movements of the peaks and valleys are relative to each other. In any case, the intention is to drive the peaks and valleys to move axially towards each other.

During manufacturing, the top edge of the skirt is first fixed on the preformed stent, the pulling string is circumferentially provided on the skirt, then the pulling string is tensioned to fold the skirt and finally the two ends of the pulling string are connected.

Twenty-First Embodiment

Figure 21:
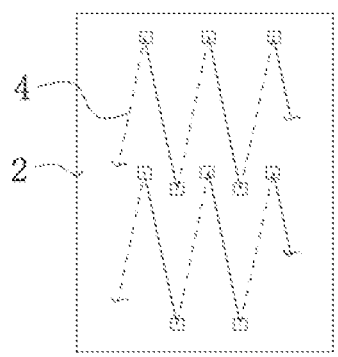
FIG. 21 illustrates how the pulling string of the stent apparatus according to the twenty-first embodiment of the present disclosure threads through the skirt.

Referring to FIG. 21, this embodiment differs from the twentieth embodiment in that two sets of pulling strings 4 are provided here, one above the other in an axial direction, which are configured to pull the corresponding portions of the skirt 2 at different stages during releasing of the stent, respectively. The peaks of the lower pulling string are located higher than the valleys of the upper pulling string. Each pulling string moves together in the circumferential direction to pull the skirt.

In order to further show the threading of the pulling string through the skirt, the dashed lines in FIG. 21 indicate the portions of the pulling string located beneath the skirt, and the solid lines indicate the portions of the pulling string located above the skirt. Since the pulling strings are not fixed on or thread through the stent, and thus other than the fixing band, the remaining portions of the skirt may serve as floating sections, the two sets of pulling strings may interact with each other via force transmitted by the skirt.

Twenty-Second Embodiment

Figure 22:
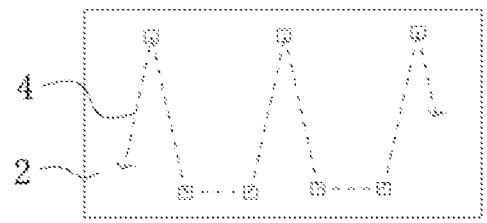
FIG. 22 illustrates how the pulling string of the stent apparatus according to the twenty-second embodiment of the present disclosure threads through the skirt.

Referring to FIG. 22, this embodiment differs from the twentieth embodiment in the wave shape of the undulation of the pulling string 4. In this embodiment, the pulling string follows a course having a wave shape with sharp peaks and flat valleys.

Twenty-Third Embodiment

Figure 23:
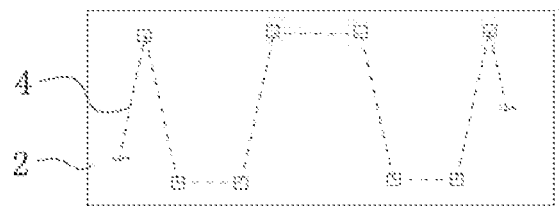
FIG. 23 illustrates how the pulling string of the stent apparatus according to the twenty-third embodiment of the present disclosure threads through the skirt.

Referring to FIG. 23, this embodiment differs from the twentieth embodiment in the wave shape of the undulation of the pulling string 4. In this embodiment, the pulling string follows a course having a wave shape with flat peaks and flat valleys.

Twenty-Fourth Embodiment

Figure 24:
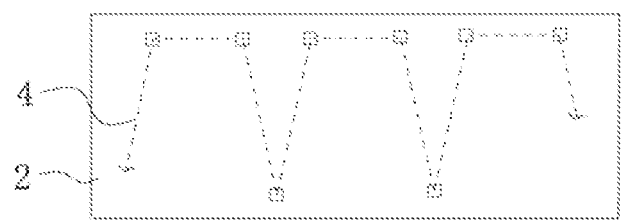
FIG. 24 illustrates how the pulling string of the stent apparatus according to the twenty-fourth embodiment of the present disclosure threads through the skirt.

Referring to FIG. 24, this embodiment differs from the twentieth embodiment in the wave shape of the undulation of the pulling string 4. In this embodiment, the pulling string follows a course having a wave shape with flat peaks and sharp valleys.

Twenty-Fifth Embodiment

Figure 25:
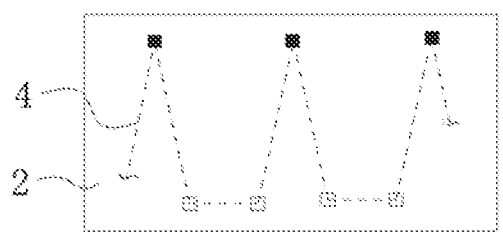
FIG. 25 illustrates how the pulling string of the stent apparatus according to the twenty-fifth embodiment of the present disclosure threads through the skirt.

Referring to FIG. 25, this embodiment differs from the twenty-second embodiment in that portions of the pulling string 4 corresponding to the peaks here are fixed on the skirt 2.

Twenty-Sixth Embodiment

Figure 26:
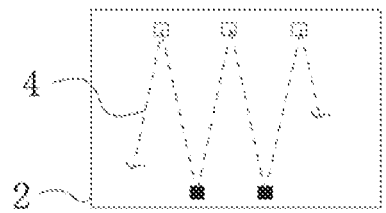
FIG. 26 illustrates how the pulling string of the stent apparatus according to the twenty-sixth embodiment threads through the skirt.

Referring to FIG. 26, this embodiment differs from the twentieth embodiment in that portions of the pulling string 4 corresponding to the valleys here are fixed on the skirt 2.

Twenty-Seventh Embodiment

Figure 27A:
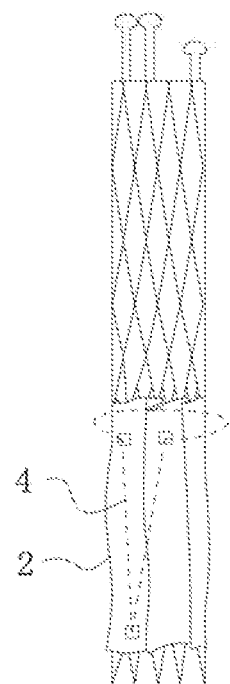
FIG. 27a illustrates how the pulling string of the stent apparatus according to the twenty-seventh embodiment of the present disclosure threads through the skirt.

Referring to FIG. 27*a*, this embodiment differs from the twentieth embodiment in that the pulling string 4 here is routed around the stent for less than a perimeter of the stent to form substantially an annular driving portion. Opposite ends of the driving portion movably thread through the skirt 2 respectively, and then extend downwards and join together to form a force exerting portion after movably threading through the bottom of the skirt. The annular driving portion may thread through the stent, or may be just surrounding the outer periphery of the stent. A single force exerting portion is provided as shown in FIG. 27*a*. Alternatively, more than one force exerting portion may be provided. It is also possible to provide a plurality of pulling strings 4, which pull the corresponding force exerting portions at the bottom of the skirt, respectively.

Figure 27B:
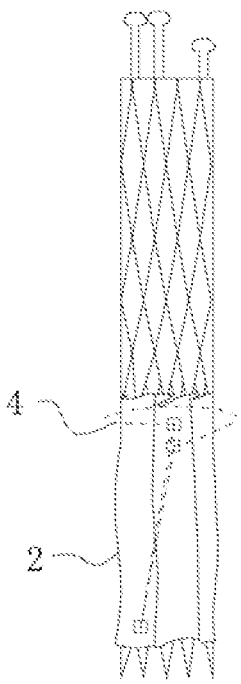
FIG. 27b shows how the pulling string threads through the skirt, wherein the pulling string has a different perimeter compared to that in the twenty-seventh embodiment.

Referring to FIG. 27*b*, in a further development, the pulling string 4 extends further in the circumferential direction compared to that shown in FIG. 27*a*. In particular, the pulling string 4 in this embodiment extends for the entire perimeter of the stent and forms an annular driving portion surrounding the stent.

Figure 27C:
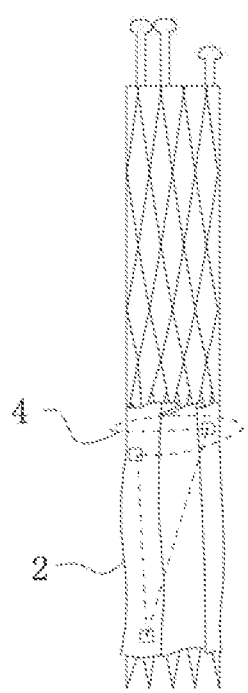
FIG. 27c shows how the pulling string threads through the skirt, wherein the pulling string has a different perimeter compared to that in the twenty-seventh embodiment.

Referring to FIG. 27*c*, in a further development, the pulling string 4 extends further in the circumferential direction compared to that shown in FIG. 27*a*. In particular, the pulling string 4 in this embodiment extends in the circumferential direction for 1.5 times of a perimeter of the stent, and forms an annular driving portion.

Twenty-Eighth Embodiment

Figure 28:
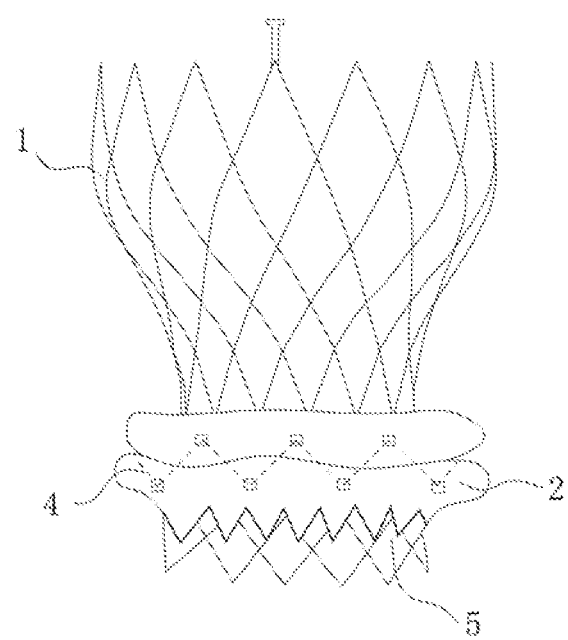
FIG. 28 is a schematic structural view of a stent apparatus according to a twenty-eighth embodiment of the present disclosure.

Referring to FIG. 28, in this embodiment, the outer periphery of the stent 1 is provided with a flexible skirt 2. Before the stent 1 is released, the skirt 2 is in an unfolded configuration, which is axially unfolded and surrounds the outer periphery of the stent 1 before release. After the stent 1 is released, the skirt 2 is folded and stacked along the axial direction of the stent 1 after release into a stacked configuration and forms an annular peripheral leakage occluder. Also provided is a pulling string 4 that is configured to drive the skirt 2 to transform into the stacked configuration. The pulling string 4 cooperates with the radial deformation of the stent during release. When being released in the human body, the bottom edge of the skirt 2 is released first, and the top edge of the skirt 2 is released later.

In this embodiment, the pulling string generally threads through the skirt in the circumferential direction. The pulling string undulates in the axial direction while extending in the circumferential direction, forming a wave-like configuration with peaks and valleys.

During the release of the stent, driven by the deformed stent, the peaks of the pulling string move away from each other in the circumferential direction and thus drive the valleys to lift upwardly. Since the pulling string movably threads through the skirt, the periodic portions thereof are configured for driving and operating in cooperation with one another, thereby generally moving the pulling string.

The top edge of the skirt 2 is fixed on the stent. The skirt 2 is provided with a plurality of cutting areas 5 at the bottom side of the skirt, arranged in the circumferential direction. The cutting areas may reduce the radial stacking thickness of the skirt in the unfolded configuration, facilitating loading onto the stent and delivery of the stent apparatus.

The bottom edge of the skirt 2 is generally in a tooth-shaped structure extending in the circumferential direction, with a cutting area formed between two adjacent teeth. In this embodiment, the teeth are triangular and evenly arranged in the circumferential direction.

Before the stent is released, the distal end of the skirt to be released first extends beyond the stent in the axial direction, and it is the tooth-shaped structure that extends beyond the stent.

Twenty-Ninth Embodiment

Figure 29:
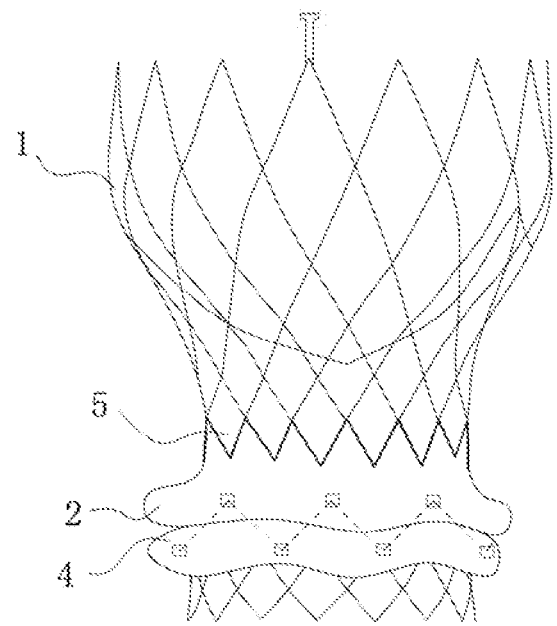
FIG. 29 is a schematic structural view of a stent apparatus according to a twenty-ninth embodiment of the present disclosure.

Referring to FIG. 29, this embodiment differs from the twenty-eighth embodiment in that the top edge of the skirt 2 here is fixed on the stent and has a plurality of cutting areas 5. The top edge of the skirt 2 corresponds to the edges of the grids of the stent, and is continuously stitched on the stent along the edges of the grids.

Thirtieth Embodiment

Figure 30:
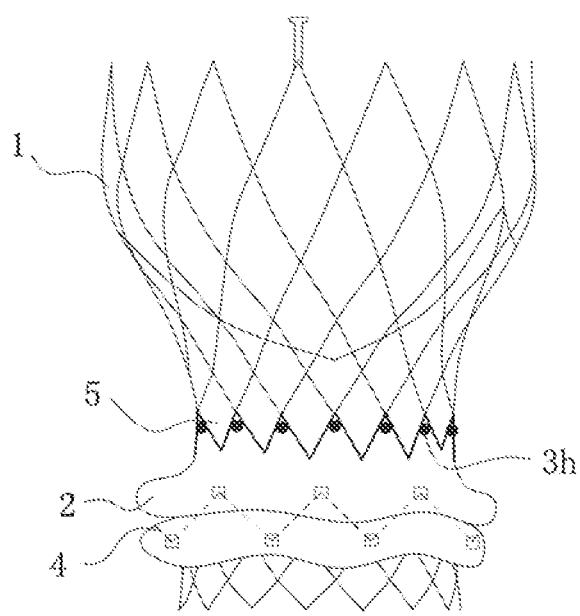
FIG. 30 is a schematic structural view of a stent apparatus according to a thirtieth embodiment of the present disclosure.

Referring to FIG. 30, the top edge of the skirt 2 has a tooth-shaped structure with triangular teeth. This embodiment differs from the twenty-ninth embodiment in that the top tips of the triangular teeth at the top edge of the skirt 2 are fixed on the stent with a plurality of fixing points 3*h* spaced from each other.

Thirty-First Embodiment

Figure 31:
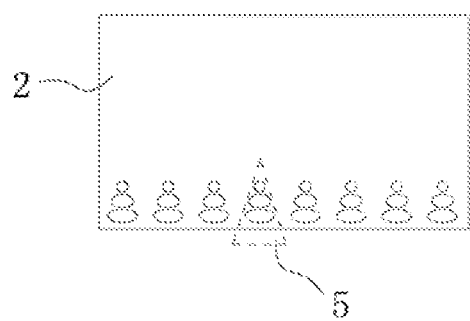
FIG. 31 is a schematic structural view showing cutting areas of a skirt of a stent apparatus according to a thirty-first embodiment of the present disclosure.

Referring to FIG. 31, this embodiment differs from the twenty-eighth embodiment in that each of the cutting areas 5 here includes a plurality of through holes arranged along the axial direction of the stent, with solid materials arranged between the through holes, which facilitates the overall shaping of the peripheral leakage occluder and maintenance of necessary pull at various areas.

The through hole may be in a circular or an elliptical shape. Among the through holes in the same cutting area, the closer to the corresponding side edge of the skirt, the larger the size of the through hole.

Thirty-Second Embodiment

Figure 32:
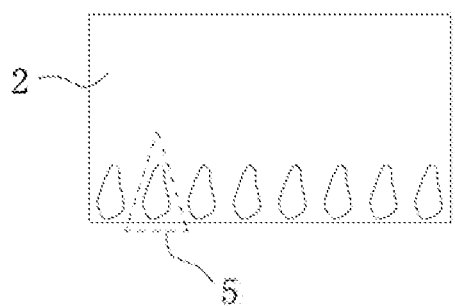
FIG. 32 is a schematic structural view showing cutting areas of a skirt of a stent apparatus according to a thirty-second embodiment of the present disclosure.

Referring to FIG. 32, this embodiment differs from the thirty-first embodiment in that the cutting area here includes a single through hole. The inner edge of the through hole is relatively smooth. The closer to the corresponding side edge of the skirt, the larger the width of the through hole.

Thirty-Third Embodiment

Figure 33:
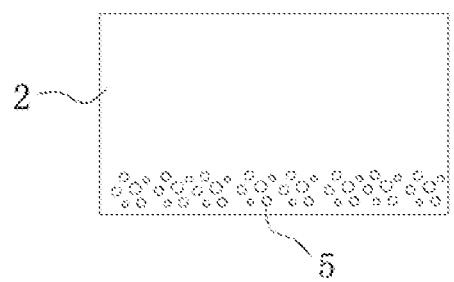
FIG. 33 is a schematic structural view showing cutting areas of a skirt of a stent apparatus according to a thirty-third embodiment of the present disclosure.

Referring to FIG. 33, this embodiment differs from the thirty-first embodiment in that there is no obvious boundary between the cutting areas 5 here, and the cutting areas 5 are provided with a plurality of through holes that are densely arranged.

Thirty-Fourth Embodiment

Figure 34:
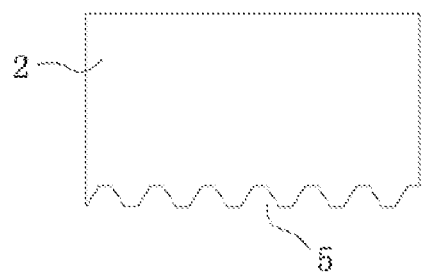
FIG. 34 is a schematic structural view showing cutting areas of a skirt of a stent apparatus according to a thirty-fourth embodiment of the present disclosure.

Referring to FIG. 34, this embodiment differs from the twenty-eighth embodiment in that the teeth between two adjacent cutting areas are trapezoid-shaped here.

Thirty-Fifth Embodiment

Figure 35:
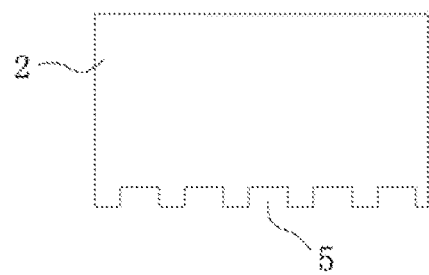
FIG. 35 is a schematic structural view showing cutting areas of a skirt of a stent apparatus according to a thirty-fifth embodiment of the present disclosure.

Referring to FIG. 35, this embodiment differs from the twenty-eighth embodiment in that the teeth between two adjacent cutting areas are rectangle-shaped here.

Thirty-Sixth Embodiment

Figure 36A:
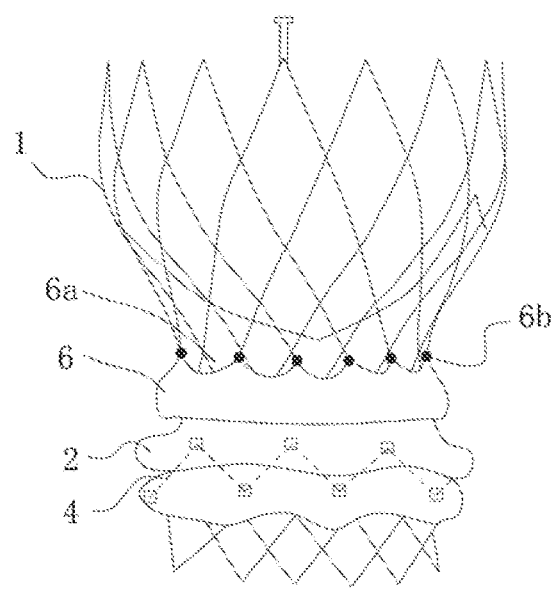
FIG. 36a is a schematic structural view of a stent apparatus according to a thirty-sixth embodiment of the present disclosure.

Referring to FIG. 36a, the outer periphery of the stent 1 in this embodiment is provided with a flexible skirt 2. Before the stent 1 is released, the skirt 2 is in an unfolded configuration, which is axially unfolded and surrounds the outer periphery of the stent 1 before release. After the stent 1 is released, the skirt 2 is folded and stacked along the axial direction of the stent 1 after release into a stacked configuration and forms an annular peripheral leakage occluder.

The top of the skirt is further provided with a blocking pocket 6 configured for receiving the back-flow blood from peripheral leakage. The blocking pocket 6 is made of flexible material such as the same material as the skirt. In this embodiment, the blocking pocket 6 is separately provided and has a double-layered structure, which may receive the back-flow blood from peripheral leakage and expand radially to abut against the annulus to further prevent the regurgitation. Alternatively, the blocking pocket 6 may be integrally formed with the skirt as a single piece; for example, the bottom of the blocking pocket 6 may be stitched on the stent to serve as a top fixing band of the skirt.

Alternatively, the coverage membrane provided inside the stent may also simultaneously serve as the blocking pocket. For example, a portion of the blocking pocket is integrally formed by the material of the skirt, and the other portion of the blocking pocket is formed by the material of the inner coverage membrane.

The blocking pocket 6 has inlets 6a for allowing back-flow blood to flow therein, by means of which the blocking pocket 6 is self-expandable to prevent further regurgitation. After the stent is released, the peripheral leakage occluder is located at the side of the blocking pocket 6 facing the bottom of the stent 1, and abuts against the blocking pocket 6 to operate in cooperation therewith.

The side of the blocking pocket 6 facing away from the top of the stent 1 is closed, and the opposite side thereof facing the top of the stent 1 is provided with a plurality of stitching portions 6b fixed to the stent 1. Adjacent stitching portions are spaced from each other, with an inlet 6a for allowing back-flow blood to flow therein defined therebetween. Therefore, a plurality of inlets are provided and the inlets are evenly arranged in the circumferential direction.

The peripheral leakage occluder in this embodiment may be formed in any technique described in the above embodiments. For example, the skirt 2 may be driven to transform into the stacked configuration by an optional pulling string 4, which cooperates with the radial deformation of the stent 1 during release. When being released in the human body, the bottom edge of the skirt 2 is released first, and the top edge of the skirt 2 is released later.

In this embodiment, the pulling string generally threads through the skirt in the circumferential direction. The pulling string undulates in the axial direction while extending in the circumferential direction, forming a wave-like configuration with peaks and valleys. The peaks are located at the top edge of the skirt 2 and fixed on the stent together with the skirt 2. The valleys movably thread through the skirt 2.

During the release of the stent, driven by the deformed stent, the peaks of the pulling string move away from each other in the circumferential direction and thus drive the valleys to lift upwardly.

Figure 36B:
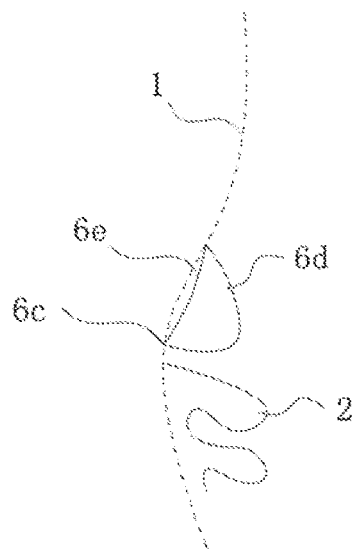
FIG. 36b is a schematic structural view showing a part of a blocking pocket of the stent apparatus according to the thirty-sixth embodiment.

Referring to FIG. 36b, which schematically illustrates a cross section of the blocking pocket 6, the dashed line indicates the stent 1, and the blocking pocket 6 is separately provided relative to the material of the skirt 2. The blocking pocket 6 has a double-layered structure including an inner layer 6e and an outer layer 6d. The two layers 6e and 6d may be formed as one single piece. The two layers are integrally connected with a bend at the bottom. In this embodiment, the inner layer 6e and the outer layer 6d are separately formed, and are connected and sealed by stitching the bottoms 6c together.

Thirty-Seventh Embodiment

Figure 37:
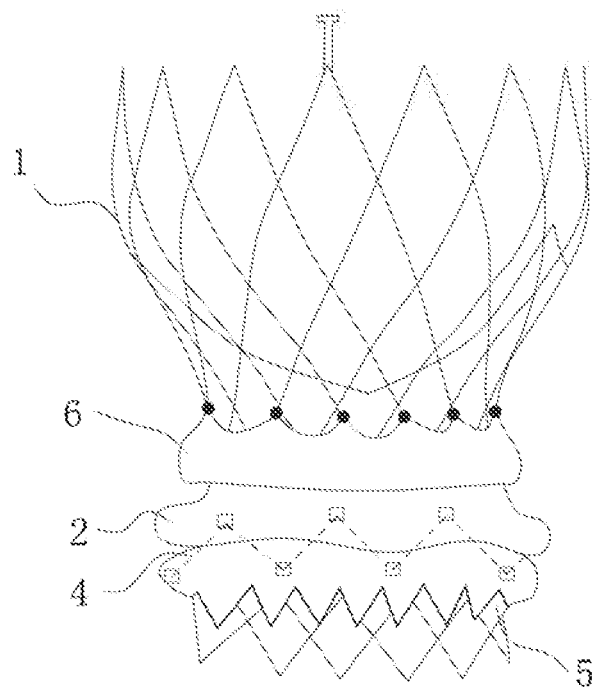
FIG. 37 is a schematic structural view of a stent apparatus according to a thirty-seventh embodiment of the present disclosure.

Referring to FIG. 37, this embodiment differs from the thirty-sixth embodiment in that the skirt 2 here is provided with a plurality of cutting areas 5 at the axial bottom side of the skirt, arranged in the circumferential direction. The cutting areas may reduce the radial stacking thickness of the skirt in the unfolded configuration, facilitating the load and delivery. The bottom edge of the skirt 2 is generally in a tooth-shaped structure extending in the circumferential direction, with a cutting area formed between two adjacent teeth. The teeth are triangular and evenly arranged in the circumferential direction. Before the stent is released, the distal end of the skirt to be released first extends beyond the stent in the axial direction, and it is the tooth-shaped structure that extends beyond the stent.

Thirty-Eighth Embodiment

Figure 38:
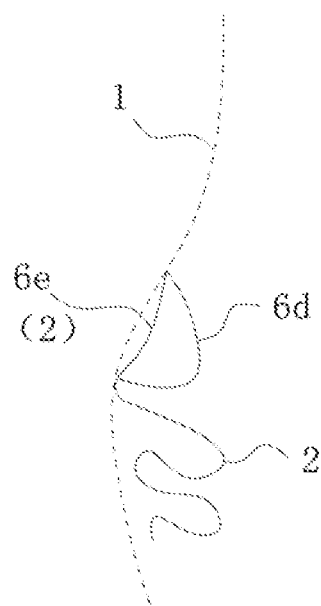
FIG. 38 is a schematic structural view showing a part of a blocking pocket of a stent apparatus according to a thirty-eighth embodiment of the present disclosure.

Referring to FIG. 38, the dashed line indicates the stent 1. This embodiment differs from the thirty-sixth embodiment in that the inner layer 6e of the blocking pocket here is integrally formed by a top material of the skirt which extends upwardly, and the outer layer 6d of the blocking pocket is a separate piece.

Thirty-Ninth Embodiment

Figure 39:
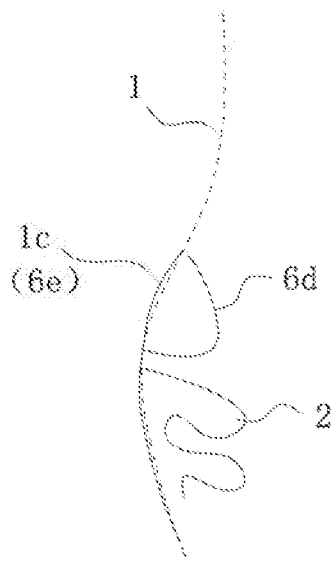
FIG. 39 is a schematic structural view showing a part of a blocking pocket of a stent apparatus according to a thirty-ninth embodiment of the present disclosure.

Referring to FIG. 39, the dashed line indicates the stent 1. Different from the thirty-sixth embodiment, in this embodiment, an inner coverage membrane 1c is provided at the inner wall of the stent 1, which simultaneously serves as the inner layer 6e. The outer layer 6d of the blocking pocket is a separate piece.

Fortieth Embodiment

Figure 40:
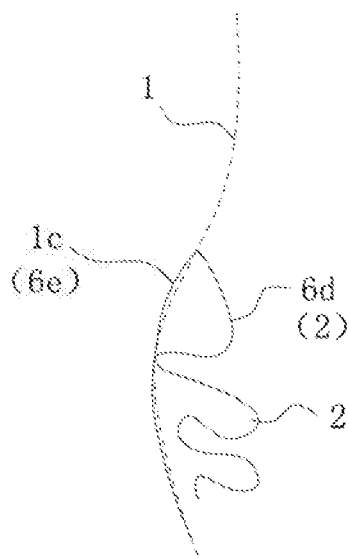
FIG. 40 is a schematic structural view showing a part of a blocking pocket of a stent apparatus according to a fortieth embodiment of the present disclosure.

Referring to FIG. 40, the dashed line indicates the stent 1. Different from the thirty-sixth embodiment, in this embodiment, an inner coverage membrane 1c is provided at the inner wall of the stent 1, which simultaneously serves as the inner layer 6e of the blocking pocket. The outer layer 6d of the blocking pocket is formed by a top material of the skirt 2 which extends upwardly.

Forty-First Embodiment

Figure 41A:
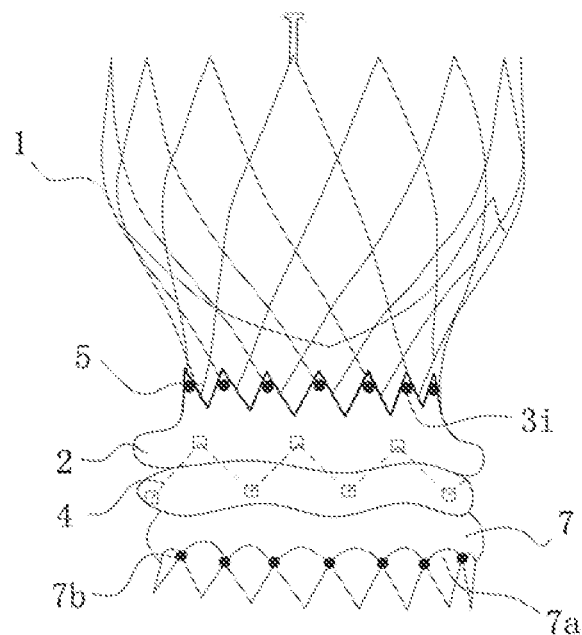
FIG. 41a is a schematic structural view of a stent apparatus according to a forty-first embodiment of the present disclosure.

Referring to FIG. 41a, in this embodiment, the outer periphery of the stent 1 is provided with a flexible skirt 2. Before the stent 1 is released, the skirt 2 is in an unfolded configuration, which is axially unfolded and surrounds the outer periphery of the stent 1 before release. After the stent 1 is released, the skirt 2 is folded and stacked along the axial direction of the stent 1 after release into a stacked configuration and forms an annular peripheral leakage occluder. Also provided is a pulling string 4 that is configured to drive the skirt 2 to transform into the stacked configuration. The pulling string 4 cooperates with radial deformation of the stent during release. The top edge of the skirt 2 has a tooth-shaped structure with triangular teeth, and the top tips of the triangular teeth are fixed on the stent with a plurality of fixing points 3i spaced from each other. The lower portion of the skirt 2 is a floating section. When being released in the human body, the bottom edge of the skirt 2 is released first, and the top edge of the skirt 2 is released later.

In this embodiment, the pulling string generally threads through the skirt in the circumferential direction. The pulling string undulates in the axial direction while extending in the circumferential direction, forming a wave-like configuration with peaks and valleys. The peaks are located at the top edge of the skirt 2. Both peaks and valleys movably thread through the skirt 2. However, the pulling string does not thread through the stent. During the release of the stent, driven by the deformed stent, the peaks move away from each other in the circumferential direction and thus drive the valleys to lift upwardly.

The normal blood inflow side of the stent 1, i.e., the bottom end thereof, is surrounded by a pushing pocket 7 for facilitating the skirt 2 to transform into the stacked configuration. The pushing pocket 7 has inlets for allowing blood to flow in, such that the pushing pocket 7 is self-expandable to push the skirt. The pushing pocket is made of flexible material, which may be the same material as the skirt. The pushing pocket has a double-layered structure, so it can be filled with blood and expanded radially.

One side of the pushing pocket 7 is closed, and the other side is provided with a plurality of stitching portions 7b fixed to the stent 1. Adjacent stitching portions are spaced from each other, with an inlet defined therebetween. Therefore, a plurality of inlets 7a for allowing back-flow blood to flow therein are provided in this embodiment, which are evenly arranged along the circumferential direction. In an unfolded configuration of the skirt, the bottom edge of the skirt extends beyond the pushing pocket, so that the bottom edge of the skirt covers the pushing pocket 7 fully or partially.

Figure 41B:
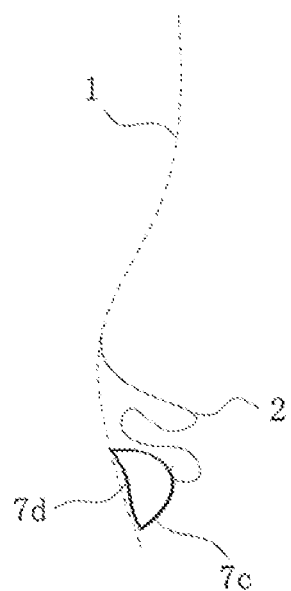
FIG. 41b is a schematic structural view showing a part of a pushing pocket of the stent apparatus according to the forty-first embodiment.

Referring to FIG. 41b, which schematically illustrates a cross section of the pushing pocket 7, the dashed line indicates the stent 1. The pushing pocket 7 is separately provided with respect to the material of the skirt 2. The pushing pocket 7 has a double-layered structure, including an inner layer 7d and an outer layer 7c. The two layers 7d and 7c may be formed as one single piece. The two layers are integrally connected with a bend at the bottom. In this embodiment, the inner layer 7d and the outer layer 7c are separately formed, and are connected and sealed by stitching the tops together.

Forty-Second Embodiment

Figure 42:
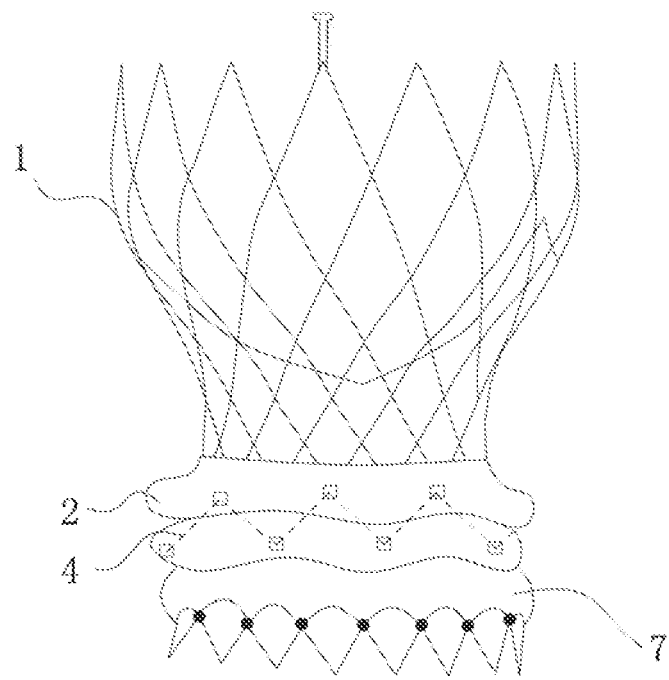
FIG. 42 is a schematic structural view of a stent apparatus according to a forty-second embodiment of the present disclosure.

Referring to FIG. 42, this embodiment differs from the forty-first embodiment in that the skirt 2 does not have a tooth-shaped structure at the top edge.

Forty-Third Embodiment

Figure 43:
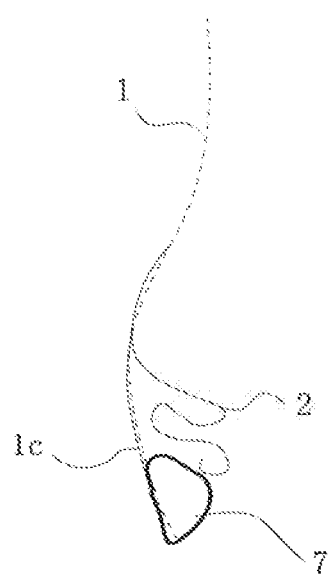
FIG. 43 is a schematic structural view showing a part of a pushing pocket of a stent apparatus according to a forty-third embodiment of the present disclosure.

Referring to FIG. 43, the dashed line indicates the stent 1. Different from the forty-first embodiment, in this embodiment, an inner coverage membrane 1c is provided at the inner wall of the stent 1, the material of which is turned outwards and folded to form the pushing pocket 7.

Forty-Fourth Embodiment

Figure 44:
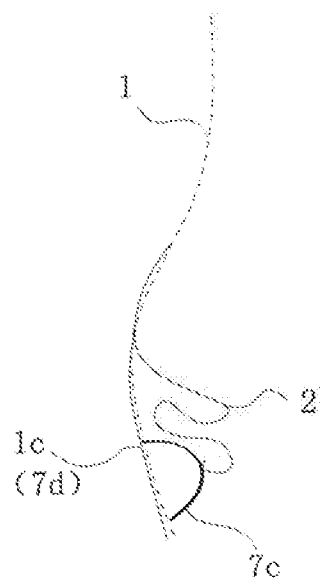
FIG. 44 is a schematic structural view showing a part of a pushing pocket of a stent apparatus according to a forty-fourth embodiment of the present disclosure.

Referring to FIG. 44, the dashed line indicates the stent 1. Different from the forty-first embodiment, in this embodiment, an inner coverage membrane 1c is provided at the inner wall of the stent 1, which simultaneously serves as the inner layer 7d of the pushing pocket 7. The outer layer 7c of the pushing pocket 7 is separately provided. A top edge of the outer layer 7c is stitched and sealed to the corresponding portion of the inner coverage membrane 1c.

Forty-Fifth Embodiment

Figure 45A:
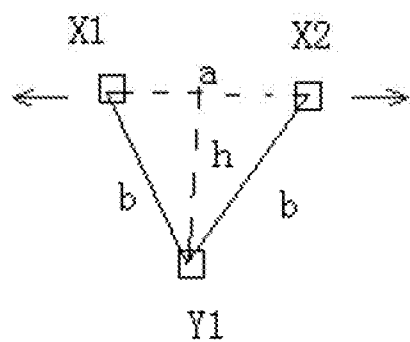
FIG. 45a is a schematic diagram showing the relationship between the circumferential distance variation between a first acting portion and a second acting portion and the axial displacement of a force exerting portion according to a forty-fifth embodiment of the present disclosure.
Figure 45B:
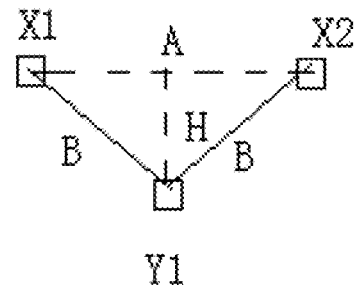
FIG. 45b is a schematic diagram showing the relationship between the circumferential distance variation between the first acting portion and the second acting portion and the axial displacement of the force exerting portion according to the forty-fifth embodiment after the shape of a pulling unit is changed.

As shown in FIGS. 45a and 45b, in this embodiment, a single pulling unit is taken as an example for illustration. Assuming that the length of the pulling string is I, the distance between the first acting portion X1 and the second acting portion X2 before being pulled is a, and the distance between the force exerting portion Y1 and a line connecting the first acting portion X1 and the second acting portion X2 before being pulled is h.

Before being pulled, the distance between the first acting portion X1 and the force exerting portion Y1 is b.

Before being pulled, the distance between the second acting portion X2 and the force exerting portion Y1 is b.

Before being pulled, the overall length of the pulling string of the pulling unit in FIG. 45a is 2b, where 2b=I.

After being pulled, the distance between the first acting portion X1 and the second acting portion X2 is A, and the distance between the force exerting portion Y1 and a line connecting the first acting portion X1 and the second acting portion X2 is H.

After being pulled, the distance between the first acting portion X1 and the force exerting portion Y1 is B.

After being pulled, the distance between the second acting portion X2 and the force exerting portion Y1 is B.

After being pulled, the overall length of the pulling string of the pulling unit in FIG. 45b is 2B, where 2B=I.

After being pulled, the circumferential distance variation between the first acting portion and the second acting portion is Δa, where Δa=A−a. The axial distance variation of the force exerting portion Y1 before and after being pulled is:

$$\Delta h = h - H = \sqrt{b^2 - \left(\frac{a}{2}\right)^2} - \sqrt{B^2 - \left(\frac{A}{2}\right)^2}$$

$$= \sqrt{\left(\frac{l}{2}\right)^2 - \left(\frac{a}{2}\right)^2} - \sqrt{\left(\frac{l}{2}\right)^2 - \left(\frac{A}{2}\right)^2}$$

$$= \frac{\sqrt{l^2 - a^2} - \sqrt{l^2 - A^2}}{2}$$

$$= \frac{\sqrt{l^2 - a^2} - \sqrt{l^2 - (a + \Delta a)^2}}{2}$$

It can be seen that the axial pulling length of the pulling unit is closely related to the circumferential distance variation between the first acting portion and the second acting portion. In most cases, the circumferential distance variation of the pulling string from the unfolded configuration to the stacked configuration is less than a perimeter of the stent.

Figure 45C:
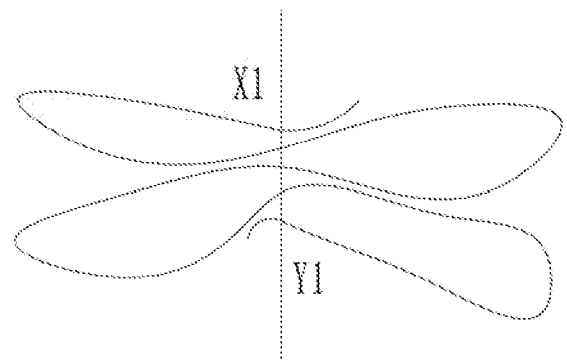
FIG. 45c is a schematic diagram showing the thickness of a peripheral leakage occluder after a skirt is folded according to the forty-fifth embodiment.

The thickness of the peripheral leakage occluder after being folded is related to the number of folds. Referring to FIG. 45c, assuming that there are three threading holes between the first acting portion X1 and the force exerting portion Y1, if the pulling string is tensioned, five layers of folds will be formed.

In a further development, the stent apparatus is a balloon expandable stent, with the stent pre-compressed onto the balloon. During release, the balloon is expanded by injected saline solution to expand the stent. With reference to FIGS. 45a and 45b, the skirt is stitched on the stent, and when the whole stent is expanded, the distance between the first action portion X1 and the second action portion X2 increases, which pulls the force application portion Y1 to move axially.

Forty-Sixth Embodiment

Figure 46A:
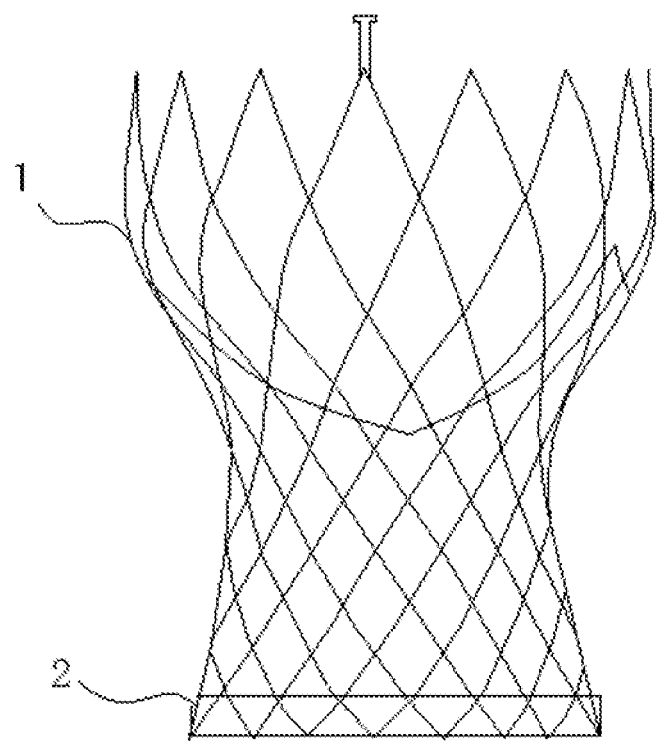
FIGS. 46a to 46c are schematic diagrams according to a forty-sixth embodiment of the present disclosure.
Figure 46B:
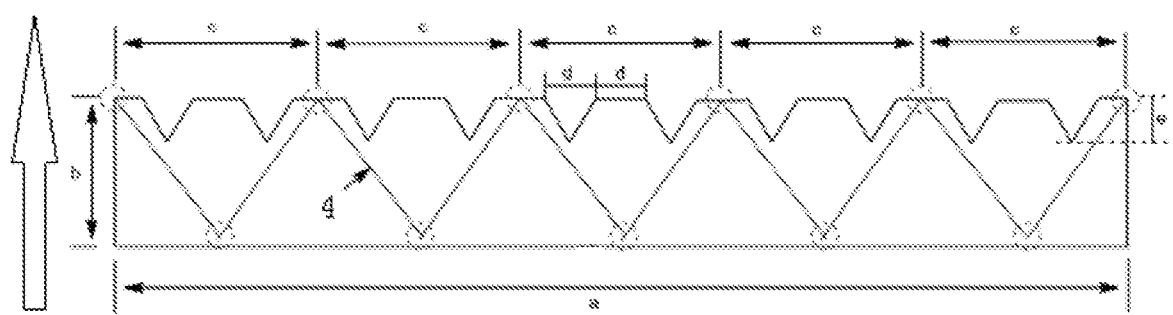
Figure 46C:
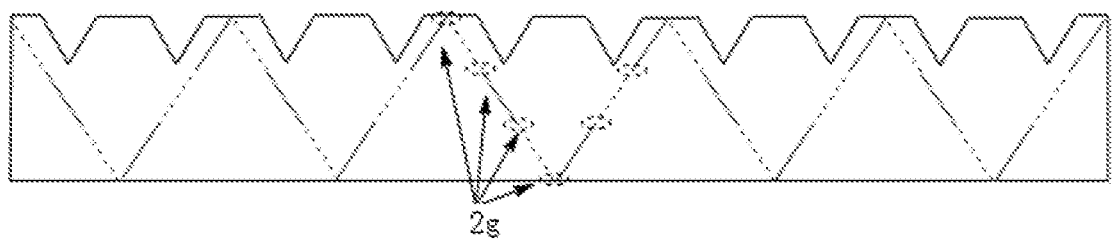
Figure 47A:
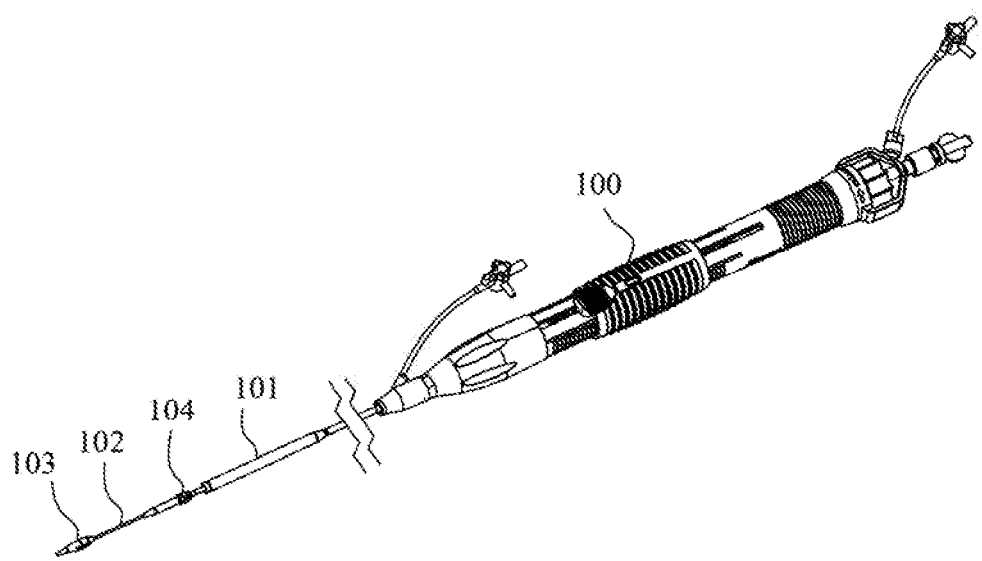
FIG. 47a is a schematic diagram of a delivery system according to a forty-seventh embodiment of the present disclosure.
Figure 47B:
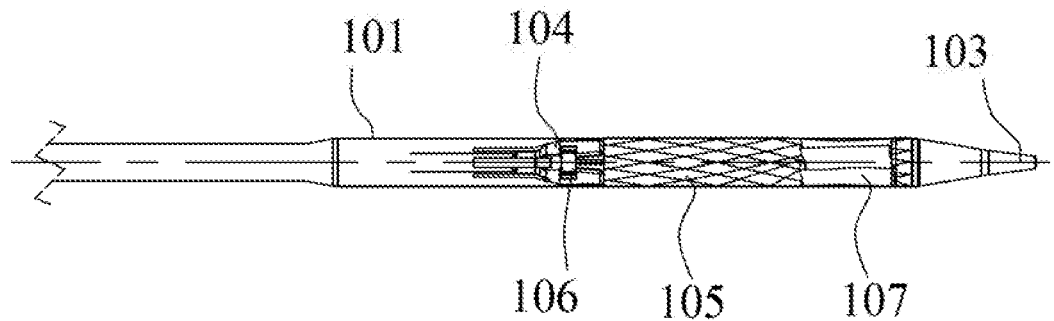
FIG. 47b is a schematic view according to the forty-seventh embodiment, in which a stent with a skirt is in a loaded configuration.
Figure 47C:
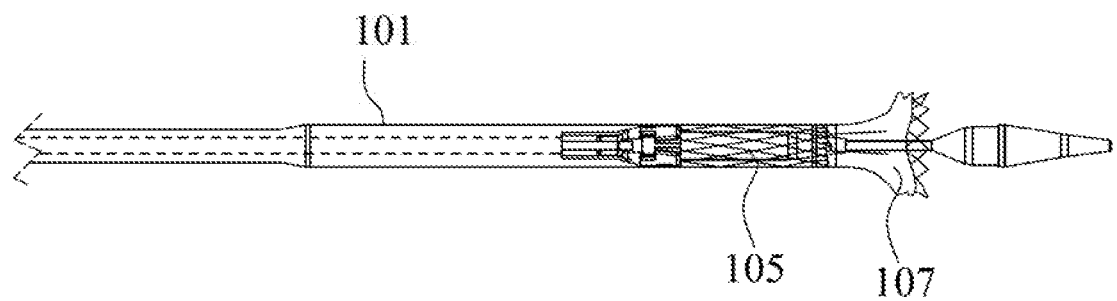
FIG. 47c is a schematic view according to the forty-seventh embodiment, in which the stent with the skirt is in an intermediate state during release.
Figure 47D:
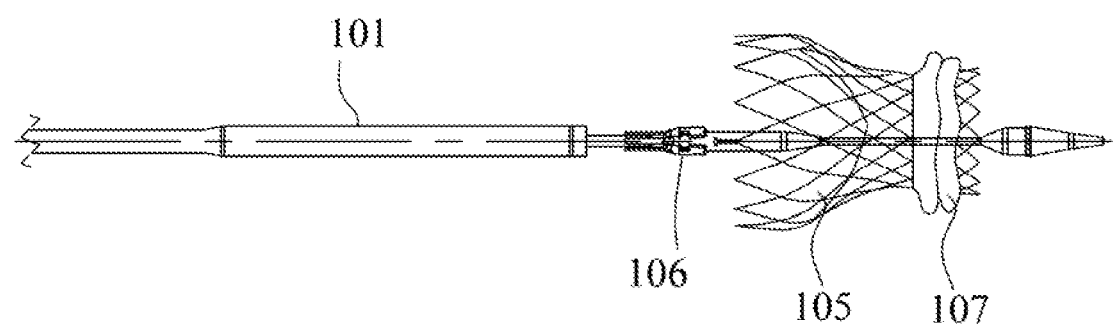
FIG. 47d is a schematic view according to the forty-seventh embodiment, in which the stent with the skirt is in a released configuration.
Figure 47E:
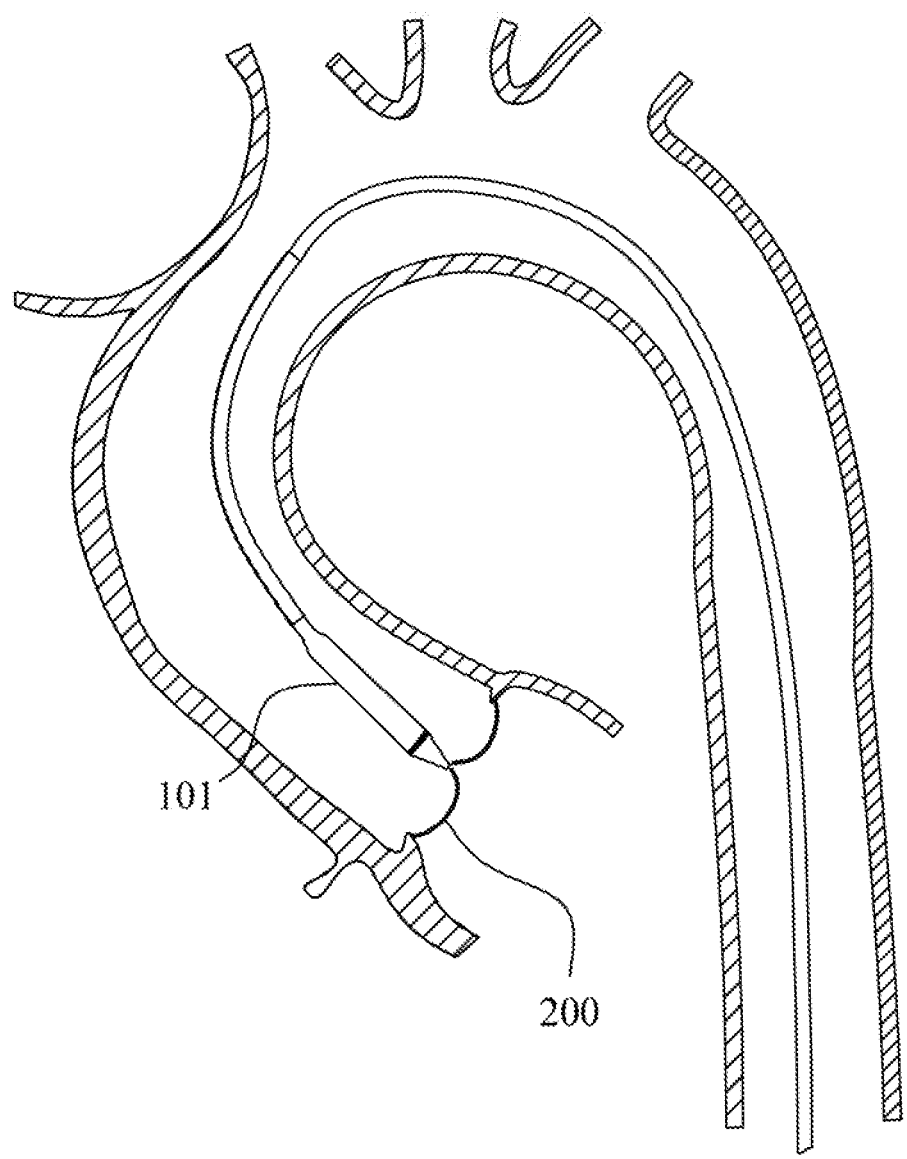
FIG. 47e is a schematic view according to the forty-seventh embodiment, showing the delivery system entering into the aortic valve.
Figure 47F:
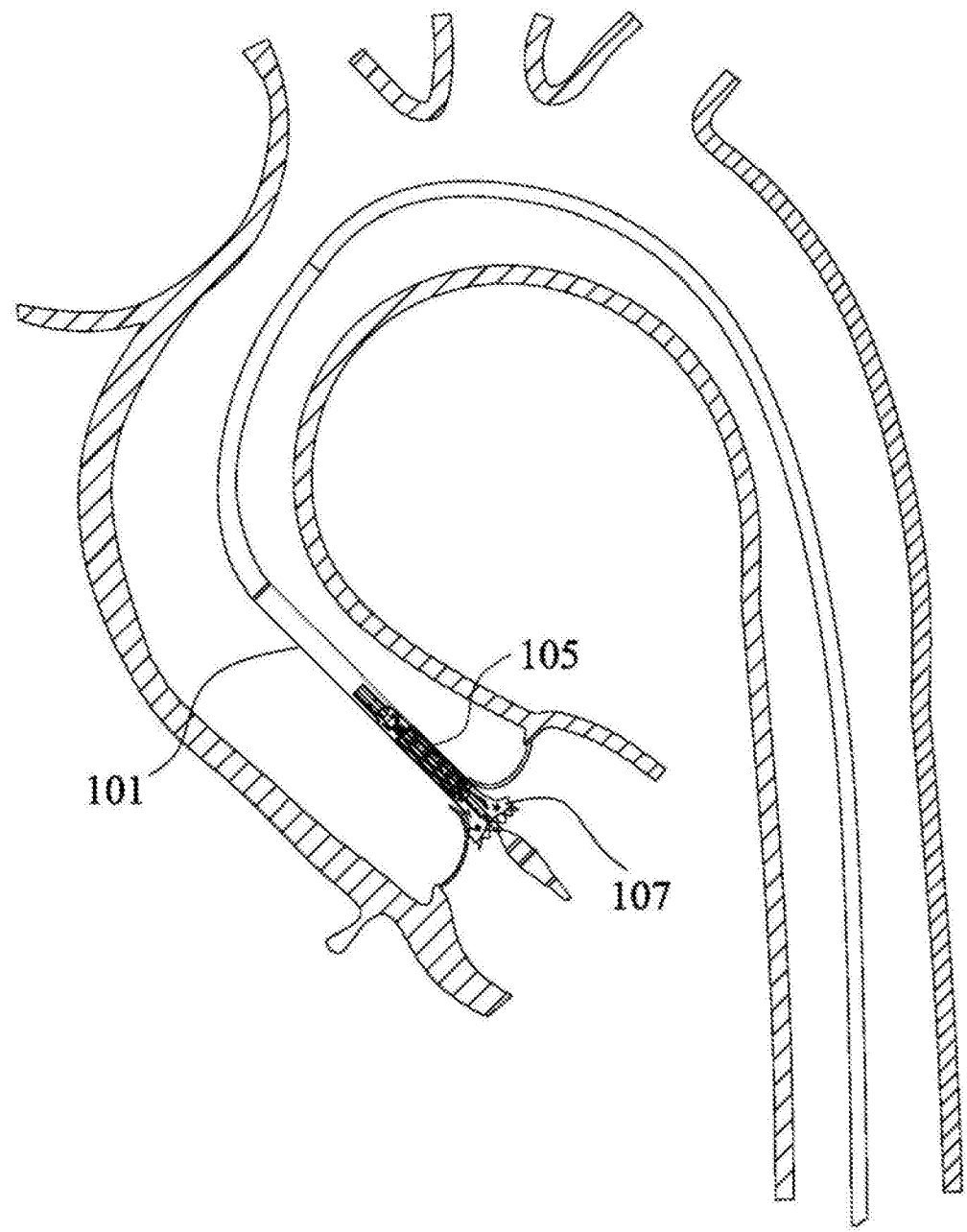
FIG. 47f is a schematic view according to the forty-seventh embodiment, in which the stent in the delivery system is being released to an intermediate state at the aortic valve.
Figure 47G:
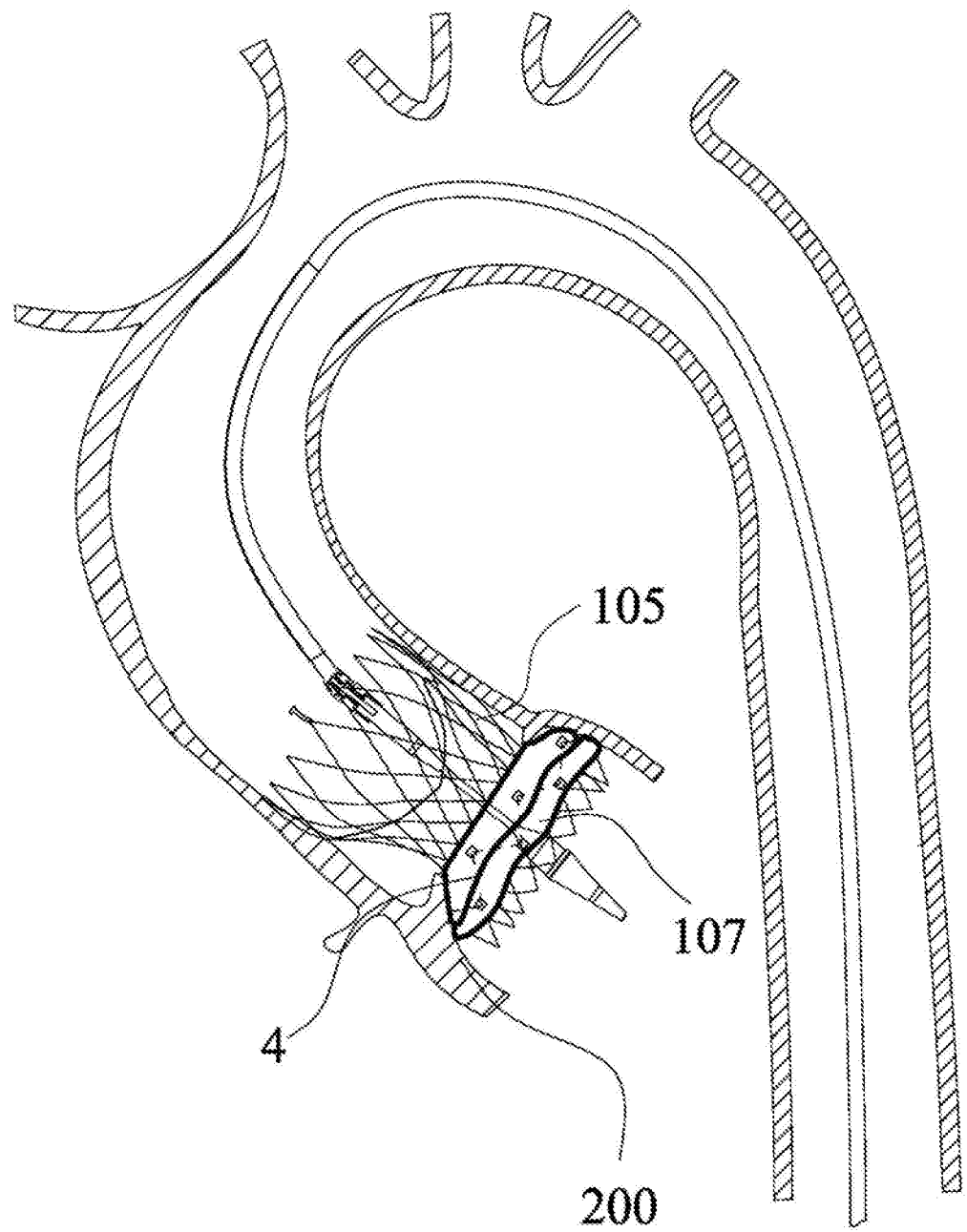
FIG. 47g is a schematic view according to the forty-seventh embodiment, in which the stent in the delivery system is fully released at the aortic valve.

Referring to FIGS. 46a to 46c, in this embodiment, the outer periphery of the stent 1 is provided with a flexible skirt 2. Before the stent 1 is released, the skirt 2 is in an unfolded configuration, which is axially unfolded and surrounds the outer periphery of the stent 1 before release. After the stent 1 is released, the skirt 2 is folded and stacked along the axial direction of the stent 1 after release into a stacked configuration and forms an annular peripheral leakage occluder. Also provided is a pulling string 4 that is configured to drive the skirt 2 to transform into the stacked configuration. The pulling string 4 cooperates with radial deformation of the stent 1 during release. When being released in the human body, the bottom edge of the skirt 2 is released first, and the top edge of the skirt 2 is released later.

FIG. 46a only illustrates the position of the skirt 2, in which the skirt 2 is substantially located at one axial end of the stent 1 which is adjacent to the blood inflow side (the direction of the hollow arrow in FIG. 46b indicates the normal blood flow direction when the stent is in use). The stent 1 has a meshed structure, for example, having a plurality of grids as shown in the figures. The axial length of the skirt in the unfolded configuration is half of the axial length of a grid.

The top edge of the skirt 2 is fixed on the stent, and the skirt 2 is provided with a plurality of cutting areas 5 at the axial top side thereof, arranged in the circumferential direction. The cutting areas may reduce the radial stacking thickness of the skirt in the unfolded configuration, facilitating the load and delivery. The top edge of the skirt 2 is generally in a tooth-shaped structure extending in the circumferential direction, with a cutting area formed between two adjacent teeth, and the teeth are triangular or trapezoidal and evenly arranged in the circumferential direction.

In the case that the top edge of the skirt 2 is fixed on the stent, stitching portions may be provided only at a middle portion of the top edge of the tooth-shaped structure, with the stitching portions circumferentially spaced from each other. Developing points are provided on the stent at the stitching portions.

In this embodiment, the pulling string generally threads through the skirt in the circumferential direction. The pulling string undulates in the axial direction while extending in the circumferential direction, forming a wave-like configuration with peaks and valleys.

During the release of the stent, driven by the deformed stent, the peaks of the pulling string move away from each other in the circumferential direction and thus drive the valleys to lift upwardly. Since the pulling string movably threads through the skirt, the periodic portions thereof are configured for driving and operating in cooperation with one another, thereby generally moving the pulling string.

The portions indicated by broken line circles in the figures may serve as the threading holes 2g. The pulling string 4 only threads through the skirt, into and out of the threading holes.

In a further development, the pulling string may thread through the stent at the uppermost threading holes in the figure, which also serves as the stitching portions and thus maintains the axial position of the skirt relative to the stent.

In an unfolded configuration of the skirt, the skirt has a length indicated as a that is substantially equal to the perimeter of a corresponding portion of the stent, and the skirt has a width b which is half of the height of a grid of the stent. The length of the skirt is evenly divided into five parts, with the length of each part being c. The length of each part is equal to the length of two complete teeth. In other words, there are 10 teeth in total. Each tooth has a length d (the upper side of the trapezoid) which is equal to a distance between two adjacent teeth d. The width of the skirt is evenly divided into four parts, with the length of each part being e. The height of each tooth is e.

In the stacked configuration, each pulling unit may be folded for three times (fold is generated between two adjacent threading holes in the axial direction) to form a four-layered stack provided that a plurality of threading holes 2g are provided. By providing a plurality of threading holes, the position limiting between the pulling string and the skirt can be increased, so that the skirt can be stacked more uniformly when the skirt is pulled.

Specifically, taking a specific valve as an example, the skirt has a length a, where a=95 mm±0.2 mm, and the skirt has a width b, where b=8.80 mm±0.2 mm.

The length of the skirt may be divided into five parts, with the length of each part being c, where c=95/5=19 mm±0.2 mm.

The tooth has a length d, and the distance between two adjacent teeth is also d, where d=19/4=4.75 mm±0.2 mm.

Each tooth has a height e, where e=8.81/4=2.2 mm±0.2 mm.

Forth-Seventh Embodiment

Referring to FIGS. 47a to 47g, a delivery system is provided in this embodiment, which includes a handle 100, a core shaft 102 connected to the handle 100, and a sheath 101 slidably surrounding the outer periphery of the core shaft 102. The sheath 101 is able to slide axially relative to the core shaft 102 under the control of the handle 100. The distal end of the core shaft 102 is provided with a guide head 103 and a mounting head 104 adjacent to the guide head 103. The mounting head 104 is provided with a plurality of slots or protrusions for connecting with an implanted instrument. The implanting instrument may be, for example, the stent 105 with the skirt 107 in the above embodiments. The proximal end of the stent 105 is provided with a fixing ear 106 for engaging with the mounting head 104. In a loaded state, the stent 105 is radially compressed, located between the guide head 103 and the mounting head 104, and constrained by the sheath 101. Correspondingly, the skirt is in an unfolded configuration, and arranged around the outer periphery of the stent 105.

After the stent 105 is delivered to a desired position in the human body such as a lesion site near the aortic valve 200 by the delivery system, the sheath 101 is withdrawn relative to the core shaft 102, and the distal end of the stent 105 is first released, and is gradually exposed and begins to expand radially. Under the action of the stent 105 itself or in combination with the pulling string, the skirt 107 begins to be axially pulled and stacked. After the stent 105 is completely released, the skirt 107 transitions into a stacked configuration and forms a peripheral leakage occluder, further preventing the regurgitation at the aortic valve 200.

The embodiments of the present invention may be combined with each other without technical conflicts. The related principles and synergistic effects may be referred to the related description of the summary of the invention.

The above disclosure is only specific embodiments of the present invention, but the present invention is not limited thereto. Those skilled in the art may make various modifications and variations to the present invention without departing from the spirit and scope of the present invention. Obviously, these modifications and variations should fall into the protection scope claimed by the present invention. In addition, although some specific terms are used in this specification, these terms are just for convenience of illustration and do not constitute any special limitation to the present invention.

What is claimed is:

1. A stent apparatus with a self-folded skirt, comprising a stent which has a first configuration before being released and a second configuration after being released that is different from the first configuration, characterized by the stent apparatus having a flexible skirt, wherein the flexible skirt has:
   an unfolded configuration, in which the skirt is axially unfolded and surrounds an outer periphery of the stent before being released;
   a stacked configuration, in which the skirt is folded and stacked in an axial direction of the stent after being released and forms an annular peripheral leakage occluder;
   wherein at least a portion of the skirt is fixed on the stent, and the stent apparatus is further provided with a pulling string that only threads though the skirt, wherein the pulling string undulates in the axial direction of the stent while extending in a circumferential direction of the stent, thereby forming a wave-like configuration, and a wave shape of the pulling string is changed when the pulling string is driven by deforming the stent during release so as to pull the skirt into the stacked configuration.

2. The stent apparatus with a self-folded skirt according to claim 1, wherein a portion of the skirt in the axial direction is configured as a fixing band which is stitched on the stent; and the fixing band is stitched on the stent in a circumferential direction continuously or discontinuously with intervals.

3. The stent apparatus with a self-folded skirt according to claim 2, wherein,
   at least one section of the skirt in the axial direction is configured as a floating section around the outer periphery of the stent, and the floating section is folded axially in the stacked configuration of the skirt; and wherein,
   both axial sides of the floating section are configured as fixing bands; or
   one axial side of the floating section is configured as a fixing band, and the other axial side of the floating section is floatable.

4. The stent apparatus with a self-folded skirt according to claim 3, wherein,
   a proximal end of the skirt which is to be released later is fixed on the stent, and a distal end of the skirt which is to be released first floats around the outer periphery of the stent; or
   a distal end of the skirt which is to be released first is fixed on the stent, and a proximal end of the skirt which is to be released later floats around the outer periphery of the stent.

5. The stent apparatus with a self-folded skirt according to claim 4, wherein,
   one section of the stent in the axial direction is configured as a flared driving structure that is configured to drive the skirt to be folded and stacked; and the flared driving structure extends to a distal end of the stent which is to be released first.

6. The stent apparatus with a self-folded skirt according to claim 1, wherein,
   at least one section of the skirt in the axial direction is configured as a floating section around the outer periphery of the stent.

7. The stent apparatus with a self-folded skirt according to claim 6, wherein,
   the floating section has two axial edges, one of which is fixed on the stent, and the other serves as a floating edge; or
   both of the two axial edges of the floating section are fixed on the stent.

8. The stent apparatus with a self-folded skirt according to claim 6, wherein,
   the pulling string which serves to act on the floating section comprises one or more pulling units, and each pulling unit includes at least two threading ends interacting with the skirt, a circumferential span between the two threading ends changes after the stent is released relative to the stent being unreleased, and
   at least one force exerting portion is formed by at least a part of the pulling unit between the two threading ends and connected to the skirt, and a relative displacement in the axial direction of the stent between the force exerting portion and the threading ends is produced during the release of the stent to pull the skirt to be stacked.

9. The stent apparatus with a self-folded skirt according to claim 8, wherein,
the at least one force exerting portion is fixed on the skirt or movably threads through the skirt.

10. The stent apparatus with a self-folded skirt according to claim 8, wherein,
the at least one force exerting portion comprises a plurality of force exerting portions which are distributed continuously or discontinuously with intervals therebetween; wherein,
when the force exerting portions of the pulling string are distributed discontinuously, force is transmitted across the intervals through the skirt.

11. The stent apparatus with a self-folded skirt according to claim 7, wherein,
the skirt is provided with one or more threading holes, and the at least one force exerting portion movably threads through the one or more the threading holes; and
at least one of the one or more threading holes is arranged offset from a line connecting the two threading ends.

12. The stent apparatus with a self-folded skirt according to claim 7, wherein,
the force exerting portion is located between the two threading ends along an extension direction of the pulling string.

13. The stent apparatus with a self-folded skirt according to claim 7, wherein,
the two threading ends extend along two sides of a V-shaped course respectively and join together at the force exerting portion, and the two threading ends pull a vertex of the V-shaped course to move axially during the deforming of the stent.

14. The stent apparatus with a self-folded skirt according to claim 1, wherein,
the wave-like configuration has one or more waves and each wave has a triangle, trapezoid, rectangle or arc shape.

15. The stent apparatus with a self-folded skirt according to claim 1, wherein,
the skirt is provided with a first set of threading holes and a second set of threading holes, with each set of threading holes comprising a plurality of threading holes arranged in a circumferential direction, the two set of threading holes are arranged one above the other in the axial direction, and the pulling string threads through the first set of threading holes and the second set of threading holes in an alternating manner and forms the wave-like configuration.

16. The stent apparatus with a self-folded skirt according to claim 15, wherein,
the pulling string threads into and out of the surfaces of the skirt in an alternating manner.

17. The stent apparatus with a self-folded skirt according to claim 16, wherein,
the two sets of threading holes have the same number of threading holes and the threading holes of the first set are arranged offset from the threading holes of the second set.

18. The stent apparatus with a self-folded skirt according to claim 1, wherein,
the skirt is made of a flexible material and constrains around the outer periphery of the stent in a released configuration.

19. The stent apparatus with a self-folded skirt according to claim 1, wherein,
the skirt is made of a porcine pericardium, or a bovine pericardium, or other flexible biocompatible materials.

20. A heart valve, comprising the stent apparatus with a skirt according to claim 1, the stent is provided with a valve and/or a coverage membrane.

* * * * *